(12) United States Patent (10) Patent No.: US 9,015,101 B2
James (45) Date of Patent: Apr. 21, 2015

(54) SYSTEMS AND METHODS FOR USER CUSTOMIZATION OF CLINICAL DATA OBJECTS USING A CLINICAL MODELING LANGUAGE

(75) Inventor: Alan Ferris James, Murray, UT (US)

(73) Assignee: General Electric Company, Schenectady, NY (US)

(*) Notice: Subject to any disclaimer, the term of this patent is extended or adjusted under 35 U.S.C. 154(b) by 341 days.

(21) Appl. No.: 13/401,009

(22) Filed: Feb. 21, 2012

(65) Prior Publication Data

US 2012/0246105 A1 Sep. 27, 2012

Related U.S. Application Data

(60) Provisional application No. 61/445,024, filed on Feb. 21, 2011.

(51) Int. Cl.
*G06N 5/02* (2006.01)
*G06F 19/00* (2011.01)

(52) U.S. Cl.
CPC ............ *G06F 19/324* (2013.01); *G06F 19/327* (2013.01)

(58) Field of Classification Search
None
See application file for complete search history.

(56) References Cited

PUBLICATIONS

Paar and Tichy, "Programming Language Inherent Support for Constrined XML Schema Definition Data Types and OWL DL", 21st IEEE International Conference on Automated Software Engineering (ASE'06), Tokyo, Japan, Sep. 18-Sep. 22, 2006, pp. 281-284.*
Liu, Halper, Geller, Perl, "Controlled Vocabularies in OODBs: Modeling Issues and Implementation", Distributed and Parallel Databases, vol. 7, 1999, pp. 37-65.*
Sagar Sen, Benoit Baudry, Doina Precup, "Partial Model Completion in Model Driven Engineering using Constraint Logic Programming", In Proceedings of the International Conference on the Applications of Declarative Programming, 2007, pp. 1-11.*
Mathe, Werner, Lee, Malin, Ledeczi, "Model-based Design of Clinical Information Systems", Methods of Information in Medicine, (vol. 47): Issue 5, 2008, pp. 399-408.*
Davis, "GME: The Generic Modeling Environment", Proceeding OOPSLA '03 Companion of the 18th annual ACM SIGPLAN conference on Object-oriented programming, systems, languages, and applications, 2003, pp. 82-83.*

* cited by examiner

*Primary Examiner* — Kakali Chaki
*Assistant Examiner* — Walter Hanchak
(74) *Attorney, Agent, or Firm* — Hanley, Flight and Zimmerman, LLC

(57) ABSTRACT

Certain examples provide systems, methods, and apparatus to model clinical data objects in a content-based clinical system. An example system includes a processor and a memory to implement a constraint definition language processor to define a detailed clinical model to express a clinical concept as a standardized and reusable set of clinical knowledge. The constraint definition language processor is to use a compiled, context-free constraint definition language to define the detailed clinical model as a compiled object. The constraint definition language processor is to provide the compiled object as content for at least one of a clinical content database and a clinical information system. Content represents one or more parameters to instruct a clinical application.

20 Claims, 48 Drawing Sheets

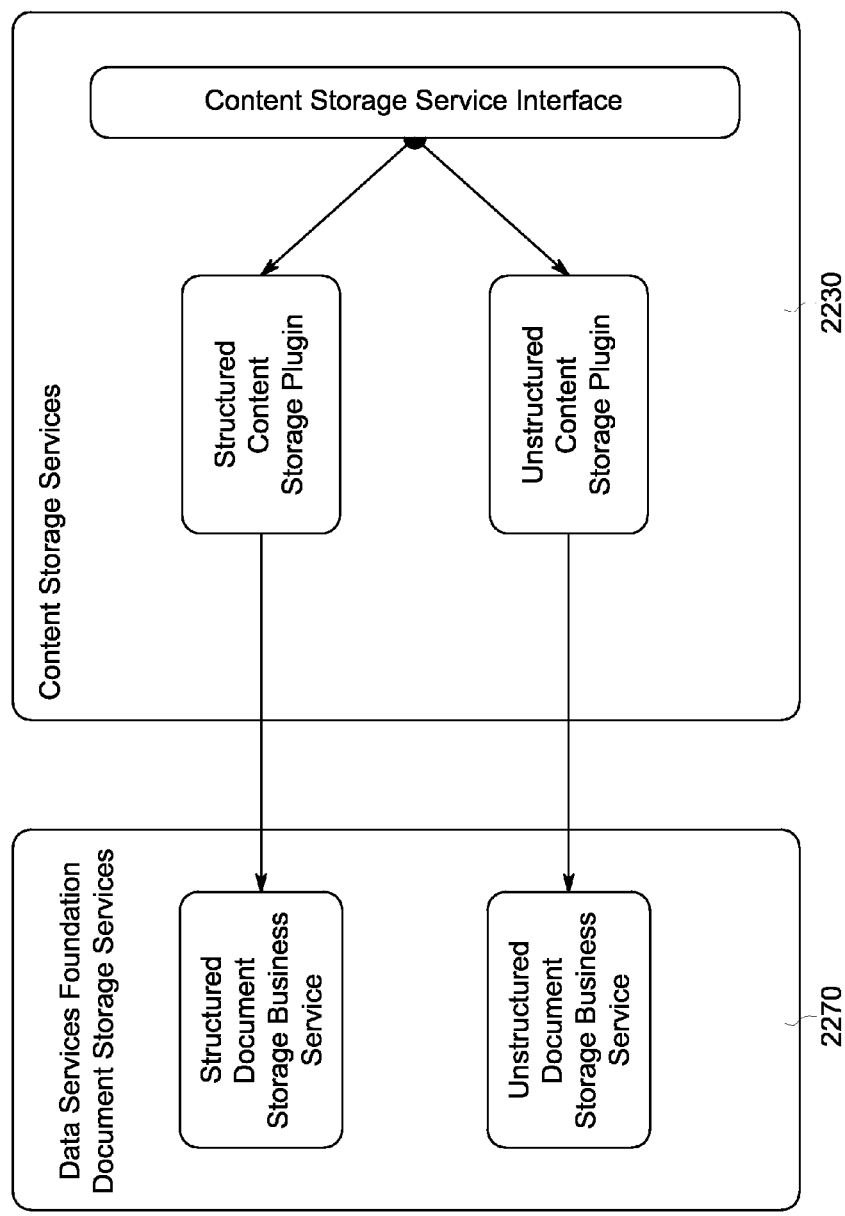

SYSTEMS AND METHODS FOR USER CUSTOMIZATION OF CLINICAL DATA OBJECTS USING A CLINICAL MODELING LANGUAGE

CROSS-REFERENCE TO RELATED APPLICATIONS

This patent claims priority to U.S. Provisional Application Ser. No. 61/445,024, entitled "Systems and Methods for User Customization of Clinical Data Objects Using a Clinical Modeling Language," which was filed on Feb. 21, 2011 and is hereby incorporated herein by reference in its entirety.

FIELD OF THE DISCLOSURE

The present disclosure relates generally to healthcare information systems and, more particularly, to methods and apparatus for content-driven systems and methods.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage clinical information such as, for example, patient medical histories, imaging data, test results, diagnosis information, management information, financial information, and/or scheduling information. These healthcare information systems are used to implement different types of workflows in which clinical information is generated, updated, augmented, and/or otherwise processed for one or more purposes.

Figure 1:
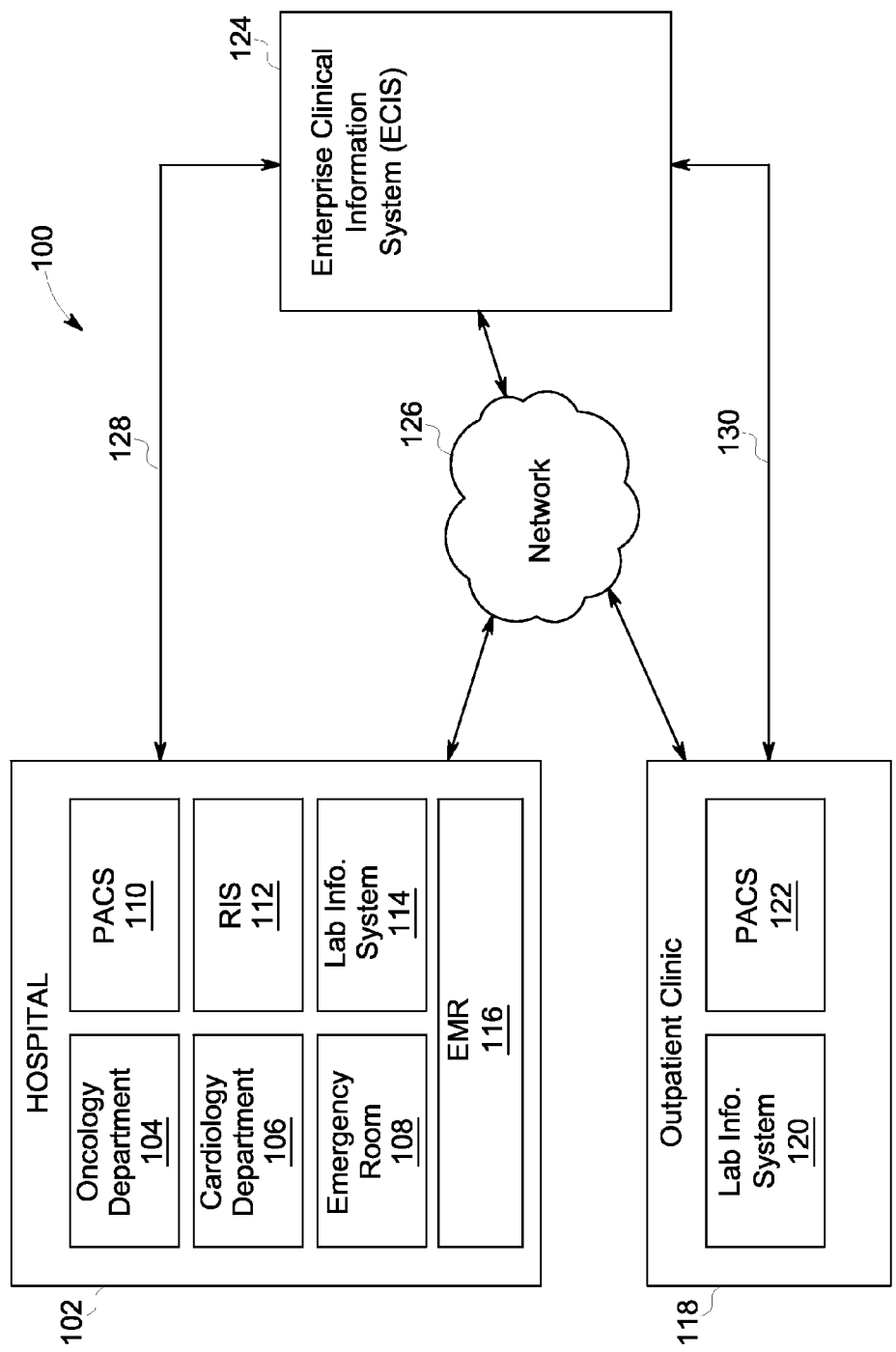
FIG. 1 is a block diagram of an example healthcare environment in which the example methods, apparatus, systems, and/or articles of manufacture disclosed herein for clinical content-based healthcare may be implemented.

The foregoing summary, as well as the following detailed description of certain implementations of the methods, apparatus, systems, and/or articles of manufacture described herein, will be better understood when read in conjunction with the appended drawings. It should be understood, however, that the methods, apparatus, systems, and/or articles of manufacture described herein are not limited to the arrangements and instrumentality shown in the attached drawings.

BRIEF DESCRIPTION

Certain examples provide systems, methods, and apparatus to model clinical data objects in a content-based clinical system.

Certain examples provide a system for user customization of clinical data objects using a clinical modeling language. The example system includes a processor and a memory to implement a constraint definition language processor to define a detailed clinical model to express a clinical concept as a standardized and reusable set of clinical knowledge. The constraint definition language processor is to use a compiled, context-free constraint definition language to define the detailed clinical model as a compiled object. The constraint definition language processor is to provide the compiled object as content for at least one of a clinical content database and a clinical information system. Content represents one or more parameters to instruct a clinical application.

Certain examples provide a tangible computer-readable storage medium including a set of instructions for execution using a processor. The instructions, when executed, providing a system including a constraint definition language processor to define a detailed clinical model to express a clinical concept as a standardized and reusable set of clinical knowledge. The constraint definition language processor is to use a compiled, context-free constraint definition language to define the detailed clinical model as a compiled object. The constraint definition language processor to provide the compiled object as content for at least one of a clinical content database and a clinical information system. Content represents one or more parameters to instruct a clinical application.

Certain examples provide a method for user customization of clinical data objects using a clinical modeling language. The example method includes receiving an input including a clinical concept. The example method includes associating the clinical concept with one or more detailed clinical models, the detailed clinical models expressing the clinical concept as a standardized and reusable set of clinical knowledge. The example method includes compiling the modeled clinical concept using a compiled, context-free constraint definition language to define the one or more detailed clinical models of the clinical concept as a compiled object. The example method includes providing the compiled object as content for at least one of a clinical content database and a clinical information system, wherein content represents one or more parameters to instruct a clinical application.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Entities of healthcare enterprises operate according to a plurality of clinical workflows. Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, and/or any other action useful in processing healthcare information. The defined clinical workflows can include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

However, the entities of a healthcare enterprise and/or entities from separate healthcare enterprises sometimes operate within a broader, interdependent information system, which hinder the ability of entities to customize clinical workflows. For example, the information system to which a healthcare entity belongs may place restrictions on changes to workflow applications or programs. Moreover, because some healthcare entities operate using systems, programs, devices, etc. from varying manufacturers, software providers, etc., a lack of interoperability between the systems, programs, devices, etc. of each healthcare entity prohibits many customizations from realization. As a consequence of these example factors as well as additional or alternative factors, healthcare entities that desire customized clinical workflows are typically required to request such customizations from the manufacturers, software providers, etc. Furthermore, for such customizations to implemented or integrated into a healthcare information system, a wide range of system-interrupting updates or re-releases occur within the information systems.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate better control over data. For example, certain example systems and methods enable care providers to access real-time patient information from existing healthcare information technology (IT) systems together in one location and compare this information against evidence-based best practices.

Certain examples facilitate better control over process. For example, certain example systems and methods provide condition- and role-specific patient views enable a user to prioritize and coordinate care efforts with an institution's agreed upon practice standards and to more effectively apply resources.

Certain examples facilitate better control over outcomes. For example, certain example systems and methods provide patient dashboards that highlight variations from desired practice standards and enable care providers to identify most critical measures within the context of performance-based care.

Certain examples leverage existing IT investments to standardize and centralize data across an organization. In certain examples, this includes accessing multiple systems from a single location, while allowing greater data consistency across the systems and users.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more IT systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

Generally, the example methods, apparatus, systems, and/or articles of manufacture disclosed herein enable healthcare entities of an enterprise clinical information system (ECIS) to dynamically customize one or more clinical workflows. Among other functions and/or benefits, the ECIS supports healthcare practitioners in decision making processes by aggregating healthcare information across disparate enterprises and/or entities thereof and referencing collection(s) of data (e.g., guidelines, recommendations related treatment and/or diagnosis, studies, histories, etc.) to automatically generate supportive information to be communicated to one or more healthcare practitioners related to the aggregated healthcare information. While each entity operates in connection with the ECIS that is administered by a provider thereof, the examples disclosed herein enable each entity of operating in connection with the ECIS to originate and/or modify one or more clinical workflows without relying on the provider of the ECIS to do so on behalf of the entity. In other words, although a healthcare entity is part of the ECIS and exchanges data with and via the ECIS, that entity can independently create and/or manage its clinical workflows using the examples disclosed herein. Furthermore, the examples disclosed herein enable entities of the ECIS to deploy or initiate the customized workflows without having to reboot or significantly interrupt the ECIS and/or the other components, workflows, etc., thereof. The example methods, apparatus, systems, and/or articles of manufacture disclosed herein and the advantages and/or benefits thereof are described in greater detail below in connection with the figures.

FIG. 1 is a block diagram of an example healthcare environment 100 in which the example methods, apparatus, systems, and/or articles of manufacture disclosed herein for clinical content-based healthcare may be implemented. The example healthcare environment 100 of FIG. 1 includes a first hospital 102 having a plurality of entities operating within and/or in association with the first hospital 102. In the illustrated example, the entities of the first hospital 102 include an oncology department 104, a cardiology department 106, an emergency room system 108, a picture archiving and communication system (PACS) 110, a radiology information system (RIS) 112, and a laboratory information system (LIS) 114. The oncology department 104 includes cancer-related healthcare practitioners, staff and the devices or systems that support oncology practices and treatments. Similarly, the cardiology department 106 includes cardiology-related healthcare practitioners, staff and the devices and/or systems that support cardiology practices and treatments. Notably, the example oncology department 104 of FIG. 1 has specifically designed clinical workflows to be executed in response to certain events and/or according to a schedule. At the same time, the example cardiology department 106 of FIG. 1 has specifically designed clinical workflows to be executed in response to certain events and/or according to a schedule that differ from the clinical workflows of the example oncology department 104 of FIG. 1. For example, the oncology department 104 may execute a first set of actions in response to receiving a Healthcare Level 7 (HL7) admission-discharge-transfer (ADT) message, while the cardiology department 106 executes a second set of actions different from the first set of actions in response to receiving a HL7 ADT message. Such differences may also exist between the emergency room 108, the PACS 110, the RIS 112 and/or the accounting services 114.

Briefly, the emergency room system 108 manages information related to the emergency care of patients presenting at an emergency room of the hospital 102, such as admission information, observations from emergency examinations of patients, treatments provided in the emergency room setting, etc. The PACS 110 stores medical images (e.g., x-rays, scans, three-dimensional renderings, etc.) as, for example, digital images in a database or registry. Images are stored in the PACS 110 by healthcare practitioners (e.g., imaging technicians, physicians, radiologists) after a medical imaging of a patient and/or are automatically transmitted from medical imaging devices to the PACS 110 for storage. The RIS 112 stores data related to radiology practices such as, for example, radiology reports, messages, warnings, alerts, patient scheduling information, patient demographic data, patient tracking information, and/or physician and patient status monitors, as well as enables exam order entry (e.g., ordering an x-ray of a patient) and image and film tracking (e.g., tracking identities of one or more people that have checked out a film). The lab information system 114 stores clinical information such as lab results, test scheduling information, corresponding practitioner(s), and/or other information related to the operation(s) of one or more labs at the corresponding healthcare facility. While example types of information are described above as being stored in certain elements of the hospital 102, different types of healthcare data may be stored in one or more of the entities 104-114, as the entities 104-114 and the information listed above is included herein as non-limiting examples. Further, the information stored in entities 104-114 may overlap and/or be combined into one or more of the entities 104-114. Each of the example entities 104-114 of FIG. 1 interacts with an electronic medical record (EMR) system 116. Generally, the EMR 116 stores electronic copies of healthcare records associated with, for example, the hospital 102 and the entities 104-114 thereof.

The example healthcare environment 100 of FIG. 1 also includes an outpatient clinic 118 as an example of another healthcare enterprise. The example outpatient clinic 118 of FIG. 1 includes a lab information system 120 and a PACS 122 that operate similarly to the corresponding entities of the example hospital 102. The lab information system 120 and the PACS 122 of the example outpatient clinic 118 operate according to specifically designed clinical workflows that differ between each other and the clinical workflows of the entities 104-114 of the hospital 102. Thus, differences in clinical workflows can exist between the entities of a healthcare enterprise and between healthcare enterprises in general.

In the illustrated example of FIG. 1, the hospital 102 and the outpatient clinic 118 are in communication with an ECIS 124 via a network 126, which may be implemented by, for example, a wireless or wired Wide Area Network (WAN) such as a private network or the Internet, an intranet, a virtual private network, a wired or wireless Local Area Network, etc. More generally, any of the coupling(s) described herein may be via a network. Additionally or alternatively, the example hospital 102 and/or the example outpatient clinic 118 are in communication with the example ECIS 124 via direct or dedicated transmission mediums 128 and 130.

Generally, the ECIS 124 supports healthcare information processing implemented by systems, devices, applications, etc. of healthcare enterprises, such as the hospital 102 and the outpatient clinic 118. The ECIS 124 is capable of processing healthcare messages from different entities of healthcare enterprises (e.g., the entities 104-114 of the hospital 102) that may generate, process and/or transmit the healthcare messages differently and/or using different formats, protocols, policies, terminology, etc. when generating, processing, and/or transmitting the healthcare messages. Moreover, the example ECIS 124 of FIG. 1 supports healthcare practitioners in decision making processes by aggregating healthcare information across disparate enterprises and/or entities thereof and referencing collection(s) of data to automatically generate suggestive and/or definitive data for communication to one or more healthcare practitioners related to the aggregated healthcare information.

Certain examples provide a library of standardized clinical content and proven best practices. Over time, this "library" of content may expand as healthcare organizations add to their own content modules. Because the content is standardized it can be shared and leveraged among organizations using the library and associated clinical knowledge platform. The library and platform help enable organizations to share best practice content. Thus, certain examples provide a clinical knowledge platform that enables healthcare delivery organizations to improve performance against their quality targets.

In certain examples, a quality dashboard application enables creation of one or more dashboards based on the data/content most relevant to an organization at a given period of time. A clinical knowledge platform brings together real-time patient data from existing IT systems within an organization and allows for the comparison of this data against evidence-based best practices. The example quality dashboard application leverages the platform to enable personalized "Quality Dashboards" to be created for specific sets of patients, based on condition, role, and/or other criteria. Variations from desired practice will be highlighted on each dashboard, enabling care providers to ensure better clinical outcomes and enrich patient care.

Figure 2:
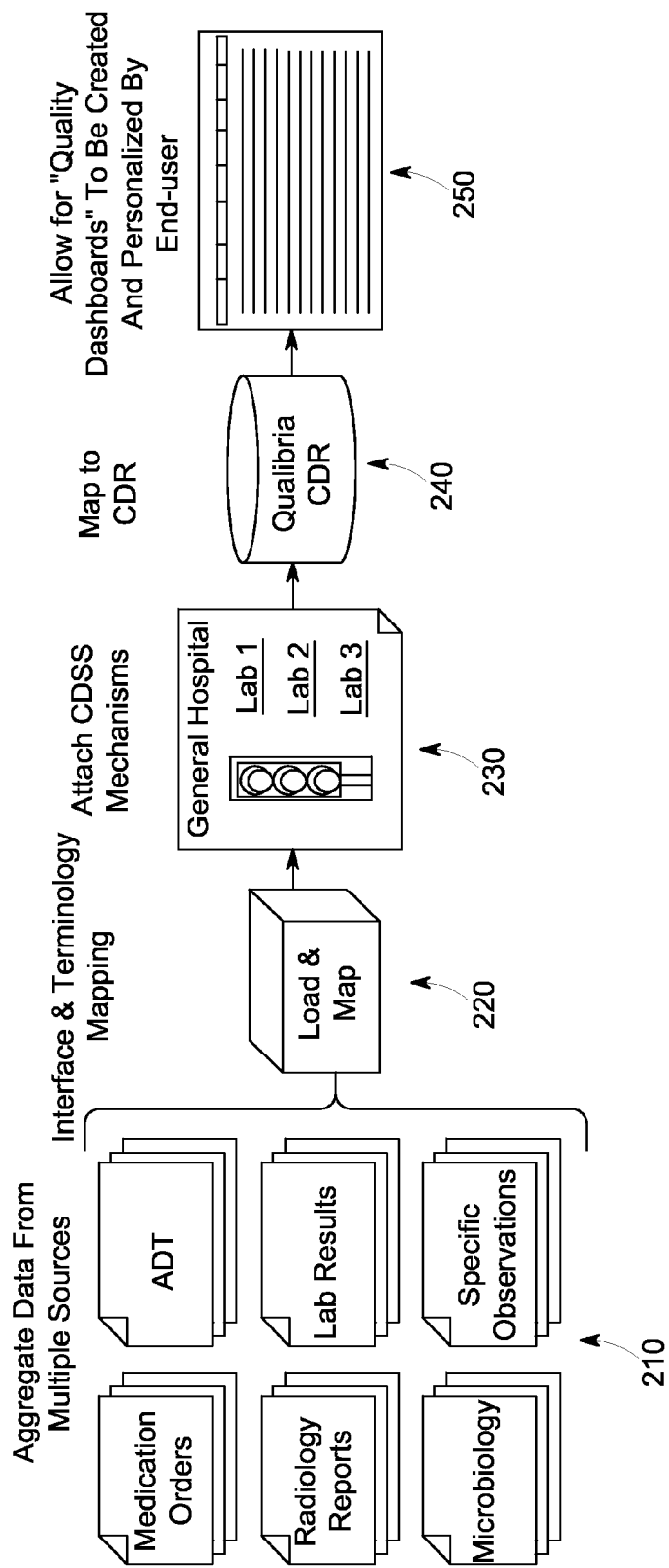
FIG. 2 illustrates an example clinical knowledge system providing an aggregation of data from multiple sources.

In this example, the clinical knowledge platform aggregates data from an organization's existing IT solutions. These can be solutions from the same and/or different manufacturer and/or provider. For example, as long as there is an HL7 or Web Services feed, the clinical knowledge platform can utilize the data from an existing solution. The existing IT solution(s) will continue to operate as they always have, and an organization can continue to use these solutions separate from the clinical knowledge platform if they so desire. However, the clinical knowledge platform and associated application(s) and/or workflow(s) can help to put organizations in greater control of their data by aggregating as much data from disparate IT solutions as possible. FIG. 2 illustrates an example clinical knowledge system 200 providing an aggregation 210 of data from multiple sources. Aggregated data may include, for example, medication orders, radiology reports, microbiology, admit/discharge/transfer (ADT) message, lab results, specific observations, electronic medical record (EMR) data, etc.

As the different data sources are pulled into a central data repository, content standardization occurs. It is this "standardization" that enables content from different IT sources to be used together. For example, as shown in FIG. 2, an interface 220 provides terminology mapping and standardization to the aggregated data.

After the content is standardized, clinical decision support mechanisms can be tied to the content (as illustrated, for example, by the clinical decision support 230 of the system 200 of FIG. 2). The data and associated clinical decision support are then stored in a clinical data repository (CDR), such as CDR 240 of the example system 200. By combining the aggregated and standardized data with clinical decision support rules and alerts, the clinical knowledge platform may provide end-users with an understanding of important elements to which they should pay attention (and take action on) within the larger set of data they are considering when caring for a patient.

Combined data and clinical decision support mechanisms create valuable content that, when arranged properly, may be used to improve the quality of care provided. Organizations can elect to use the application(s) that are provided as a part of the example clinical knowledge platform and/or may choose to build their own clinical application(s) on the platform. The open architecture nature of the platform empowers organizations to build their own vision, rather than base their vision on the static/hard coded nature of traditional IT solutions.

In certain examples, "Quality Dashboards" created via an example application display data via columns and rows in addition to individual patient "inspector" views. For example, the system 200 shown in FIG. 2 provides one or quality dashboards 250 to be created and personalized by an end user. The flexible nature of this dashboard application empowers organizations to create dashboards of the aggregated data based on their needs at a given period of time. The organization may determine what data elements they would like to include on each dashboard and, without significant IT resources, create a dashboard that reflects their vision. In addition, organizations can determine where on the dashboard they would like the information to be displayed and further adjust the view of the content via features such as "bolding" font, etc. When data is added to each dashboard, clinical decision support mechanisms attached to this data are displayed on the dashboard as well. For example, content related to treating a patient based on a particular use case may be included on a quality dashboard, along with alerts and notifications to indicate to end-users when desired outcomes are varying from defined clinical standards. Thus, organizations can create dashboards based on their own idea of "best practice" care for a given disease state.

In certain examples, since combined content and best practices have been standardized, content from one organization using the clinical knowledge platform may be easily shared with other organizations utilizing the platform. In addition, because the content within platform-related applications is standardized in the same manner, upgrades/updates to the example platform can occur efficiently across organizations. That represents a dramatic change from prior IT solutions which require unique IT upgrades because they are usually uniquely customized to each organization in which they are installed.

Generally, content is information and experience that may provide value for an audience. Any medium, such as the Internet, television, and audio CDs, may deliver content as value-adding components. To analogize to consumer media to illustrate an example relationship, content represents the deliverable, such as a DVD movie, as opposed to the delivery mechanism, a DVD player. As long as content conforms to the media standard, any compatible device can play it.

Content, as used herein, is the externalization or parameterization of "the instructions" that tell applications how to work. For example, content is a collection of externalized information that tells software, in conjunction with data, how to behave. In certain examples, a clinical knowledge platform takes in and executes content against data to render applications visually and behaviorally.

Content includes data read and interpreted by a program to define or modify presentation, behavior, and/or semantics of the program and/or of application data consumed by the program, for example. Content includes documents presented to a client by a program without modification, for example. Content may be created, stored, deployed, and/or retrieved independently of the creation and deployment of the program(s) consuming the data, for example. Content may be versionable to capture desired variation in program behavior and/or semantics, for example.

Classes of content may include configuration content, preferences content, reference content, application content, etc. Content types may combine behaviors of two or more classes, for example.

Software vendors take many different approaches to customization. At one extreme, some vendors write different software for each customer or allow customers to write software. At the other extreme, a vendor has the same software for each customer, and all customization occurs through creating or modifying content. In certain examples, the same software may be used for each customer, and customization is handled through content.

In healthcare, new laboratory tests, medications, and even diseases are constantly being discovered and introduced. Structuring this as content, where underlying software does not need to change, helps accommodate and use updated information.

In certain examples, many different content types, such as form definitions, data models, database schema, etc., are accommodated. In certain examples, each content type may be used differently and involve a distinct authoring tool. Thus, in certain examples, content may refer to "a collection of the content instances for all content types," also called a content repository, knowledge repository, or knowledge assets. For example, a content instance is a specific member of a content type, such as a heart rate data model.

In certain examples, each content type is associated with a generic, extensible structure that content instances of the content type follows. An example clinical information system can specify content in an abstract way that does not presuppose a particular software implementation, for example. That is, another system, such as GE's Centricity Enterprise, may consume content from a knowledge repository, apply a different set of software, and achieve the same behaviors. Additionally, an abstract content definition can more easily transition to a new system. If one can extract content from a legacy system, a knowledge repository may be able to import and reuse it. Such a capability helps reduce a large barrier to change for potential customers.

Content can change with time. In an example, a current knowledge repository can handle any "old" data entered into a system under the auspices of an older knowledge repository. Occasionally, a question may arise where someone could ask, "What did Dr. Smith see at some past time?" Under these circumstances, a current definition of a particular display may not correctly reflect the situation at the time. An example CIS, unlike other systems, can bring back the old form for visualizing the data since all knowledge assets are versioned and retained.

Content may need to vary for different circumstances. For example, an MPV may differ between emergency department (ED) and labor and delivery settings. Each MPV has rows and columns of data specific to its setting. Context refers to being aware of and reacting distinctively to a location and other situational differences. For example, interpretation of a patient's low temperature can vary based on location. If it occurs in the recovery room after cardiopulmonary bypass with deliberate patient cooling, it means one thing. If the patient is in the ED after breaking through ice into a lake, it means something completely different. Context may vary based on user location, patient location, user role, and/or various other factors. In certain examples, content may be applied based on context.

Globalization is a process of adapting software so that it has no language references, before embedding capabilities to make it suitable for particular languages, regions, or countries. Having globalized it, a CIS may then translate it to other languages and cultures, called localization. Globalizing a software product involves creating content separate from the software. For example, embedded text (e.g., user messages), sort orders, radix characters, units of measure, data formats, currency, etc., may be removed and parameterized. References to languages, character sets, and fonts may also be removed, for example. In certain examples, while display representations may be local, terminology concepts are applied universally, making a rule, calculation, or other content based on one or more terminology concepts useable worldwide without modification.

Figure 3:
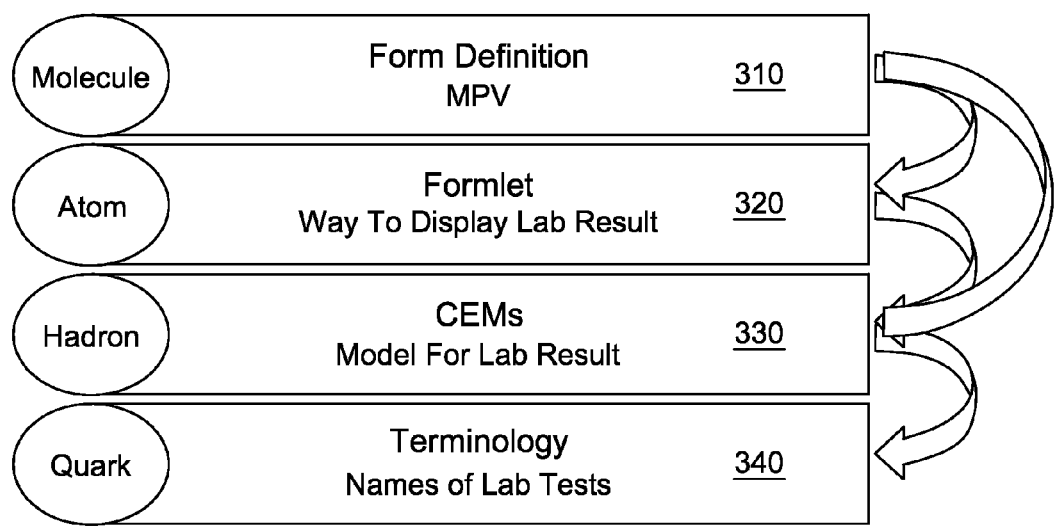
FIG. 3 illustrates an example interdependence of content types.

For example, FIG. 3 illustrates an example interdependence of content types. As shown in the example of FIG. 3, content is a set of interdependent building blocks. Content may be thought of as a hierarchy, with terminology 310 (e.g., names of lab tests) as a lowest level. Terminology 310 may be common and coded across a customer base. Clinical element models (CEMs) 320 govern structure and content of objects stored in a database and used by applications. A formlet 330 provides a way to display a particular content item (e.g., a way to display a particular lab result). A form definition 340 provides an application or view (e.g., a dashboard) of a collection of formlets (e.g., a multi-patient view (MPV) showing one or more lab results and/or other information). For example, if a particular MPV definition is moved from one customer to another, the MPV definition along with other content items on which the form definition depends are imported into the new customer's knowledge repository. Content items may include appropriate formlets, CEMs, and terminology, for example.

In certain examples, the Clinical Element Model presents a model for describing and representing detailed clinical information wherein each item of clinical information is defined using a detailed model of the information (that is, Detailed Clinical Models).

An example logical model to represent such a Detailed Clinical Model uses a two-layer data modeling approach in which the structure or representation of a clinical data object (that is, an instance of data) is separated from the definition of the information contained within the clinical data object (that is, a model defining the instance of data). This logical model defines the information in a Detailed Clinical Model as a set of constraints progressively limiting (and/or restricting) allowable data values in a Detailed Clinical Model until a specific clinical data item is defined.

In certain examples, a computer language, referred to as a Constraint Definition Language (CDL), is provided to define Detailed Clinical Models and constraints used to describe a specific clinical data item.

In certain examples, a detailed clinical model defines, at a granular level, the structure and content of a data element. For example, the detailed Clinical Model for "Heart Rate Measurement" dictates the data type of a heart rate measurement, and the valid physiologic range of a heart rate. It says that a "body location" is valid qualifying information about a heart rate measurement, but a "color" is not. It further decrees that the valid values for "body location" are terminology codes found in the "heart rate body location" value set. Moreover, it prescribes that a "resting heart rate" is an instance of "Heart Rate Measurement" where the value of "temporal context" is "resting", where "resting" is also a coded value. A detailed clinical model pulls the information together into a single, explicit, and computable form. The detailed clinical models or clinical element models (CEMs) govern the content and structure of all data objects stored in an example clinical database and used by applications, for example. In addition, CEMs are extensible, such that content authors may add new CEMs or attributes to existing CEMs without requiring major changes to database structures or software, for example.

In certain examples, shared or portable content is, in effect, "plug 'n play". System administrators can add it (e.g., plug it into) to a system without any software changes, and the content behaves in the intended way and does not cause errors. The size or scope of shared content can range from a single term to an entire knowledge repository, for example. Shared content fundamentally changes an implementation paradigm and reduces a total system cost of ownership, for example.

Customers can change shared content. Customers can improve it or make it more suitable for their institutions. When customers do this, they leave the original definition intact, but clone it and keep their changed version in their "local" space, for example.

As described above, classes of content may include configuration content, preferences content, reference content, application content, etc. Configuration content is content that is modified infrequently and is concerned primarily with system behavior, for example. Examples of configuration content may include internet protocol (IP) address and port of clinical knowledge database, identifiers of terminals in systems, security access privileges, configuration files, etc. Configuration content may affect program semantics, for example. Configuration content is generally modified by system administrators and is often stored in the file system, for example.

Preference content is modified frequently and is concerned primarily with variation between users. Examples of preference content include display colors and fonts, default search parameters, screen layout, etc. Preference content rarely affects program semantics and is most commonly modified by individual users. While modified by users, the system generally distributes initial or default preference content.

In certain examples, distributed or default preference content behaves very similar to application content before modification by a user. Preference content may be context sensitive, transformed at deployment, etc. Preference content may include vocabulary concepts and pick-lists that are resolved when loading and retrieving just like other content types.

Reference content is documents that are presented without modification as part of the application. Reference content is often stored in formats that are opaque to a program (e.g., as a PDF, a Microsoft Word™ document, etc.). Reference content is generally not specific to or customized for a specific patient (e.g., instruction sheets, information sheets, policies and procedures, etc.). Reference content may be independent of program semantics and behavior. Reference content may be authored independently of a program. While not an element of a content drive system per se, reference content is often managed as content by a clinical knowledge system. Once reference content is modified for presentation to a specific user, the content starts behaving much more like patient data/documents. Reference content with the structure to enable modification starts behaving much more like application content.

Application content may be modified frequently or infrequently depending on use. Application content may be concerned primarily with application behavior and semantics. Applicant content may be generally specific to an application domain. Examples may include a flow sheet template, clinical element models, terminology, document templates that are modified and stored as patient data (e.g., hot text), etc. Terminology is application content but has behaviors distinct from other application content types and is managed (largely) independently of other application content, for example. Application data often affects program semantics and behavior. Application content may be authored at multiple levels in an organization or external to the organization, for example.

Application content may be implemented as a custom markup language, for example. Application content may be implemented as a domain specific language (DSL), for example. For example, data queries may be implemented using a frame definition language (FDL). Clinical element models may be implemented using a constraint definition language (CDL). Application content may be directly authored or imported as data into a content store (e.g., concepts in a vocabulary server), for example.

In certain examples, while patient data is transactional and often includes discrete data elements, application content is often structured, complex objects and often has associated metadata. In certain examples, metadata is data used to manage content, such as content identifier, version, name of author, access privilege, encryption certificate, etc. Metadata is not treated as content, for example. While patient data is owned by a patient and is part of a legal record, application content is not owned by a patient and is not part of a legal record. Application content may be published (e.g., is not transactional) and managed using a lifecycle.

Certain examples provide content-driven systems and processes that rely primarily on content to determine application behavior. An example system includes a reference platform that consumes, interprets, and/or executes content while remaining application neutral. An example system uses content that remains independent of an implementation of the reference platform to allow independent evolution of the platform and the application.

Figure 4:
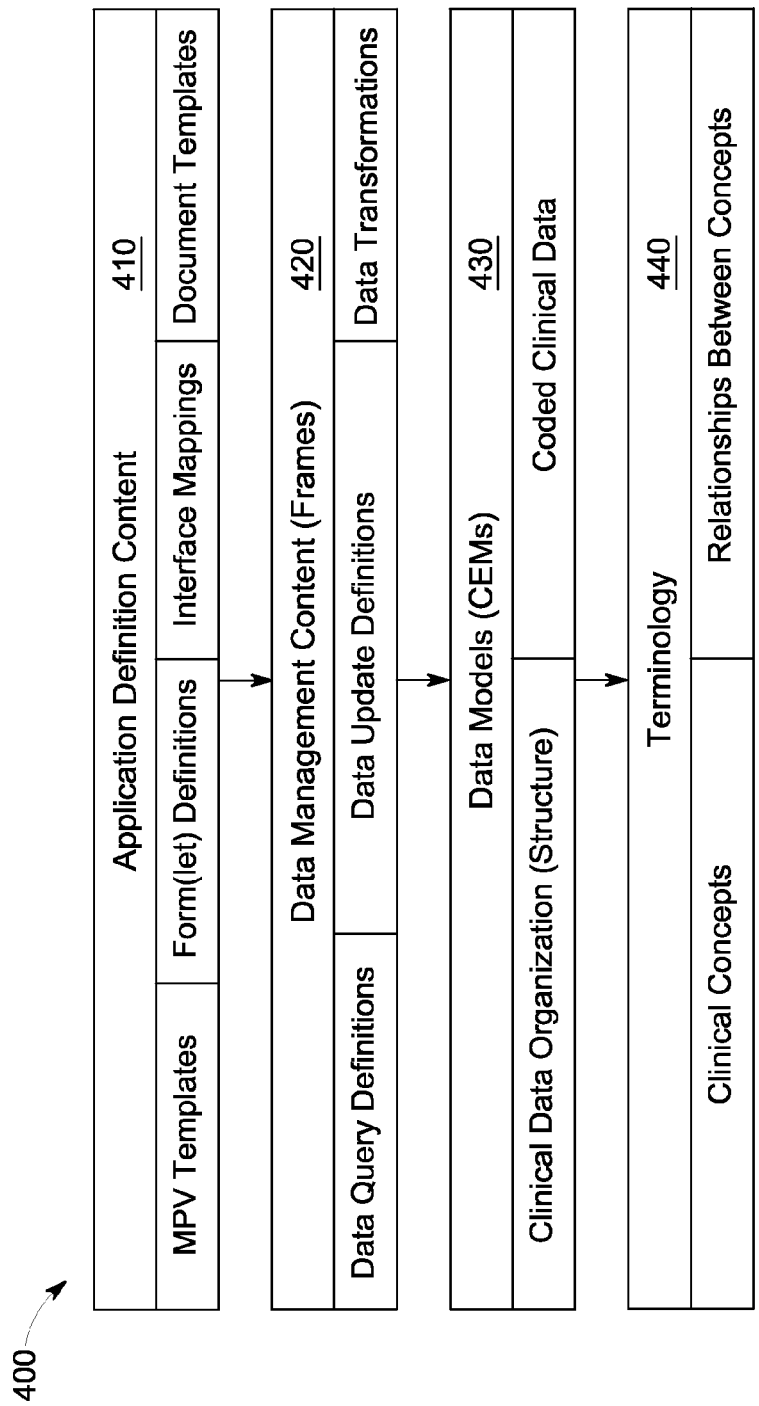
FIG. 4 illustrates an example hierarchy of content, associated data models, and terminology.

FIG. 4 illustrates an example hierarchy 400 of content, associated data models, and terminology. In certain examples, once one chooses content based data models, content-based queries and data management are also selected. Content based applications are also chosen. An integral terminology basis includes semantics of data defined in terminology content, for example. As shown in the example of FIG. 4, application definition content 410 (e.g., MPV templates, form(let) definitions, interface mappings, and/or document templates, etc.) relies on data management content (e.g., frames) 420 (e.g., data query definitions, data update definitions, and/or data transformations, etc.). The data management content 420 leverages data models (e.g., CEMs) 430, such as clinical data organization (e.g., structure) and/or coded clinical data, etc. The data models 430 are constructed based on a terminology 440 including clinical concepts and relationships between concepts, for example.

In certain examples, context refers to metadata attributes and/or labels that differentiate variations of a content item. For example, each variant of content item may be referred to as a context variant. Each variation of a content item has a specific set of context attributes (e.g., language, location, role, etc.). An algorithm or heuristic may select a desired variant when retrieving based on a current user's "context." This process may be referred to as context resolution.

Searching refers to examining the content item and/or associated metadata for matches independent of context. Searching can include context attributes to filter for specific context variants in the search. The difference is that a specific variant is not selected algorithmically or heuristically by the content system when searching. Using the "user" as a context attribute is one way to associate a content item with a specific user; similarly provider as a context variable could be used to associate an item with a group of users. Resolving context generally requires some heuristic to resolve ambiguity or conflicts among context variants (e.g., weighting or priority schemes, default rules, etc.). This leads to some ambiguity since changing/adding a context variant or changing the weights of context attribute may change the context resolution on another item in not always obvious ways (at least to a user).

In certain examples, a content item includes:

1. A root content item represented by a universally unique identifier (UUID). The root content item includes metadata only; no actual content is stored.

2. One or more context variants that represent variations of an implementation of the content item in different client contexts occur as children of the root content item.

3. Context variants may form trees of increasing context specialization (e.g., a context variant may have child variants).

4. Each context variant has a unique UUID as well as a relation to the root content item.

5. Each context variant maintains versions of that variant as changes are applied to the variant.

Figure 5:
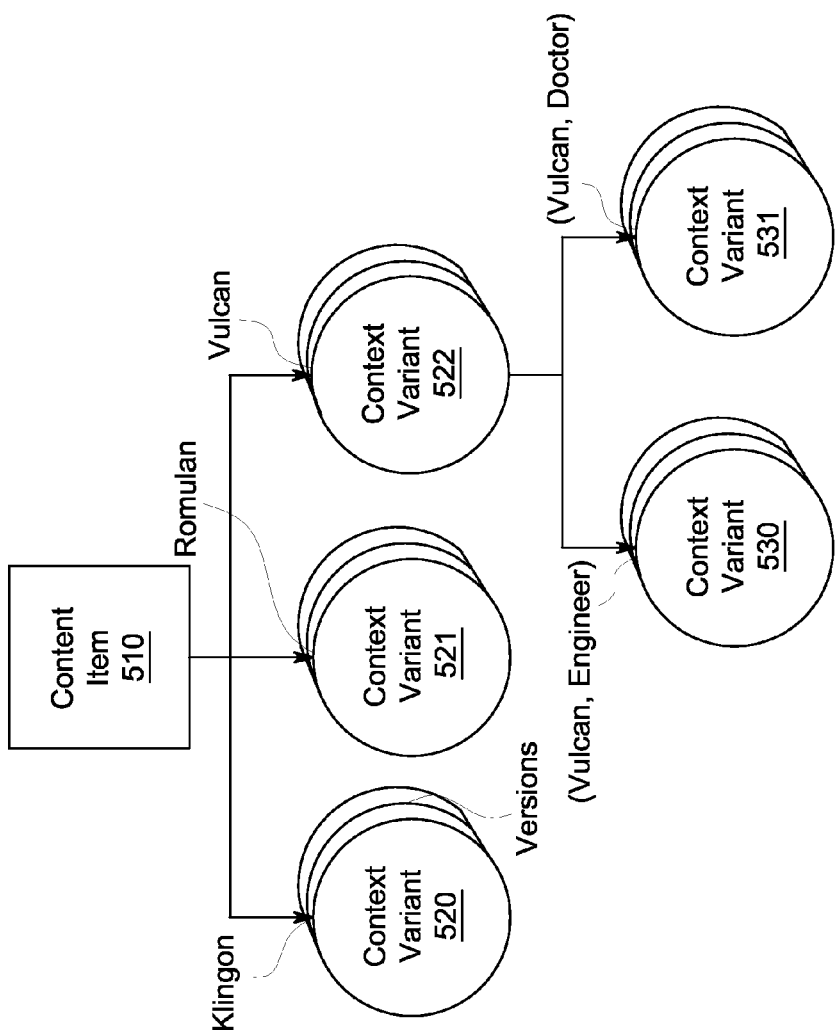
FIG. 5 shows an example root content item having one or more content variants which may be associated with one or more context variants.

As shown in the example of FIG. 5, a root content item 510 has one or more content variants 520-522. Each content variant 520-522 may be associated with one or more context variants 530-531.

Figure 6:
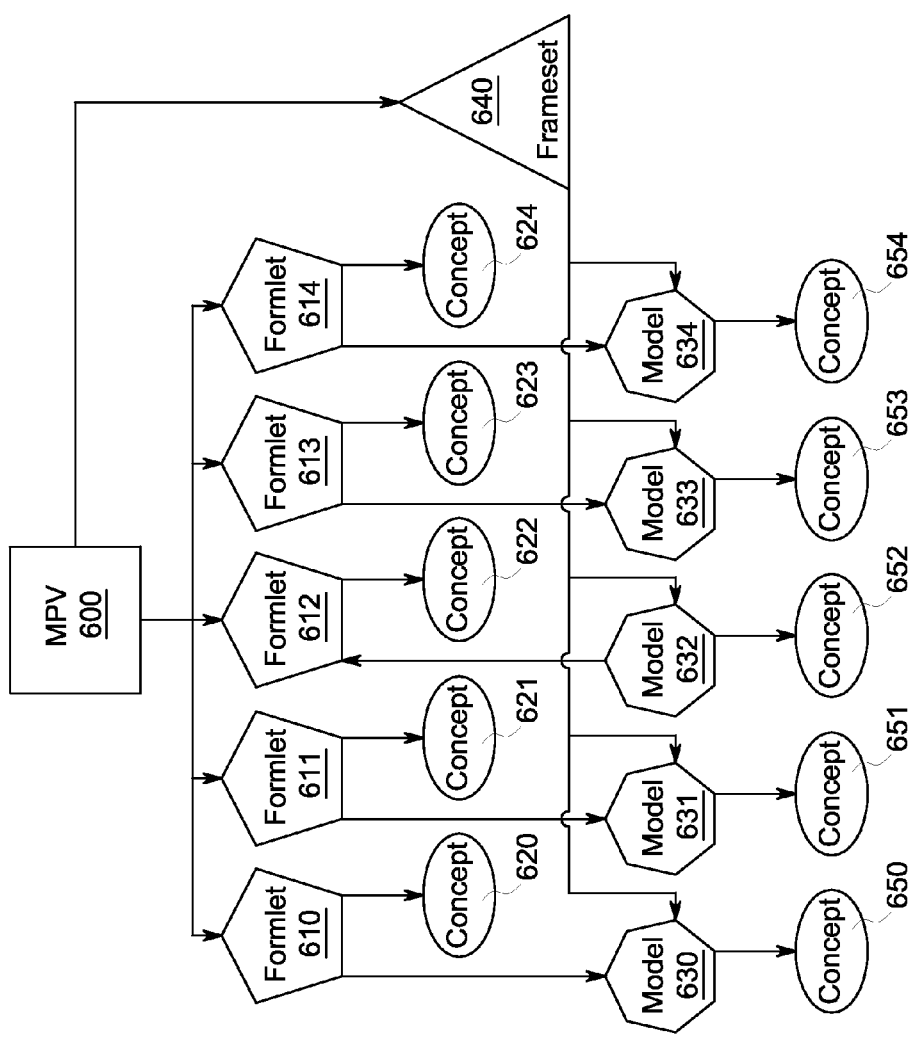
FIG. 6 provides an example multi-patient view (MPV) including a plurality of formlets and a frameset.

FIG. 6 provides an example multi-patient view (MPV) 600 made up of a plurality of formlets 610-614 and a frameset 640. Each formlet 610-614 corresponds to a concept 620-624 and a model 630-634. The frameset 640 is also associated with each model 630-634, and each model 630-634 is associated with a concept 650-654, for example.

In certain examples, content may be stored in multiple content stores. For example, content may be stored in an ECIS database, an XDS repository, a third-party system, etc. Content documents in storage may be identified by a URI that specifies the content store and the key of that item in that content store. A content directory including the content metadata may be searched to obtain the URI for retrieval of the content item. A content type manager may specialize the search, storage, and/or retrieval of items of that content type, for example.

A content item in the content directory is keyed via a UUID for the item. That UUID is not necessarily part of the uniform resource indicator (URI) that defines the storage location.

In certain examples, content items may be organized as a content type. A content type is a set of content items that are defined and managed using common definitions and methodologies (e.g., terminology, clinical element models, frameset definitions, etc.). Content types may have different behaviors, states, lifecycles, etc. Each content type may be managed by a specific content type manager, which is treated as a plug-in to a clinical knowledge platform and/or associated clinical information system, for example. Content types may be added by creating a new content type manager, for example.

Content type managers may interact with a content management framework by implementing a set of event handlers (e.g., package, deploy, retrieve, etc.). "Generic" content types (e.g., content types with no special behavior) may use a default content type manager. An owner of a content type is responsible for implementing an associated content type manager, for example.

In certain examples, during authoring (that is, before deployment), dependencies exist between content items. At runtime (that is, after deployment), dependencies exist between deployed forms of context variants. Dependents that exist during authoring may or may not continue after deployment. For example, terminology description and pick-list resolution are translations during loading and retrieving, not dependencies per se.

In certain examples, at runtime, dependencies are between deployed forms of context variants, not the context variants themselves. The deployed form of a context variant is a "content frame". At deployment time, it may be necessary to guarantee that the packages (e.g., terminology) that a package depends on are also deployed. Terminology dependencies may be inferred from terminology relationships and mappings and do not need to be explicitly tracked.

In certain examples, a content based system provides a capability to distribute content and content updates to external instances (e.g., test systems, quality assurance systems, customer installations, content patches (e.g., SPRS), etc.). An example distribution system provides a capability to distribute content items and associated dependent content items and/or insure that those content items already exist in the target system. For example, an FDL content item must have access to the clinical element types it references in order to process a frame query. The example distribution system may also facilitate an undo or reversal of installed content items that generate issues. Content may be distributed as large sets of items (e.g., during installation) and/or as individual items (e.g., bug fixes), for example.

Figure 7:
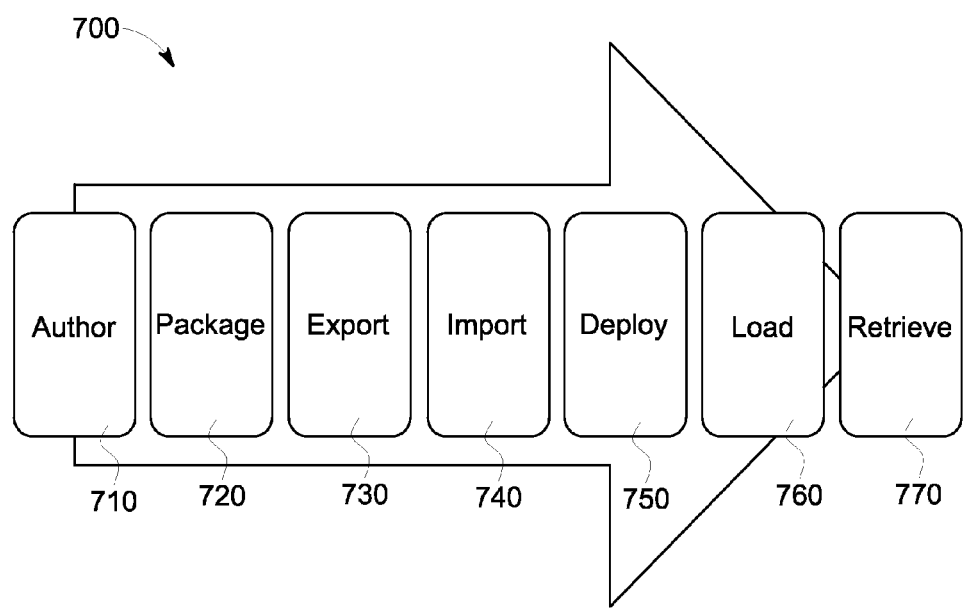
FIG. 7 illustrates an example content management process.

FIG. 7 illustrates an example content management process 700. The example process 700 includes authoring 710, packaging 720, exporting 730, importing 740, deploying 750, loading 760, and retrieving 770.

Authoring 710 includes a process of creating and/or modifying a content item. Authoring may be done by an author composing content directly using an editor (e.g., CDL, FLD, etc.), for example. Authoring may be done using tools (e.g., editor(s), etc.) that are specific to a content-type (e.g., terminology), for example. Authoring may be done by tools within the application(s) consuming a content type (e.g., MPV, forms, etc.), for example. Authoring may be done by applications generating a content item (e.g., MPV generating FDL), for example. In certain examples, there is no single authoring environment for content; rather, there is a family of authoring tools that is often content type specific.

Packaging 720 includes combining all content items and (applicable) context variants within a transitive closure of dependency graphs of one or more content items into a package, for example. Packages may include multiple independent top level content items, for example. Packages may have dependency(-ies) on other package(s). For example, a package containing a frameset content item may dependent on a separate terminology package as a prerequisite to deployment.

Packages may very frequently contain multiple independent, top level items each with its associated dependency graph. A package may not include all context variants of an item. For example, packaging may filter based on context to form a package. Packaging events may include an event to allow a content type manager to specify dependencies of an item being packaged.

Packages may have dependencies on content types other than content packages. For example, a terminology package is a different content type than a content package. Content items within a package may not have explicit dependencies on terminology concepts. Rather, the package has dependencies on the appropriate terminology packages.

In certain examples, packages are used as a distribution mechanism. Packages may be deployed before items in the package are available to a runtime system, for example. Packages themselves may be treated as content items. Thus, packages can themselves be packaged (e.g., packages of packages), and packages may be dependent on other packages. In certain examples, packages may belong to a namespace or domain. For example, packages may only include items from a single namespace. Packages may have dependencies on packages in another namespace, for example.

Package(s) may be exported 730 from one system and imported 740 into another. Exported packages may be used to distribute content, for example. System management tool(s) may be provided to create, export, import, and deploy content packages, for example.

Figure 8A:
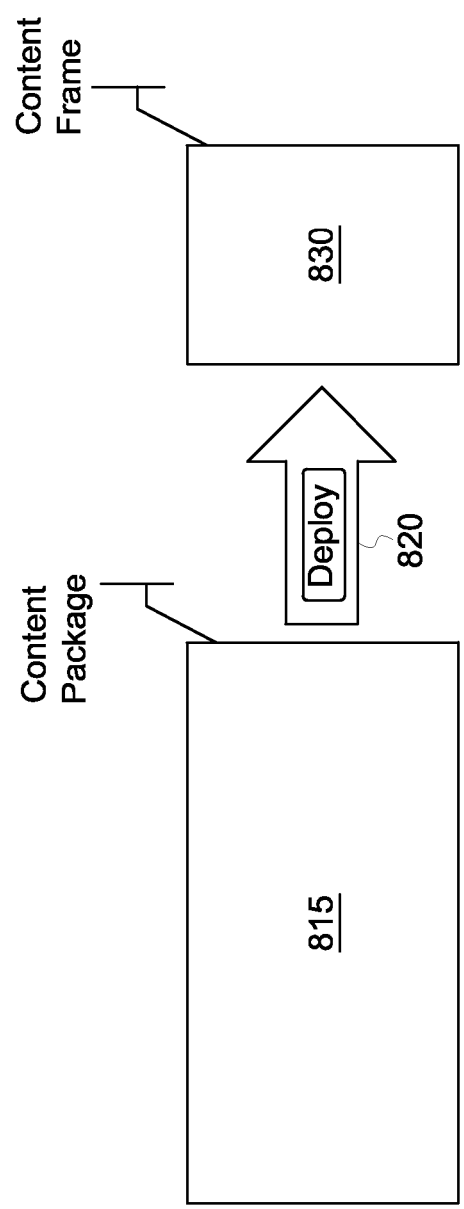
FIG. 8 shows a deployment example in which a plurality of models in a content package are deployed to create a content frame.
Figure 8B:
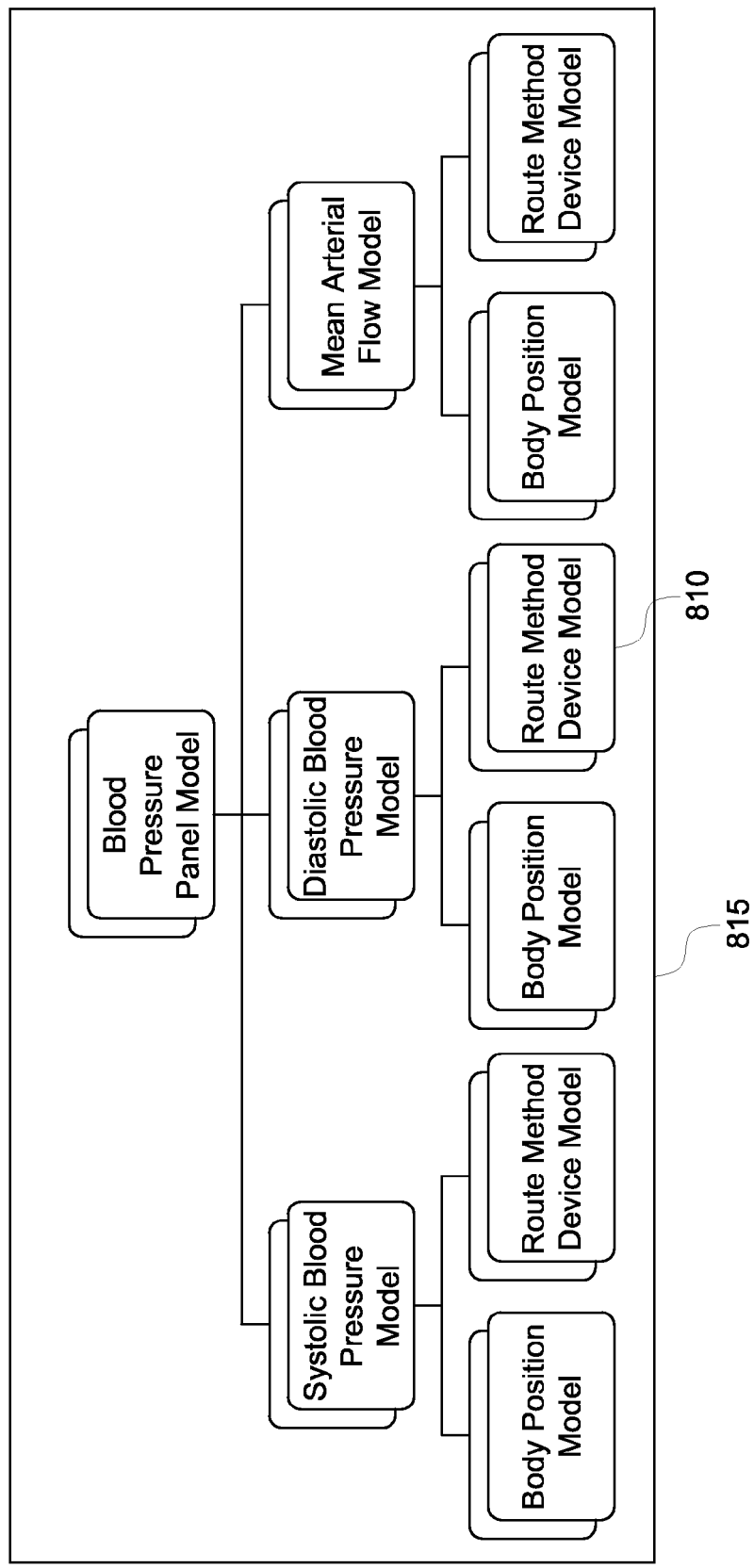
Figure 8C:
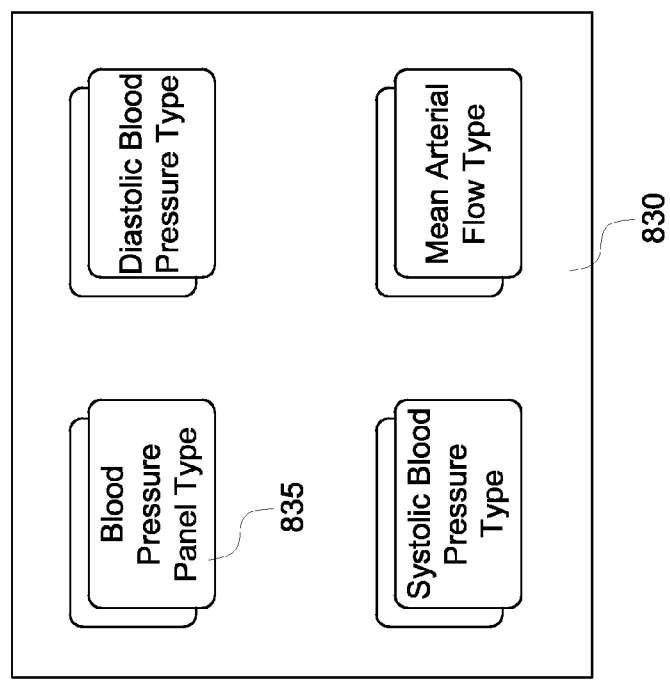

Deploying 750 includes making content items included within a package available to a running system. A content item may be transforming during deployment, for example. For example, constraint definition language (CDL) models may be compiled and may create multiple type objects each with an associated schema. As shown in the deployment example of FIG. 8, a plurality of models 810 in a content package 815 are deployed 820 to create a content frame 830 including plurality of type objects 835 with associated XML schema.

In certain examples, each top level content item in a package being deployed is deployed independently. A deployed content item is logically (and often physically) a different object than the content item being deployed. For example, a deployed content item has independent state and lifecycle. Multiple content items may be created during deployment, for example. For example, deploying a CDL model may generate a CE type object and an XML schema. In certain examples, a source content item may not exist in the runtime system. For example, the source CDL models are not employed, and the generated CE type object is deployed. Deployment of a package may be done manually and/or implicitly by an authoring tool, for example. For example, system administrators may wish to explicitly control deployment of data models but MPVs authored by a user may be implicitly and immediately deployed.

In certain examples, each deployed content item is bundled with all of the content items that are used to execute and/or consume the item. The bundle is referred to as a content frame 830. A content frame 830 is analogous to an archive file manifest. It may not (necessarily) contain the actual content items. The content frame 830 may not include all of the items generated during deployment. For example, the CDL schemas may not be part of the frame.

A content frame 830 is also analogous to a context variant. The frame has its own unique identifier but may be retrieved using the identifier of the root content item the frame is based upon in the same way that context variants are retrieved. Deployment events may include an event to allow the content type manager to specify dependencies of the deployed item(s) within the content frame, for example.

In certain examples, context resolution refers to conditioning selection, composition, and/or behavior of a content item based on a context of a user. Context resolution may occur at one or more levels. For example, context resolution may occur on selection of the content item(s) that a content item being deployed is dependent upon based on context. Such resolution occurs during deployment, and content frames are context specific with dependencies resolved. Context resolution may occur on selection of a content frame based on context when the content frame is retrieved by an application, for example. Context resolution may occur on translation of a content item based on context when loading and/or retrieving a content frame, for example. For example, context resolution may occur upon retrieval of terminology concept designations and/or retrieval and population of pick-lists.

Translation may be performed by the content type manager during loading and/or retrieval, for example. A template tool such as Apache Velocity may be used to implement the translation. The sensitivity of a content item to changes in the terminology server is a function of when the translation is applied e.g., during deployment, loading, or retrieval), for example. During deployment, context may be used algorithmically/heuristically to select dependent items and/or the deployment tool may specify the required dependent items. In general, context resolution is done heuristically (e.g., scoring and weighting schemes) because of the difficulty in determining an unambiguous algorithm to resolve conflicts. The content type manager may provide its own mechanism for context resolution, for example.

In deployment 750, a content item may be a part of multiple content frames. For example, multiple copies of a content item may be loaded by an application if it loads multiple content frames containing the item. Applications may search for and retrieve content frames. For example, content management may load and cache content frames. In certain examples, authoring tools may retrieve content items directly. Running applications may retrieve content frames during execution, for example.

Context may be resolved while constructing a content frame. That is, selection of context variants on which the deployed content item is dependent is done during deployment, for example. Content frames may thus be context specific. During load and retrieve, context may be used to select a content frame, not content items contained in the frame, for example.

A content frame may itself be considered a content item. Thus, the content frame may be versioned, have associated metadata, etc. Since a content frame is a content item, packages of frames may be constructed and distributed content frames without the associated source content items, for example. In certain examples, content frames may contain content frames, allowing courser grained deploy and undeploy operations. In certain examples, optimizations to frame loading (e.g., loading a single copy of a common content item) may be done, if desired, using techniques such as reference counting, etc.

In certain examples, content frames are related to a deployed root content item in a fashion analogous to the relationship between context variants and the content item. For example, a content frame is identified by the same UUID as the root content item in the frame and shares the same directory metadata. Each content frame may have its own unique identifier that may be used as a reference. Each content frame may be context specific and may have multiple versions. In certain examples, only deployed content items have associated content frames. Because of this relationship, content frames may be treated in a directory as properties of a content item along with context variants, for example.

In certain examples, content may be undeployed. An undeploy is a process of a making a (deployed) content frame unavailable to a running instance, for example. However, data instances stored in a CDR may be dependent on the content frames used to create the data instances (e.g., clinical element (CE) types). As a result, a content frame, once deployed, may not be physically deleted from the clinical content system without compromising referential integrity, for example. Undeploy, then, may make a content frame invisible to subsequent searches and context selection. Through undeploy, a previous version of a content frame may then be once again visible to search and context selection, for example. In certain examples, an undeployed content item may still be directly retrieved using the UUID for the content frame.

In certain examples, content item translation refers to modifying a content item during loading and/or retrieval to make the content item responsive to changes in content items on which it is dependent without redeploying the content item. For example, terminology designations and pick-lists may change independently of the deployment of the content item. Content item translation may be a responsibility of a content type manager responsible for a content item. For example, translations that make sense for one content type may not make sense for another content type. Content item translation may be context specific, for example. Content item translations may be performed by inserting custom macros in a content item (e.g., at authoring time) and applying a template tool to execute the macro and perform the translation with the item is retrieved.

Content item translations may be fine-grained. For example, they do not change the structure of the content item but replace elements (e.g., labels, lists of labels, etc.) within the item. Course grained modification of content frames (such as re-resolving content items that the content item being retrieved is dependent upon at retrieval time) may be undesirable because they can lead to unpredictable changes to application appearance or behavior. Hence, these kinds of modification are restricted to occurring at deployment time. In certain examples, common tools may be used to perform translation of content items represented in XML or HTML. Apache's Velocity is used here as an example only. Dependencies for items that depend on translations may be managed by maintaining a content frame dependency on a content frame containing the items to be translated (e.g., a terminology content frame) rather than by maintaining specific dependencies, for example.

Loading 760 is a process of retrieving a content frame containing deployed content item(s) from storage and making the frame available for use by running application(s). Content items in a content frame may be translated during loading. For example, terminology designations may be resolved and/or pick-lists retrieved. A content frame may be cached after loading. Content items contained within a content frame may be loaded as a single operation, for example.

In certain examples, the choice of doing translation at retrieval time or load time is up to the content type manager. Translating at load time means that the cost of translation is amortized over multiple uses of the item; translating at retrieve time means that the item is more sensitive to context variation and changes in resolved content. A selection of translation time may be content type specific, for example.

Retrieving 770 includes fetching a loaded content frame by a consuming application. Content items within the content package may be translated during retrieval (e.g., resolving terminology designations, retrieving pick-lists, etc.). A loaded content package may be retrieved multiple times by different clients, for example. An application may choose to reuse (e.g., cache) a retrieved content package at its discretion. Content items within a content frame may be loaded as a single operation, for example. In certain examples, since a content item may be present in different content packages, different instances of an item may be translated using different context. For example, an application may show a content item in two different languages concurrently for comparison.

A choice of doing translation at retrieval time or load time may be made by the content type manager. Translating at load time means that the cost of translation is amortized over multiple uses of the item. Translating at retrieve time means that the item is more sensitive to context variation and changes in resolved content. A selection of translation time may be content type specific, for example.

Figure 9:
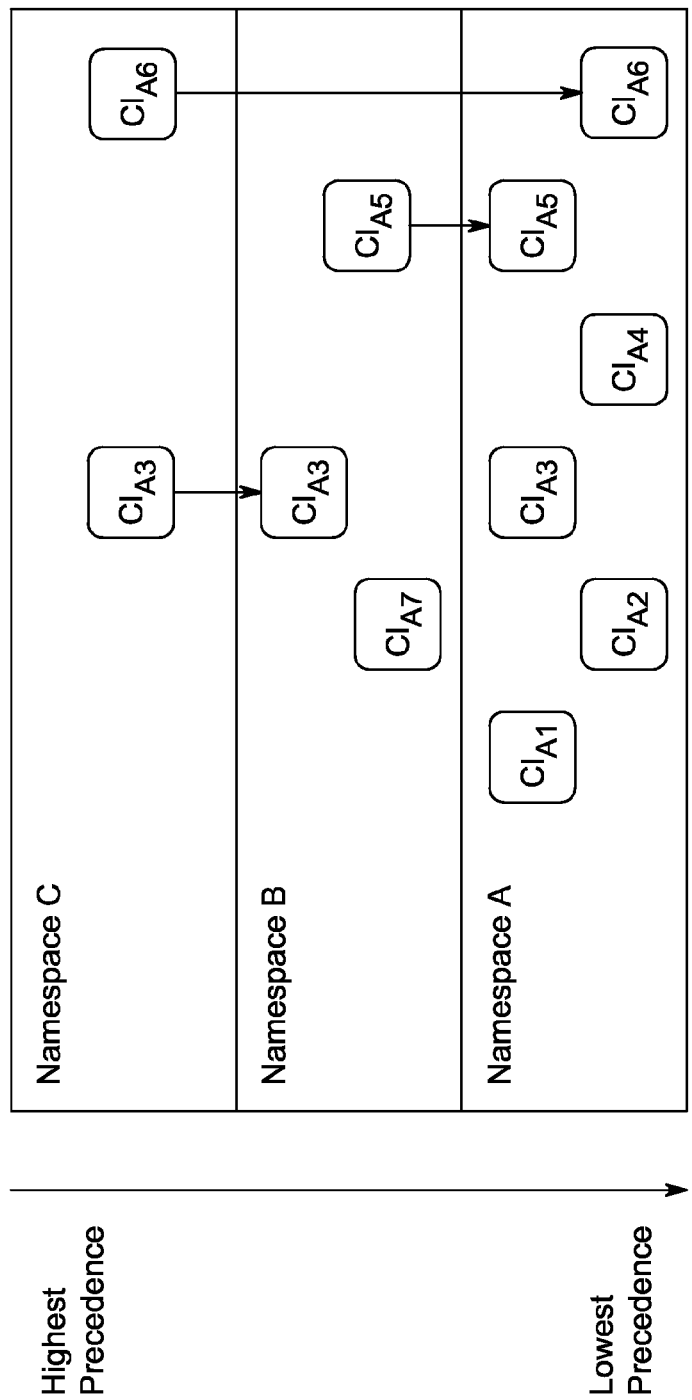
FIG. 9 provides an example of namespaces A, B, and C including various content items (CIs).

In certain examples, content may be divided based on namespace. A namespace is a partition of content items in a system where each partition is owned and managed independently of other partitions. FIG. 9 provides an example of namespaces A, B, and C including various content items (CIs).

Namespaces may be motivated by various factors. For example, content items in one namespace may be protected from modification by another party (for example, a customer modifying GE distributed and owned content). Applying maintenance (e.g., updates, bug fixes, etc.) becomes difficult, if not impossible, if a customer can modify GE distributed content (e.g., customer modified content may potentially be broken when replaced with an update). Alternatively or additionally, for example, customers may be allowed to add and extend distributed content in safe ways while enforcing governance restrictions on such modification (e.g., models may not be modified or extended, but MPVs may).

While some of these restrictions may be enforced by a security system, customers often set security policy, so another mechanism may be used to enforce such restrictions. Additionally, some rules such as inheritance restrictions may not be adequately managed via security policy.

In certain examples, a simplified namespace model provides that each content item in a system may be searched for using a single namespace precedence order. It is possible that different content types may involve different search precedence (e.g., a search path to resolve data models may not be the same as a search path to resolve forms or reference content). Extensions to the model can be made based on circumstances, for example.

In certain examples, namespaces may be "owned" by a provider, a customer institution, a department, etc. Such ownership separates provider content from customer content, for example. Multi-tenancy and digital rights management may be facilitated through the use of namespaces, for example. In certain examples, only the owner of a namespace may create or modify content items within the namespace. An owner may own multiple namespaces, for example. A clinical knowledge platform and/or associated enterprise clinical information system may serve as an owner of a "root" namespace (and possible others), for example. Each customer installation may be an owner of at least one namespace for that customer, for example.

In certain examples, an "owner property" on a content item used as a context attribute is also presented in some contexts as equivalent to a namespace. However, in context resolution, using an owner property there may be no inherent precedence. For example, given a concept with designations potentially owned by A, B, and C, an application asks for the designation owned by A but that designation does not exist. Does the system return designation B or designation C? In general, property precedence in context resolution involves a heuristic to resolve (e.g., weighting and scoring schemes).

Additionally, there may be necessary relationships between content items in namespaces. For example, specialization via inheritance, overriding content items in one namespace with the same item in another, copying an item from one namespace to another (e.g., is it legal to do the copy?), etc. These behaviors may or may not be able to be implemented using an owner property (alone) in the general case.

Additionally, "owner" may be used in at least two different senses: first, as an intellectual property/digital rights management (IP/DRM) concept where it designates actual ownership (e.g., a package by "owner" is a practical application of this concept —package everything that is owned by an owner); second, as an attribute used to select a desired/appropriate context variant when retrieving a content item. This second usage is more directly analogous to namespaces with the caveats above.

In certain examples, a difference between an owner context attribute and a namespace is that namespaces are known to and defined by a system rather than defined independently for each content item in content (e.g., owners are generally terminology content). The system can establish precedence, maintain persistent/immutable relationships between items in different namespaces without expectation that the relationships will change, for example. That is, "namespaces" may be part of a reference implementation; owners are content defined and hence may be interpreted by the reference implementation, for example.

In certain examples, namespaces have "precedence" when searching retrieving, etc. For example, as shown in FIG. 9, a highest precedence namespace C is first searched for a content item, then a second highest (e.g., namespace B), etc. Precedence may be established when configuring the system or defining the name spaces, for example. Precedence may be overridden when deploying a package.

In certain examples, relationships may exist between content items in one namespace and content items in a lower precedence namespace. In certain examples, changing namespace precedence may change the nature of a relationship.

In certain examples, a new content item may be created in a higher precedence namespace by copying an item in a lower precedence namespace. For example, an MPV may be copied from base content, modified, and saved as a user-owned MPV. A content item may be created in a higher precedence namespace that hides or replaces the same content item in a lower precedence namespace, for example. For example, a new version of a formlet that hides the same formlet in base GE Qualibria® content to customize display of that formlet. Creating a new content item that specializes (e.g., inherits from) an existing content item may hide or replace a base content item in a lower precedence namespace. For example, a new attribute may be added to a patient clinical element model provided by Qualibria by specializing the Qualibria patient model.

In certain examples, namespace relationships are managed by a content management system. If a base content item is modified, a specialized content item may need to be redeployed. In certain examples, specialization of a content item in a namespace may be allowed in another namespace but copying the content item may not be allowed. State changes in a base content item may involve state changes in a specialized content item (e.g., if the base item is deprecated, the specialized item may also require deprecation), for example. In certain examples, digital rights management may prevent a copy of a content item from being created. In certain examples, if a content item that was copied to a new namespace is modified, an owner of the target namespace may need to be notified of the change so the copy can be reviewed for changes.

In certain examples, an owner attribute on a content item may be insufficient to manage namespace relationships. Clinical element models (CEMs) are an example of a relationship restriction: copying and hiding a CEM can lead to data inconsistencies while specialization through restriction or extension can be safely done. Hiding an MPV on the other hand, is generally a safe operation, for example. In certain examples, relationship management/enforcement is a responsibility of a content type manager (CTM), or at least the CTM should be able to specialize system relationship management.

Namespaces may be used in a variety of stages of a process. For example, namespaces may be used during authoring. For example, namespaces may be used when resolving context variants, establishing relationships such as copy, copy and hide, etc. Namespaces may be used during packaging, for example. A package may include content items from a single namespace, for example. Context variants, relationships, etc., in other namespaces involve dependencies on packages in those namespaces, for example. Namespaces may be used during deployment (e.g., when resolving context variants, when establishing relationships such as inheritance relationships, etc.), for example. In certain examples, namespaces are not used during load and retrieve at runtime.

In certain examples, each context variant of a content item has a current "state". For example, a state may include deployable, deployed, loaded, deprecated, etc. Each content type has a set of allowable states and a set of allowable state transitions represented as a state machine. Content types may have different state machines in an authoring environment than in a runtime environment, for example. State machines may be owned by a content type manager since the manager defines a meaning of each state for a content type.

In certain examples, a state in a runtime system is actually the state of the content frame. However, for simplicity, a state of the content frame is assumed to be (and managed as) the state of the root content item. A state of content items included via dependency resolution may be irrelevant to the runtime system (e.g., it may be required that the root content item of the content frame be redeployed to bubble up state changes in that item).

In certain examples, lifecycle management refers to a set of workflows that manage transition of a content item from one state to another. Each state in a content type state machine is associated with a distinct workflow that manages the content item when in that state, for example. In certain examples, workflows are content items to allow variation across implementations.

Figure 10:
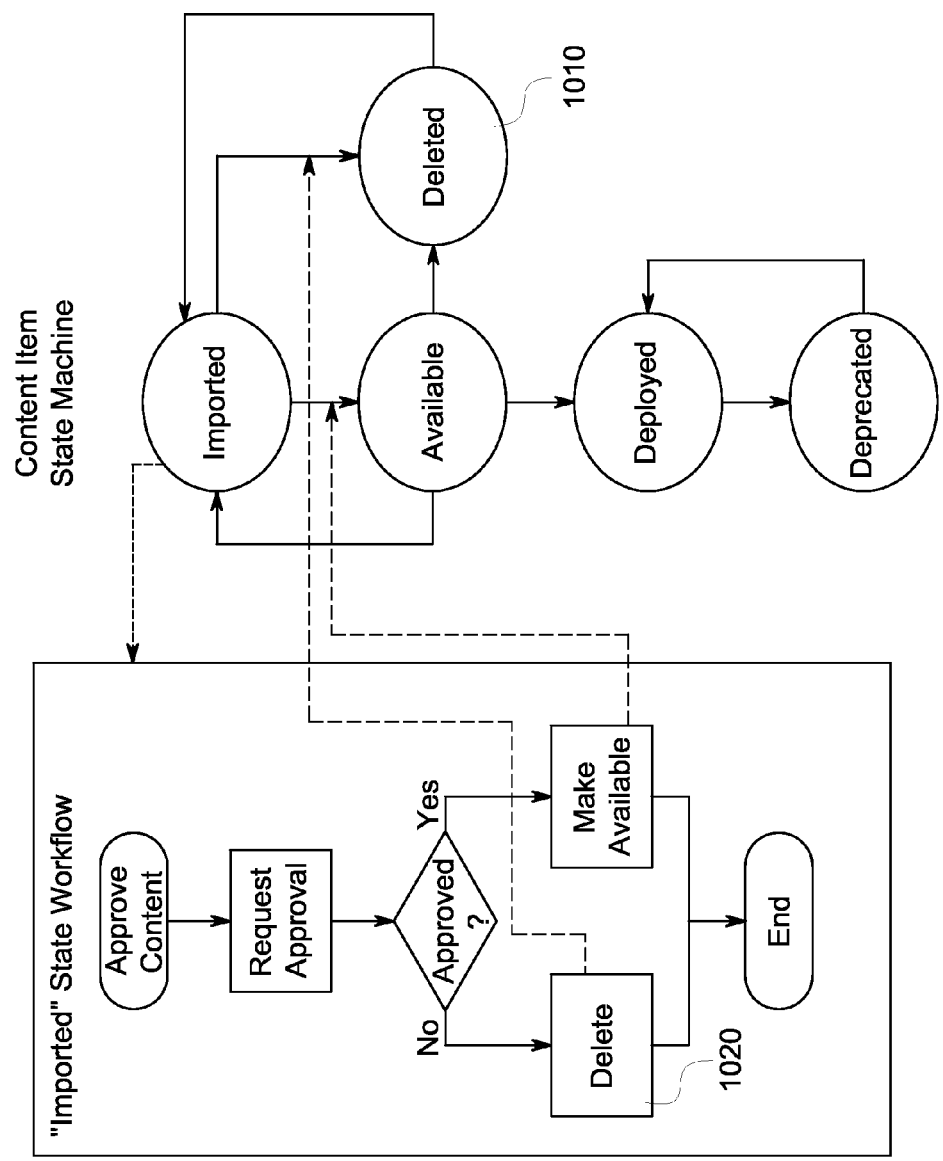
FIG. 10 depicts an example of a state versus a workflow.
Figure 11A:
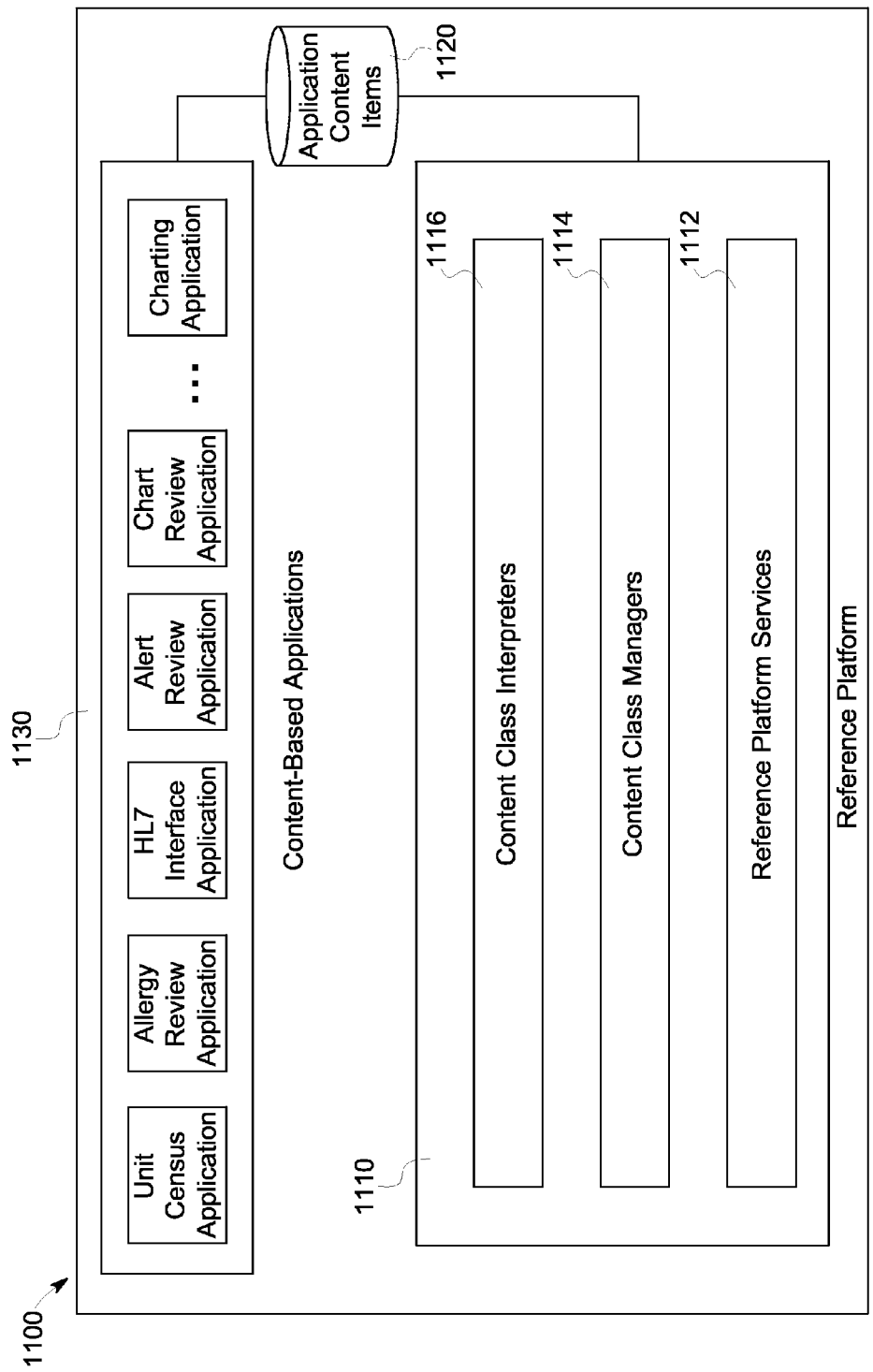
FIG. 11 illustrates an example clinical information system including a reference platform and one or more content items that define clinical functionality.
Figure 11B:
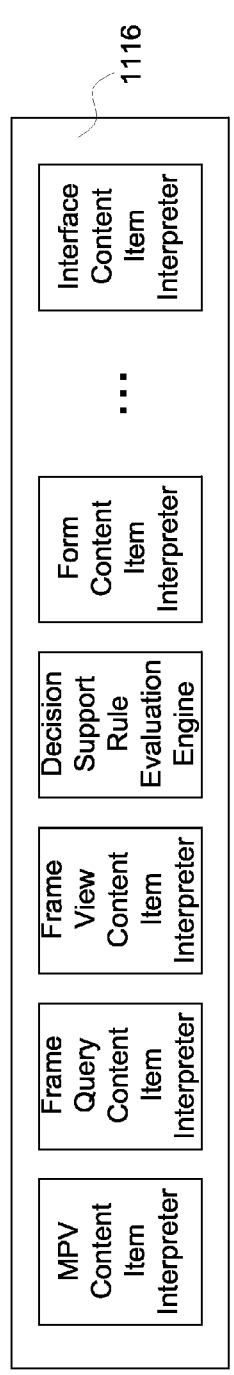
Figure 11C:
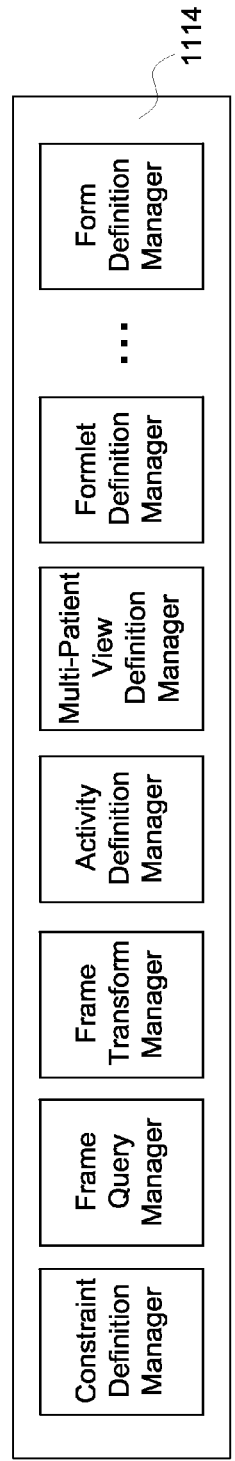
Figure 11D:
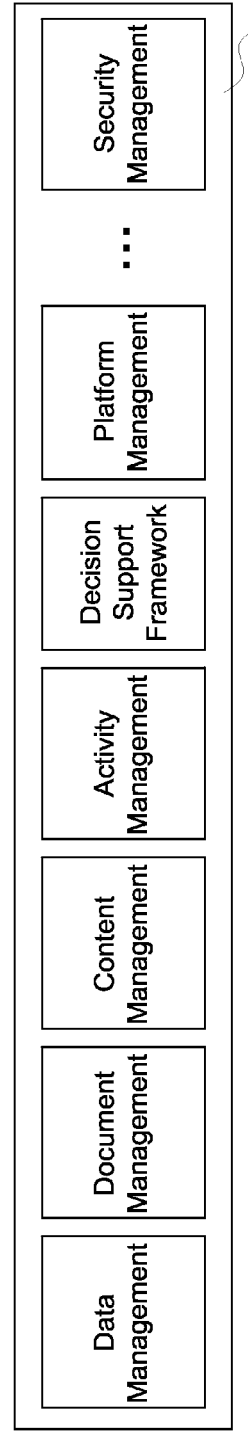

FIG. 10 depicts an example of a state versus a workflow. As shown in the example of FIG. 10, each state in a content item state machine 1010 has an associated workflow 1020 that controls transition(s) to the next state(s).

In certain examples, governance refers to a set of policies that manage lifecycles of each content type. Governance policies are implemented in state machines and associated workflows of a content type, for example. Governance may be an operational function, for example.

Certain examples provide a content-based clinical information system including a stable reference platform that defines and executes the core capabilities of the system and a set (e.g., one to many) of content classes (e.g., content based languages) that are implemented upon the reference platform and that independently define clinical information functions. The content classes are specialized to allow implementation of narrowly defined clinical functions, for example, Defined clinical functions can include data definition, data query, data transformation, data display, data entry, decision support rules, etc., for example.

In certain examples, clinical applications are created by composing one or more content items (e.g., instances of a content class) from one or more content classes. Each content item is authored or created independent from the creation of the reference platform. Content items and the reference platform can have independent life-cycles and evolve independently over time, for example. Since content classes are independent, support for additional content classes can be added as an update to the reference platform to extend core system capabilities, for example.

Certain examples provide content and data, along with executable software or code. In certain example, content includes data and expressions/instructions concerning data. However, neither data nor content is "software" as the term software is traditionally defined. In certain examples, content is stored in a content database and is independent of hard-coded libraries. Thus, clinicians do not need a new installation of software to change an application, such as a multi-patient view (MPV) dashboard. Other dashboard views can include a rapid recovery dashboard, a hospital-acquired infections dashboard, etc. Content can be configured by a clinician, technician, and/or other user at a location without the platform provider's intervention. Clinicians can author new MPVs on the fly, for example. In certain examples, content can be used to facilitate a query for data by a user and/or application.

FIG. 11 illustrates an example clinical information system 1100 including a reference platform 1110 and one or more content items 1120 that define clinical functionality (e.g., content-based applications). The example content-based clinical information system 100 of FIG. 11 includes a reference platform 1110 having three major layers 1112, 1114, 1116.

In the example system 1100 of FIG. 11, Reference Platform Services 1112 provide foundation services to implement content class managers and interpreters. The reference platform services 1112 are constructed using standard software development techniques and can be modified independent of content items implementing application functionality to enhance available system functionality without impacting the application functionality, for example.

In the example system 1100 of FIG. 11, a Content Class Managers layer 1114 implements management services for one or more content classes. A content class includes defined (e.g., a narrowly defined) domain specific language that allows clinical personnel to define custom programmatic elements (e.g., content items) that will be used when composing a clinical application (for example, clinical vocabulary concepts, clinical data models, data queries, data transformations, display forms, etc.). An example Content Class Manager provides capability(-ies) to author content items of that content class. The example content class manager provides capability(-ies) to package those content items for distribution, export and import the content items from and to installations of the clinical information system, and deploy the content items to a running clinical information system (e.g., compile, translate, etc., the content item into an executable form). The example content class manager provides capability(-ies) to load the content items into memory while performing context-based translation of the content item (e.g., resolve terminology designations, pick-lists, etc.), and to retrieve the content items for execution in an associated content class interpreter. While a running clinical application can include content items of different content classes, each content item is independently managed by the content class manager associated with the content item.

In the example system 1100 of FIG. 11, a Content Class Interpreter layer 1116 defines one or more interpreters (e.g., programs that consume a content item and execute the instructions defined in the content item) for content items of each content class. Since an application is a composition of content items, multiple content class interpreters can participate in the execution of the composed application(s). Content class interpreters consume a deployed (e.g., executable) form of the content item(s). Optimizations and/or other improvements to performance of a content item interpreter can be implemented in conjunction with a content class manager, for example.

Content Based Applications are composed of one or more content items that are managed by content class managers and executed by content class interpreters. A set of content items of which an application is composed are stored in a content repository and managed as a set of interdependent items. Content based applications are independent of the reference platform; that is content based applications can be changed without changes to the reference platform, and the reference platform may be changed without changes to the content based applications (though content based applications may be changed to take advantage of new capabilities in the reference platform), for example.

Since medical practices vary widely between different institutions (and even within institutions or between patients) and change rapidly as medical practices evolve, prior clinical information systems require extensive customization to be deployed widely. Very frequently, this degree of customization can render ongoing maintenance (e.g., new releases, error fixes, etc.) difficult or even impossible. Additionally, responsiveness to requests for customizations may be unacceptable to the institutions because of the difficulty in creating, testing, distributing, and managing the customizations.

Two common approaches to these issues may be found in existing products. First, the producer of the system tightly controls the software system and controls/restricts the changes that can be made to the system, thereby severely restricting the ability of the software to be customized to specific customer needs. Second, the producer of the system may allow extensive customization of the software wherein each implementation becomes essentially a custom system which limits the maintainability of the system.

Certain examples address these problems by separating the application, where customization generally occurs, from the system itself, where maintenance generally occurs. An example clinical information system application is implemented in content, that is, as a set of content items that are created and maintained independently of the system, often by the customers of the system themselves. The reference platform (e.g., the system) is maintained, enhanced, tested, and deployed by a vendor. Since the application (in content) is independent of the reference platform, the two can evolve largely independent of each other. Independent evolution allows a much greater degree of possible customization without reducing the maintainability of the system, for example.

Rather than basing content on a single general-purpose interpreted language, certain examples implement a content based system as a set of content languages. In certain examples, each content language is narrowly focused and specialized to allow independent evolution, optimization, etc.

In certain examples, by separating applications from a reference implementation, independent evolution of the application and the system can be supported. In certain examples, application(s) can be authored by domain specialists rather than by engineering. For example, terminology and data can be modeled by informaticists; clinical forms can be designed by clinical teams; etc. In certain examples, functionality can be added to the system incrementally by adding new content classes to the system. Since content classes are narrowly focused for specific tasks, a risk of over-generalization is reduced or avoided, for example. Content classes can be independently evolved and improved/optimized, for example.

In certain examples, clinical content includes structured knowledge components such as decision support rules, protocols, reports, user preferences (e.g., triage form layout, patient and/or department worklist format, etc.), and unstructured knowledge components such as discharge instructions, guidelines, etc. Clinical information systems (CIS) that are content-driven provide functionality that improves clinical outcomes by enhancing compliance with institutionally/nationally recognized standards of care and reduce practice variation. In certain examples, a new process has been defined to streamline clinical content management from its inception to its consumption by the CIS.

The example process allows for building of an infrastructure for managing clinical content in a more efficient and more optimal manner. Using this clinical content management process, clinical content management is scalable and expressive, for example. When a CIS is introduced into a new environment, lack of a standard process interferes with resource planning, effort planning and estimating timelines, for example. An example clinical content management infrastructure built around this process can help with the implementation effort by identifying appropriate dependencies, breakdown tasks along with their associated resources, and help align priorities.

In an example, a small client is interested in going live with a couple of clinical modules (e.g., a discharge module and a billing module). As part of these modules, using the example content-driven process, structured and unstructured clinical content can be authored, versioned, packaged, and tracked to ensure compatibility with future updates. Building on the example use case, if the client wants to add its own local content, plug-n-play packagers and deployers are provided that are applicable only to these two modules. If the client is happy with the two example modules and wants to go live with additional modules, the infrastructure built around the process can scale up to identify potential clinical content interdependencies, help eliminate redundancies, and bridge clinical application versions and clinical content versions, for example.

In certain examples, the clinical content management infrastructure can be integrated into a software lifecycle to eliminate separate iterations and planning exercises. Integration can produce significant savings in planning, effort, and execution time, for example.

In certain examples, during the content authoring and packaging processes, the infrastructure verifies and validates dependencies and helps ensure content integrity, for example. The infrastructure eases the process of versioning at the content and package level.

In certain examples, future updates can be automatically packaged as patches that can be released internally and/or externally to clients on a pre-determined schedule. Patch releases can still maintain content integrity that can be described through a conformance statement, for example.

In contrast, prior enterprise clinical information systems rely on ad-hoc processes for clinical content management, wherein processes are manually created on the fly by programmers on a case-by-case basis. Some significant impediments to the adoption of standards and coded content (e.g., structured/unstructured) in clinical information systems are high costs associated with clinical content authoring. In addition, prior techniques resulted in uncertainty in managing dependencies between content types, and uncertainty in creating predictable release cycles.

Thus, certain examples provide a clinical content management process that is scalable, expressive, and semantically interoperable. For example, the process is scalable in that it can support core content as determined by an application's needs in addition to customer/competitor specific content. For example, the process allows end users to consume content to support individual preferences at an enterprise level. For example, the process provides an infrastructure for clinical entities to create semantically interoperable systems to derive clinical, research and business benefits thereof.

From a business standpoint, the example process enables modular content packages and pluggable deployment. This flexibility allows tailorable content to support different types of clients to augment a "surround and supplement" strategy, where-in a small client with limited budget can go live with only couple of modules/content-deployers, whereas a large enterprise customer might want a whole suite of content management infrastructure.

Certain examples define processes apriori to help ensure that structured and unstructured clinical content development and management is more predictable, measurable, efficient, and integrated into application lifecycle management. Current systems and/or processes for managing clinical content in content-driven systems are fraught with uncertainties such as in version compatibility, quality control, timely packaging and delivery of content, updating knowledge bases, and smart deployment.

Building a clinical application on an infrastructure as described herein provides significant benefits to a content management process such as making it scalable, expressive, supportive of standard(s), semantically interoperable, and flexible.

In certain examples, content and infrastructure can be used to map or resolve concept identifiers into human-readable designations using a terminology.

Typically, when a computer system is designed for an industry or application, the system is designed to meet the needs for the most customers in the industry as possible. Sometimes different customers want to use the system in different ways. This can be solved by making systems that are configurable. There are cases were different individual users or departments want their own configurations or preferences. This invention improves the way a system stores and manages these preferences.

Some industries have adapted the way they do business to fit the computer system purchased. A distribution center might change the way it fills orders in order to fit the way the computer software wants it tracked. This does not work with clinical information systems. Different hospitals vary greatly in how they provide health care and how they use their information systems. Different doctors also do things differently. It may be simple to train a store clerk the new way to fill orders, but it is difficult to ask a doctor to change the way they do things. It is not reasonable for a health network to adapt to its chosen software, so the software needs to adapt to the particular health network, region, hospital, department, and care provider.

One example of how a clinical information system might be configured is a patient admission screen. The software for the clinical information system includes an admission screen for new patients. The admission screen includes a form associated with a workflow directing which information to collect and when to collect it. The admission screen may also display other information about the patient or hospital to assist the care provider during the admission process. While the system includes an admission screen that works well for many hospitals, it will not have everything needed for every situation.

Different hospital networks may want to change the admission process to be different from the one that is included by default with the software. In those cases, they will want to modify the admission process to fit the needs of their network. Within the hospital network, there may be a region that needs to modify their admission process. Within that region, there may be a hospital that needs to add a step in the admission process specific to that hospital. There may even be a care provider who wishes to modify the way the admission form is laid out to fit a user specific need.

These modifications are based on a context. The region, hospital, language, and user all help to define the context for the particular admission process. The context is based on a hierarchy where the hospital depends on what regions it is in, and the user depends on what hospital it is in. For example, a user might customize their layout of the admission form one way when they are working at one hospital. It might need to be customized another way at a different hospital.

Traditionally, preferences are stored in a separate data store or stored locally on a client workstation. The system retrieves the content and preferences separately, and then the system alters the content based on the preference. This requires the consumer of the content to be aware of the preference system and also requires the consumer to alter the content.

An example of a traditional preference application is an admissions screen for collecting new patient information. The system may want to allow users to choose if the form was displayed vertically or horizontally. The form itself could be saved as content in a content repository. The system could save the preference, vertical or horizontal, in the preference storage. The application would need to retrieve the form, and then it would need to read the preference for the user and modify the form to appear the way the preference indicated. This requires the application to be programmed in a way that it knows what all the possible preference are, and it would have to know how to modify the form to fit those preferences at runtime.

In certain examples, a clinical information system provides functionality for users to define what the preferences are based on each hierarchical context as needed or desired. The CIS should then provide a correct admission process for the context that exists at admission time. Certain examples provide an intelligent, preference-based content system capable of storing hierarchical-based preferences.

Certain examples store content for each preference separately. A consumer passes in a context when requesting content, and the content for those preference(s) is returned. There is no need for the consumer to analyze the preferences or alter the content. In the patient admission example, an admission form is stored as content to be used by default in the application. If a care provider prefers to change the admission form, the user specifies the desired change, and the system stores that form as content in the content system. The new content is stored with context information that includes the specific user. When the system retrieves the admission form, the system identifies that the context includes the specific user, and the content for that user is used. The content storage is aware of the context, but the consumer did not need to know what the preference was and did not need to alter the content.

Language provides another example of how a preference can be stored as content. A patient discharge form can be stored by default in English. In a bilingual hospital, care providers may speak two languages, but a patient may only speak one language or the other. A second discharge form can be stored as content with a context indicating that it is in a second language different from a first language (e.g., a discharge form in Spanish and a discharge form in English). The patient's language is included as part of the context when retrieving the discharge form from the intelligent, preference-based content system. The application then displays the correct discharge form.

In certain examples, by storing preferences as content, preferences do not need a separate data store. Preferences can be assigned that are user and/or patient specific. Preferences are stored as content, so a consumer of the content does not need to have a knowledge of the preference system. Preferences can follow a user across workstations and/or be centrally managed, for example.

In certain examples, the system and associated software is flexible and configurable by end users. The flexibility and configurability should improve adoption by and usefulness for clinicians, for example. Context-based preference configuration and storage can be provided as part of an enterprise clinical information system, such as GE's Qualibria® system, for example.

Certain examples resolve multiple variants of a content item based on who, what, and/or where the content consumer is. This allows consumers to create, specialize, and/or customize their own content on top of vendor-released content (e.g., shareable and interoperable content). This allows for a single content type to vary by properties associated with the content consumer without the need to customize every application that consumes that content to be aware of the rules necessary to vary the display of the content.

In clinical applications, there are often times that information and data are to be displayed in different ways based on a context of application use. A role of a clinician may impact what clinical information he or she wants and/or needs to see and how he/she wants or needs to see it. A location of a user may also impact a type of information that is desired to be displayed based on clinical need, preference, etc. Clinical information may also be displayed in one or more languages, especially for patients.

Resolution of context by an application allows appropriate information to be displayed based on who, what, and/or where the user of the application is. This ability enables streamlined workflows and targeted documentation for clinical use. This also gives flexibility to customize content for specific use(s).

Previous attempts have included multiple modules in an application that are developed for a specific role or location, thus allowing customers to configure and/or copy parts of an application in order to meet specific context needs. This requires that all applications that use this content also use this code, thus forcing re-deployment of the application. Also, externally developed applications would not be able to take advantage of the rules applied to the context resolution. Thus, a single content item could be created that hides or shows parts based on parameters passed in. This would require complex algorithms during display to parse the content and modify it based on parameters. It would also have to be duplicated everywhere the content was used. Another option is to provide different content items without context resolution and have the consuming application select the correct content item based on algorithms developed per application. Alternatively, a heuristic rules engine could be implemented that would preclude the need for a context resolution algorithm as you could have several separate content items and have the rules engine determine which item would be appropriate to return.

Figure 12:
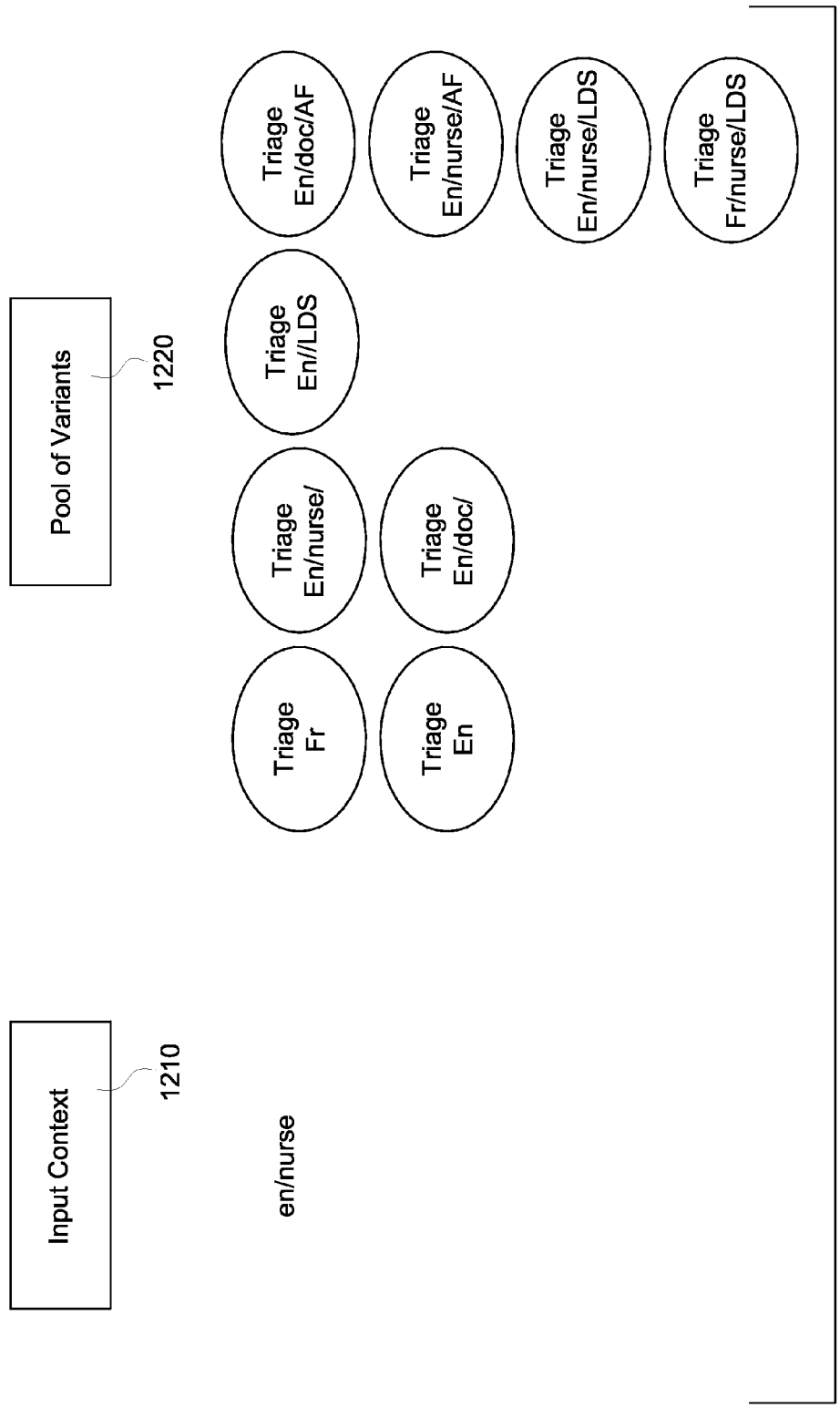
FIG. 12 illustrates an example of runtime context resolution using an input context and a pool of variants.
Figure 13:
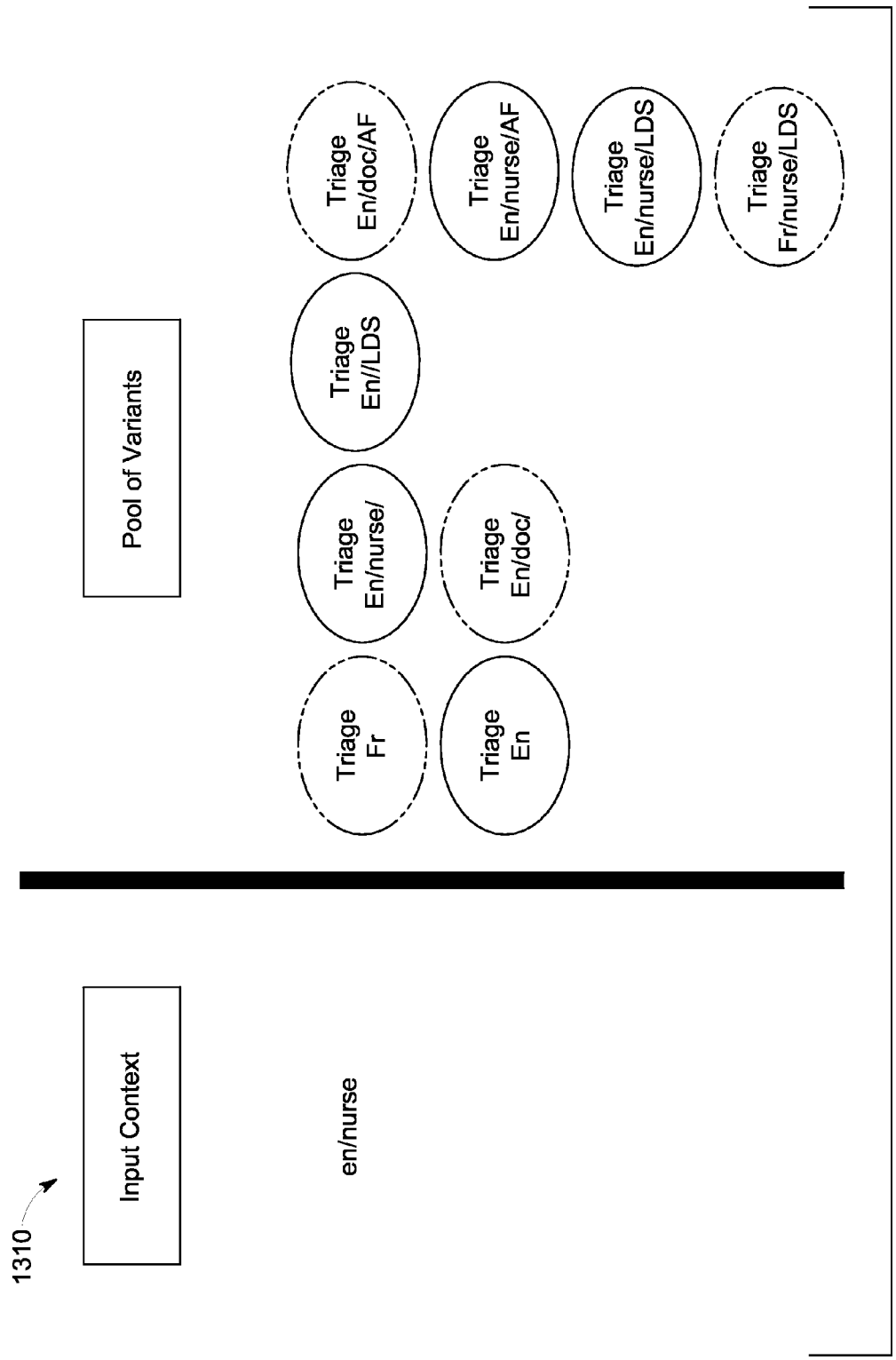
FIG. 13 shows an example in which conflicting variants are rejected.
Figure 14:
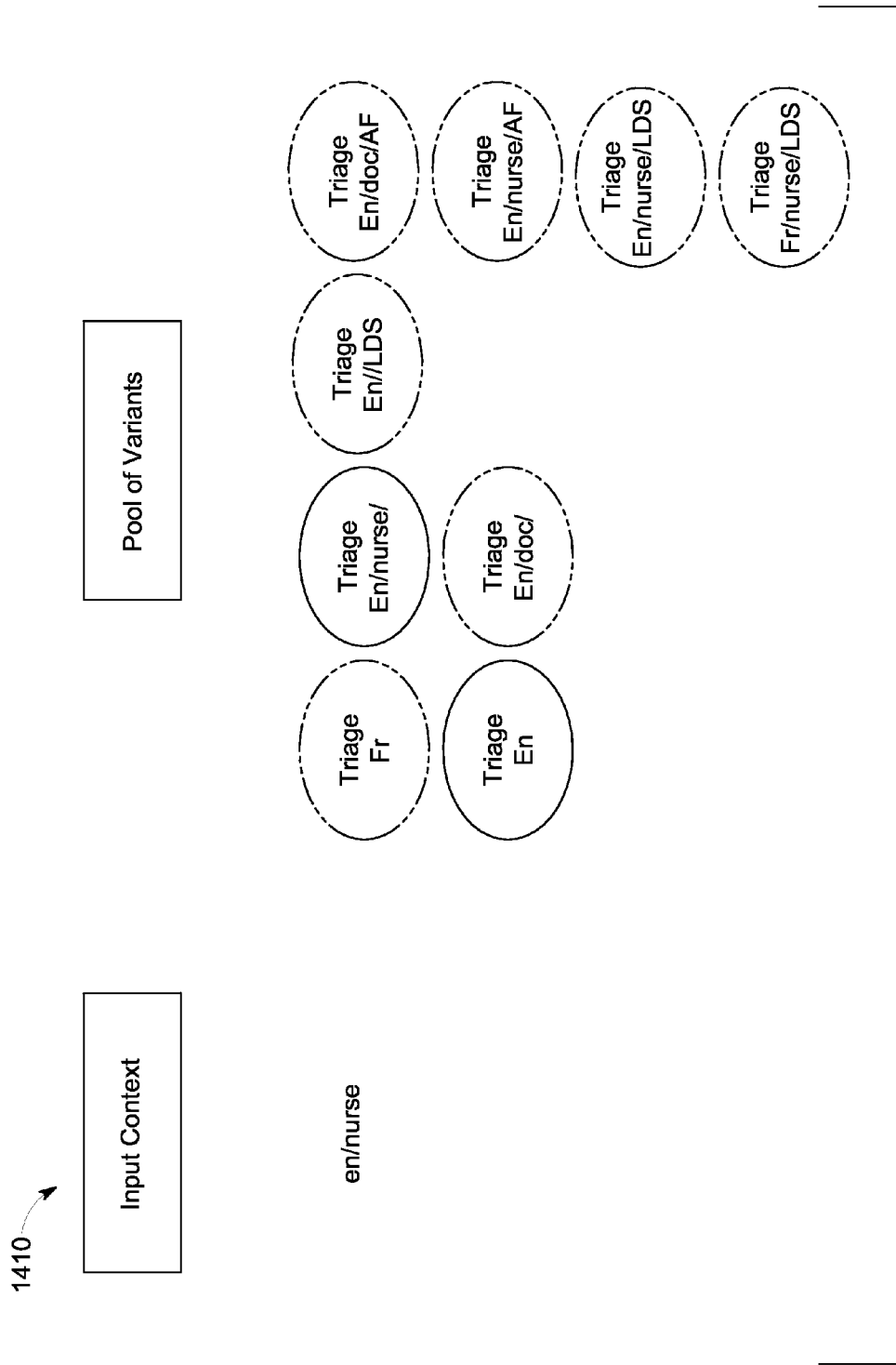
FIG. 14 shows an example in which more specific context variants are rejected.
Figure 15:
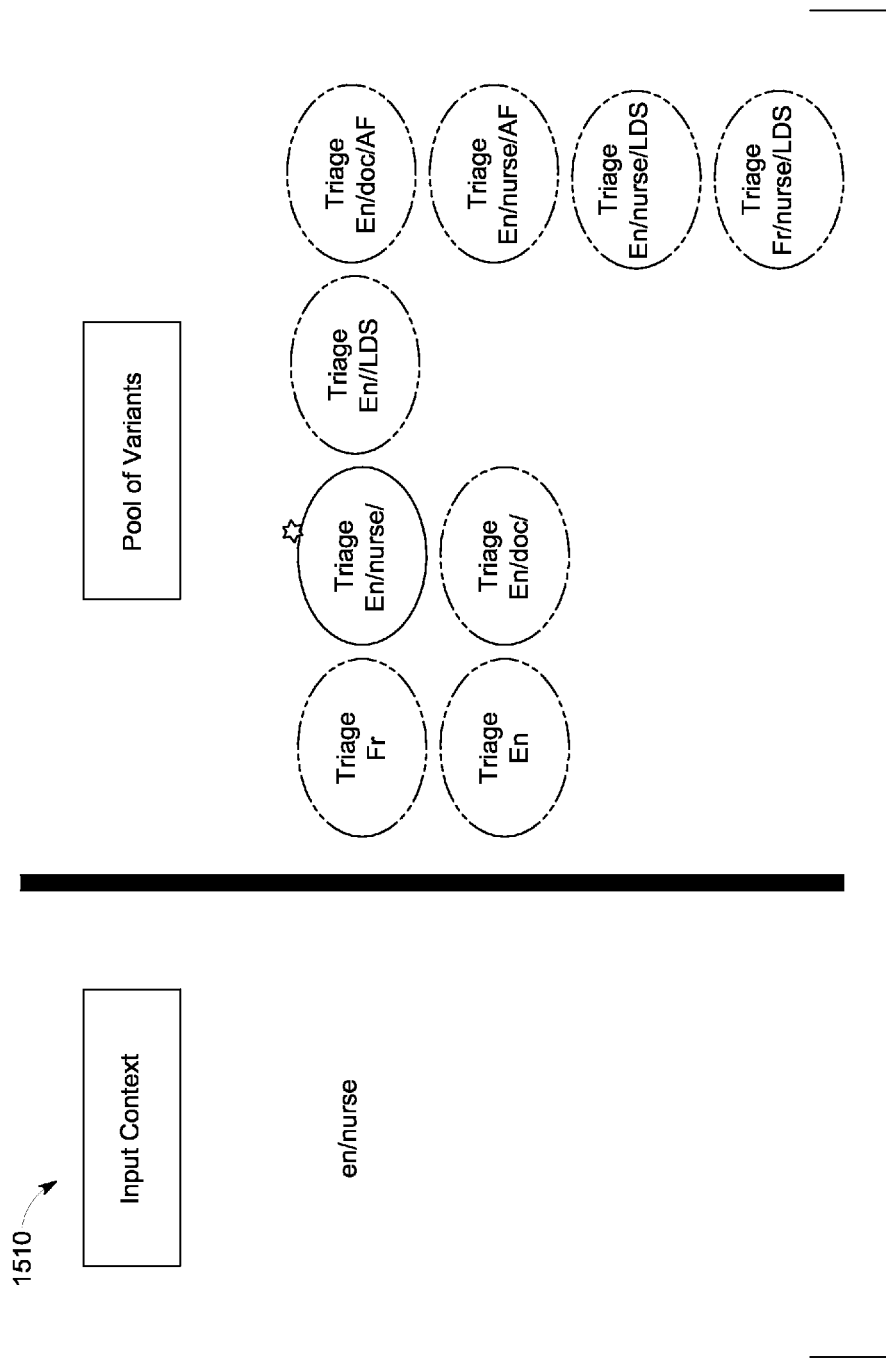
FIG. 15 shows an example in which, of remaining variants, a most specific variant to an input context is accepted to resolve the input context into a context variant.
Figure 16:
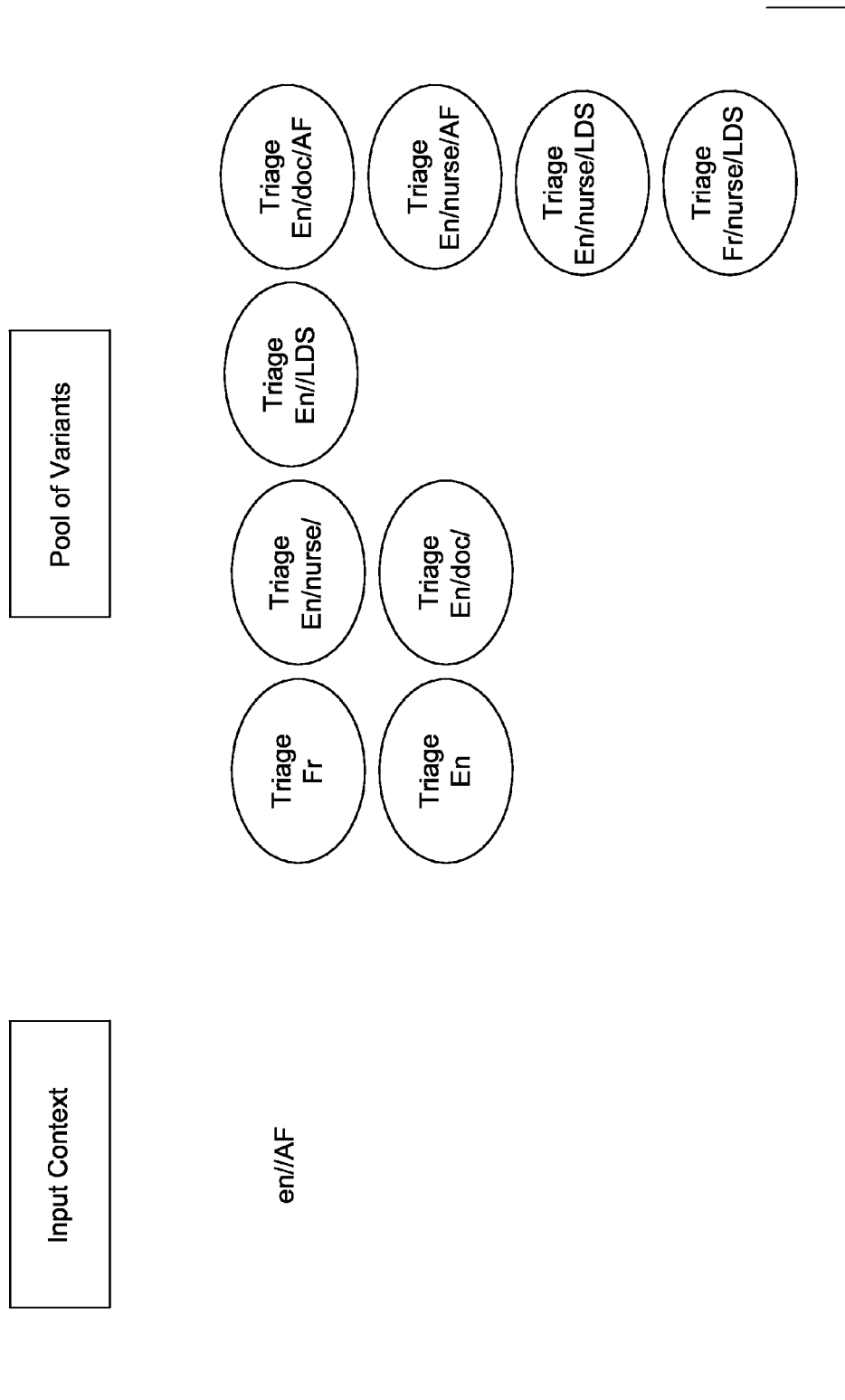
FIGS. 16-18 provide examples of runtime context resolution.
Figure 17:
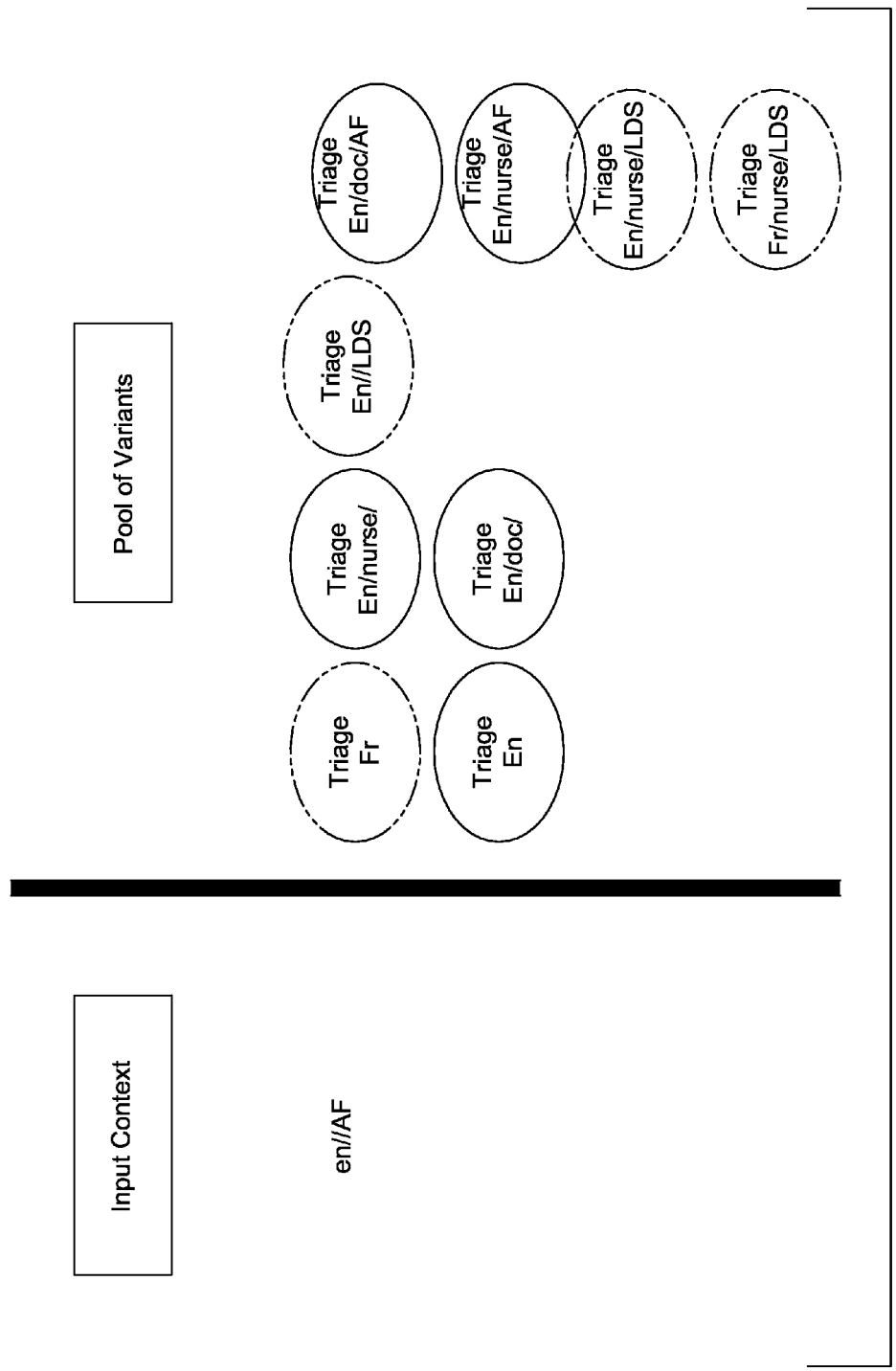
Figure 18:
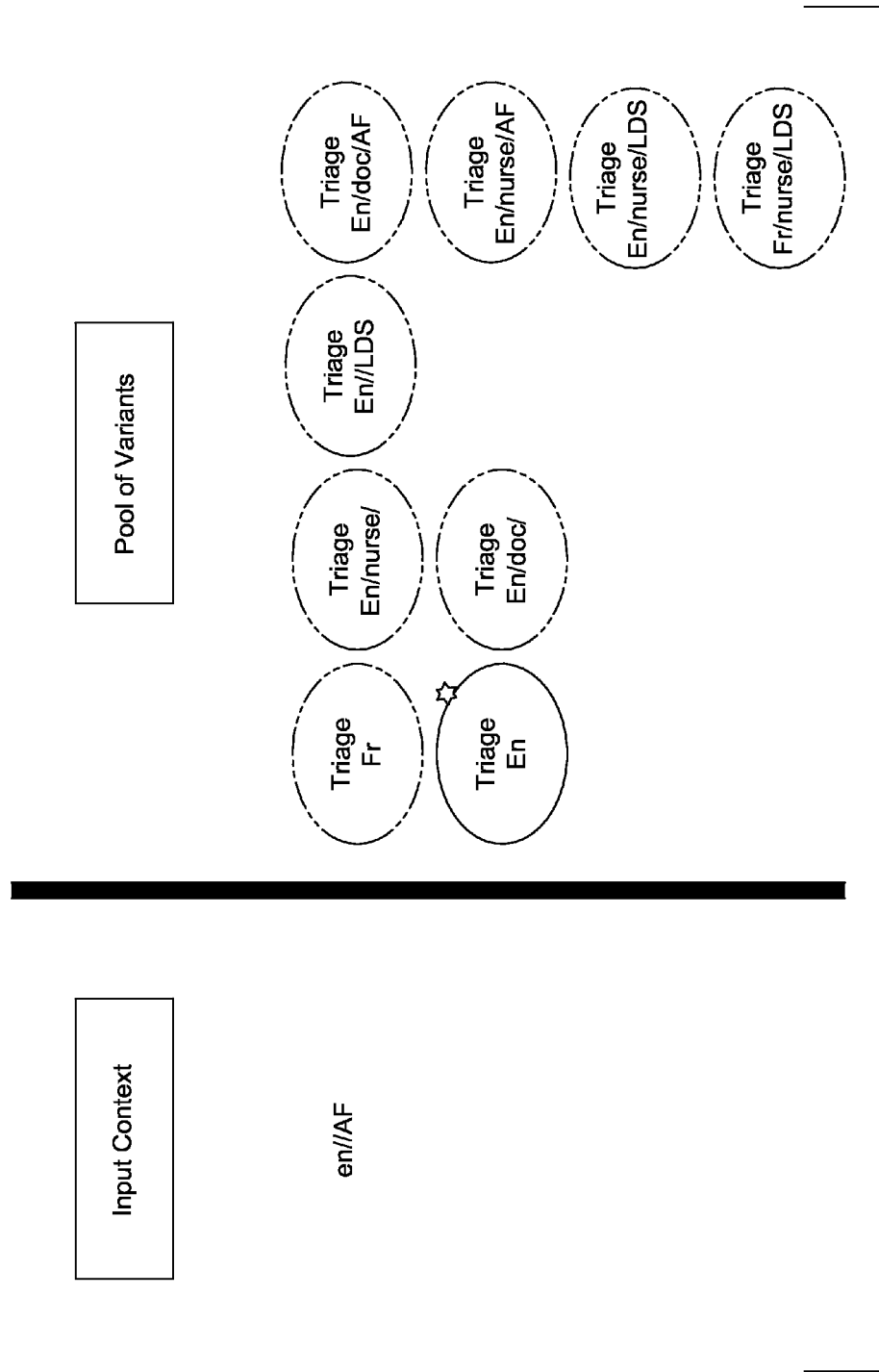

FIG. 12 illustrates an example of runtime context resolution using an input context 1210 and a pool of variants 1220. As shown in the example of FIG. 13, at 1310, conflicting variants are rejected. As shown in the example of FIG. 14, at 1410, more specific context variants are rejected. As shown in the example of FIG. 15, at 1510, of the remaining variants, a most specific variant to the input context is accepted to resolve the input context into a context variant. FIGS. 16-18 provide another example of runtime context resolution by, first, rejecting conflicting variants; next, rejecting more specific context variants; and then, accepting a most specific of the remaining variants for the input context.

Figure 19:
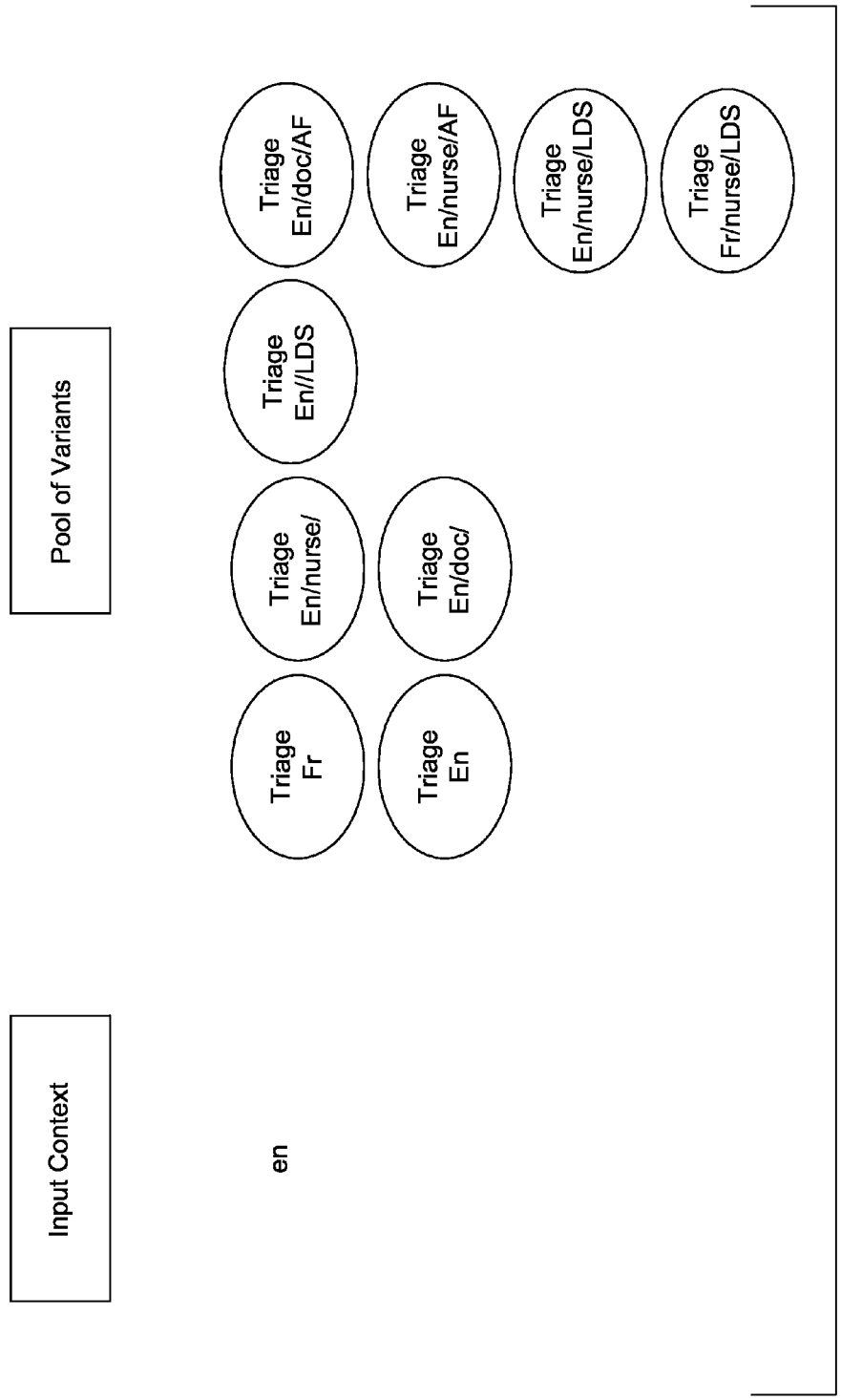
FIG. 19 illustrates an example in which context resolution may occur at packaging time.
Figure 20:
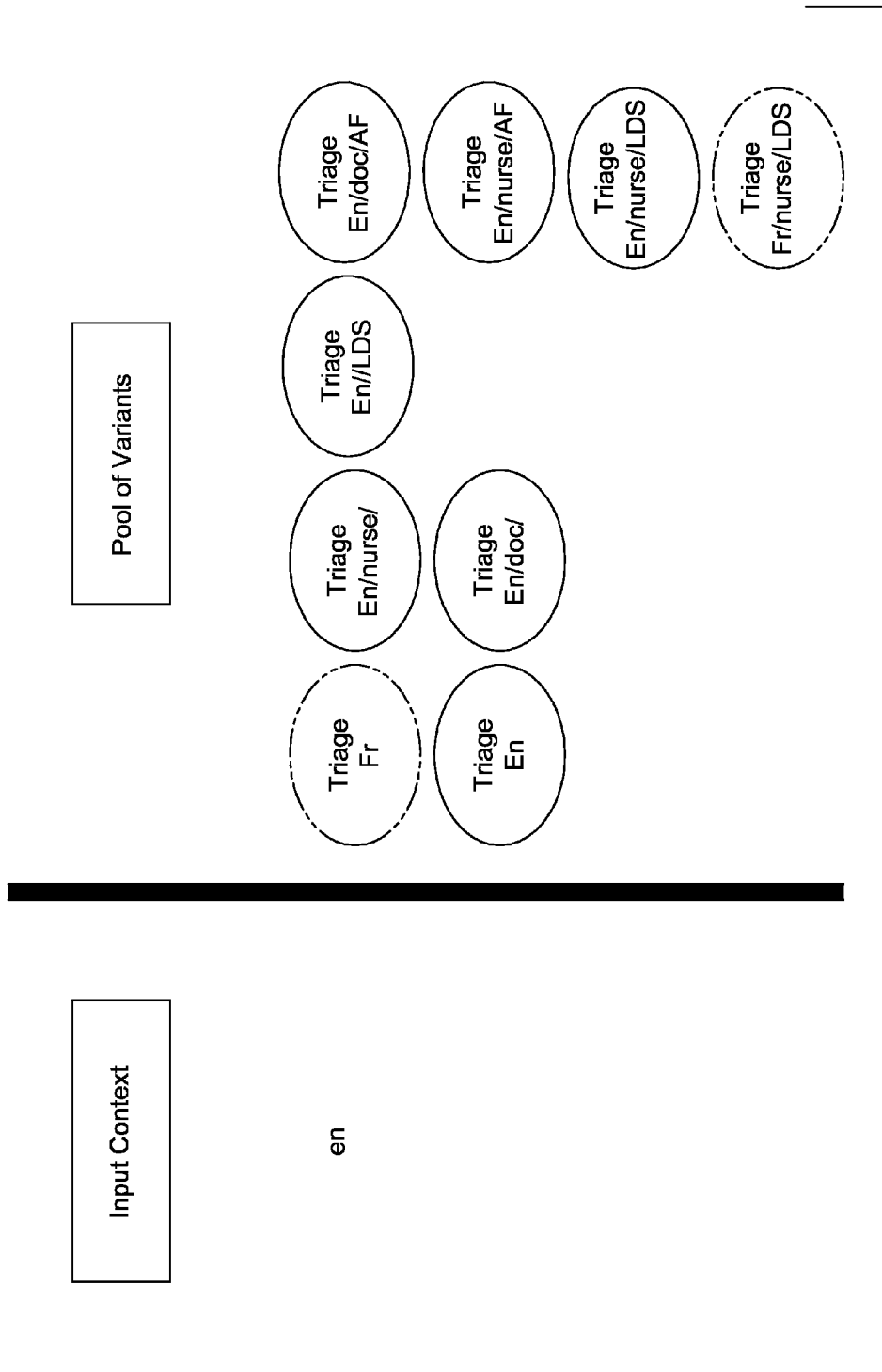
FIG. 20 illustrates an example in which conflicting context variants are rejected.
Figure 21:
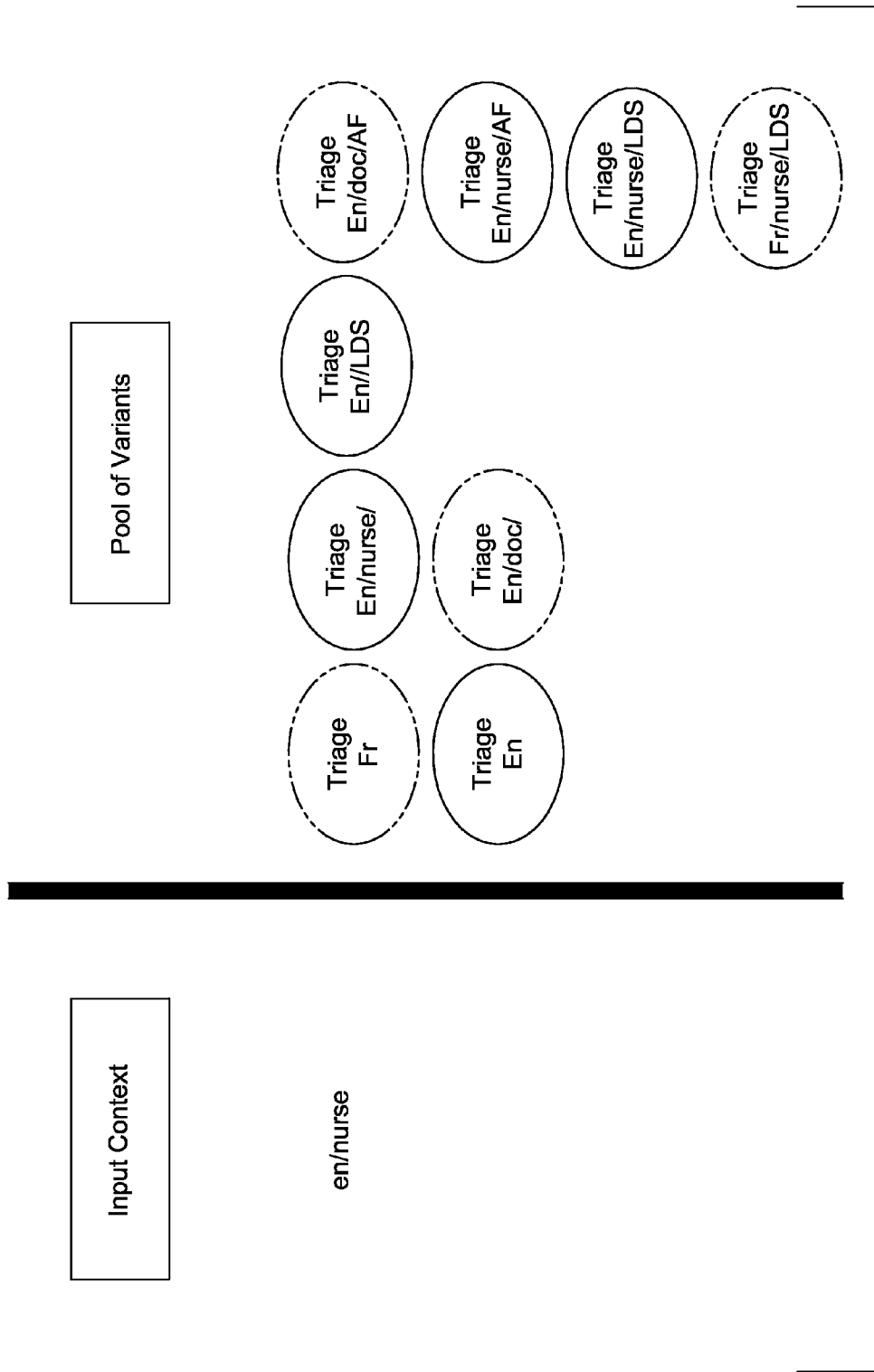
FIG. 21 shows conflicting context variants that may be further eliminated based on an input context at packaging time.
Figure 22A:
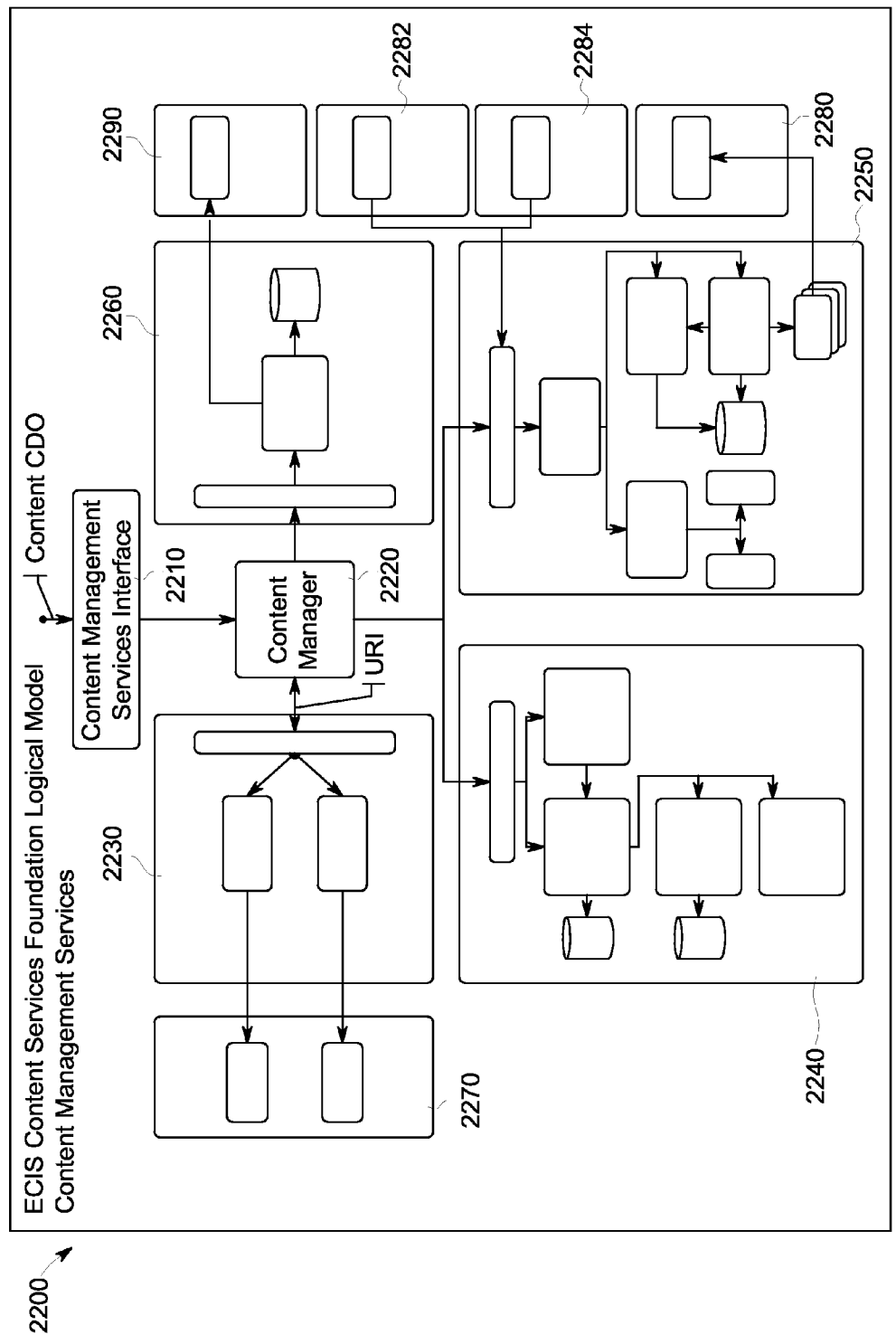
FIGS. 22-23 illustrate example content management services systems.
Figure 22C:
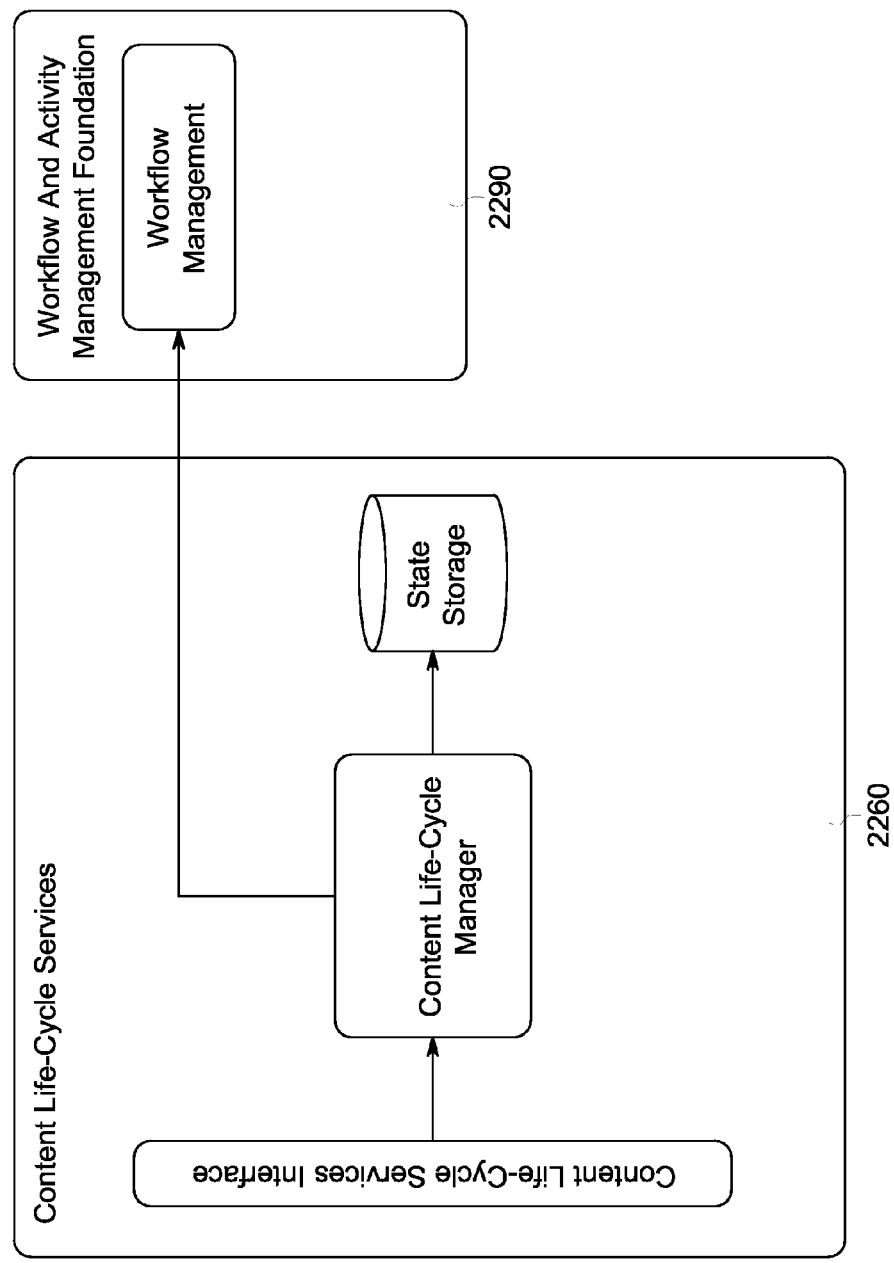
Figure 22D:
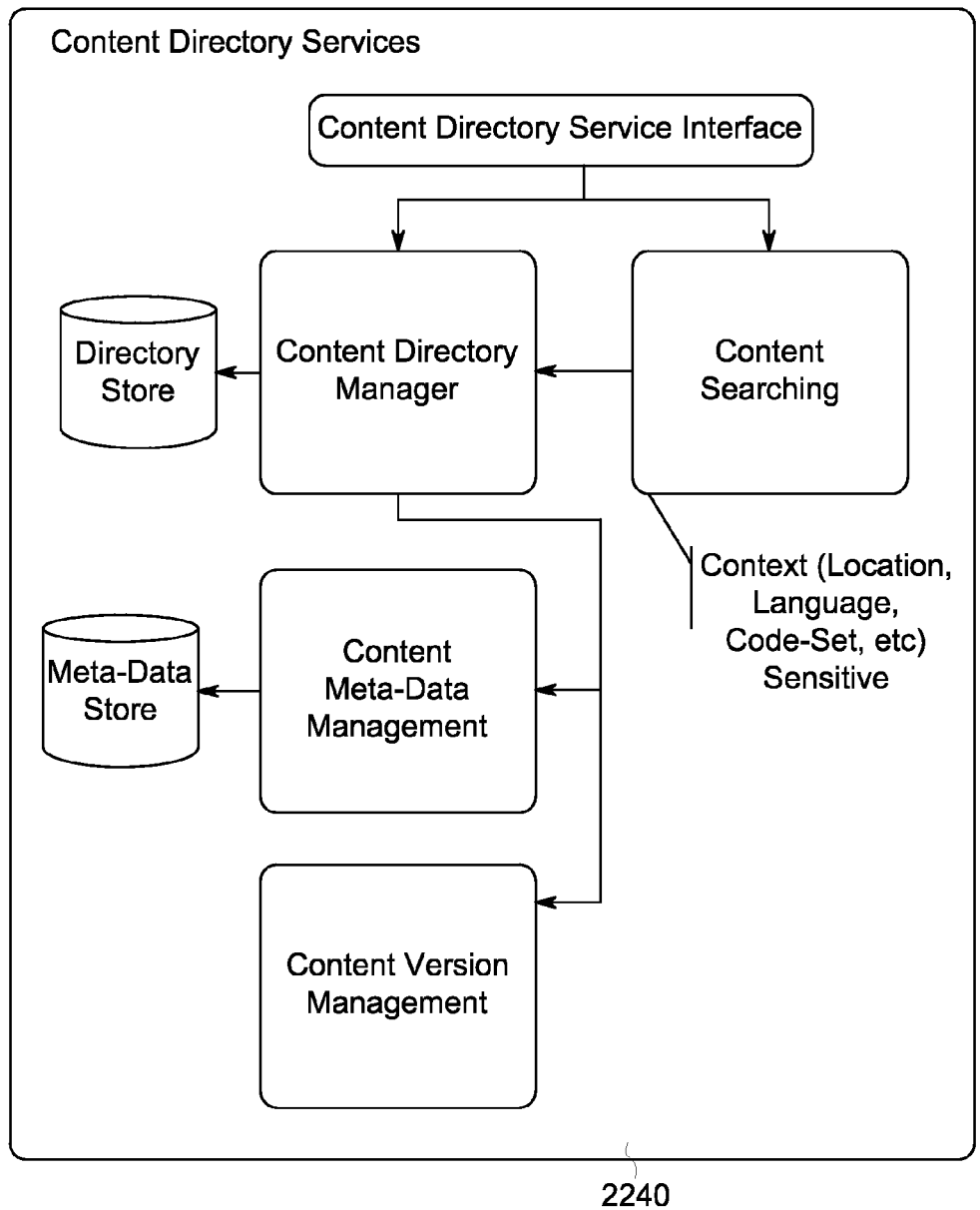
Figure 22E:
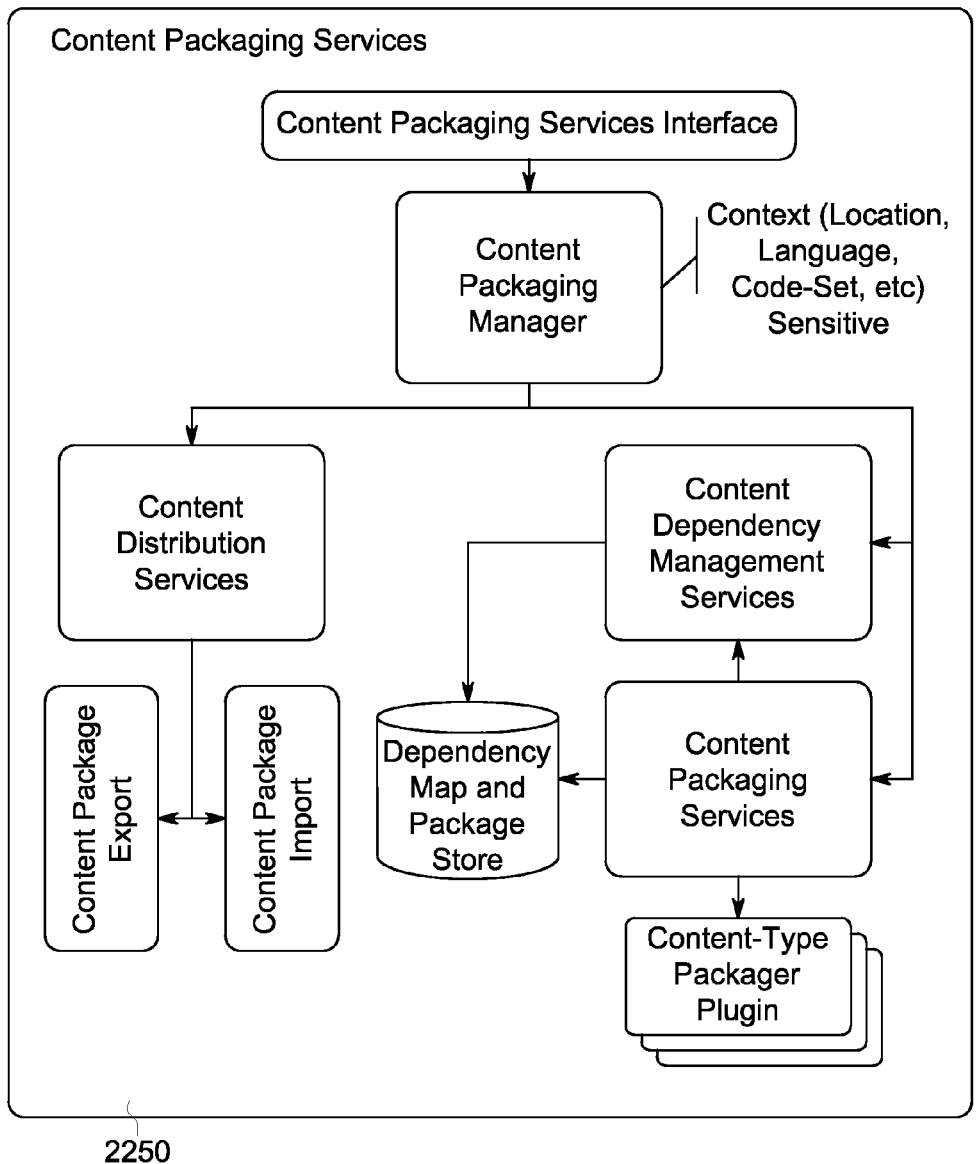
Figure 22F:
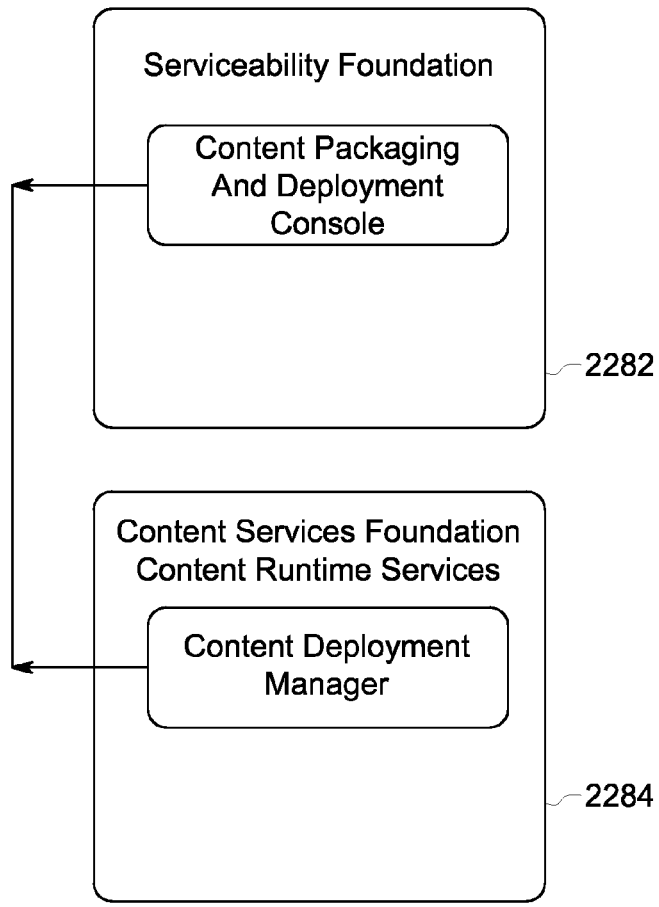
Figure 22G:
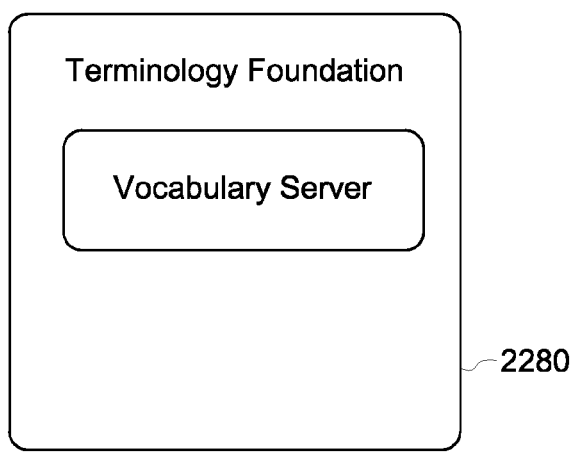
Figure 23A:
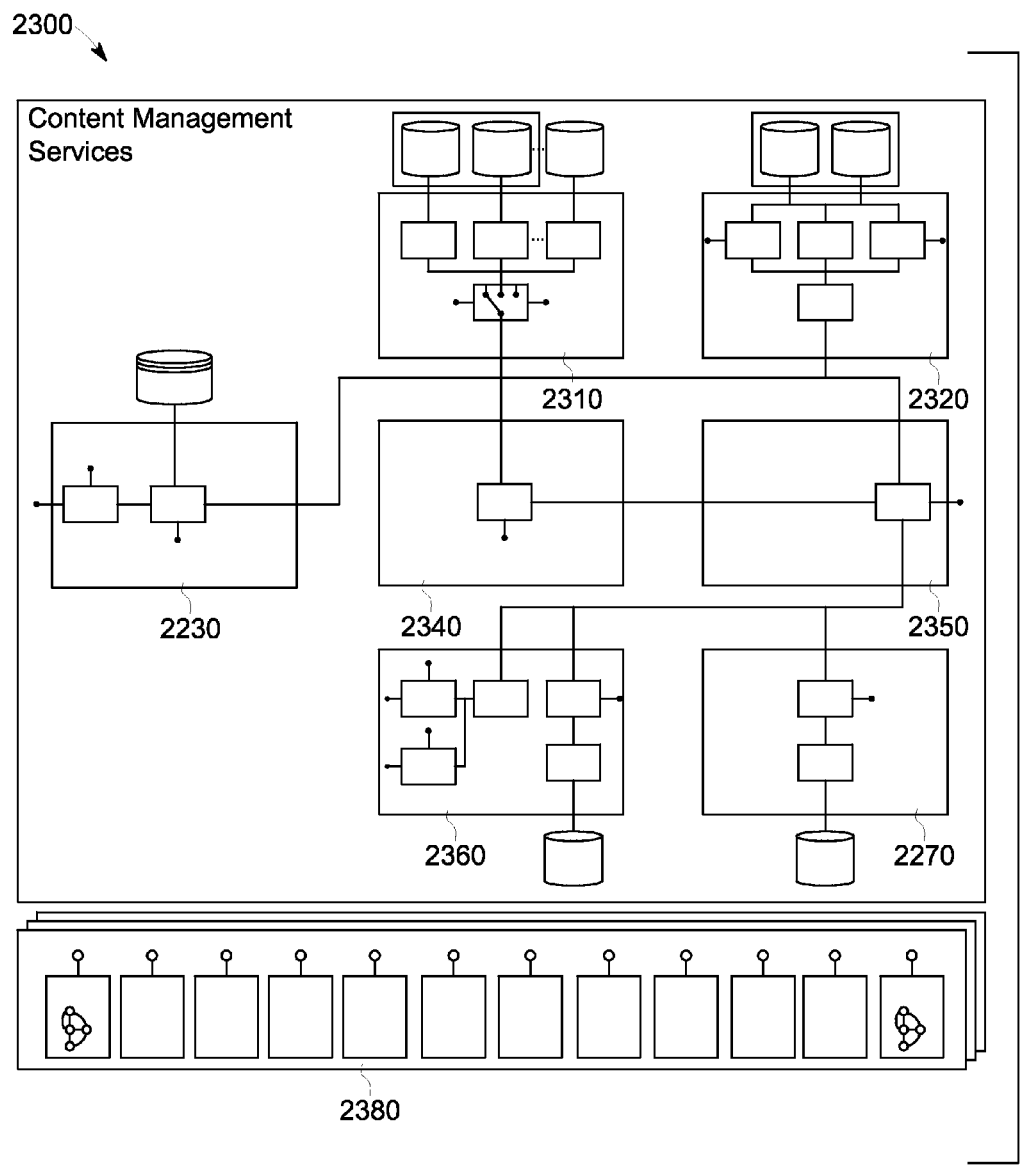
Figure 23B:
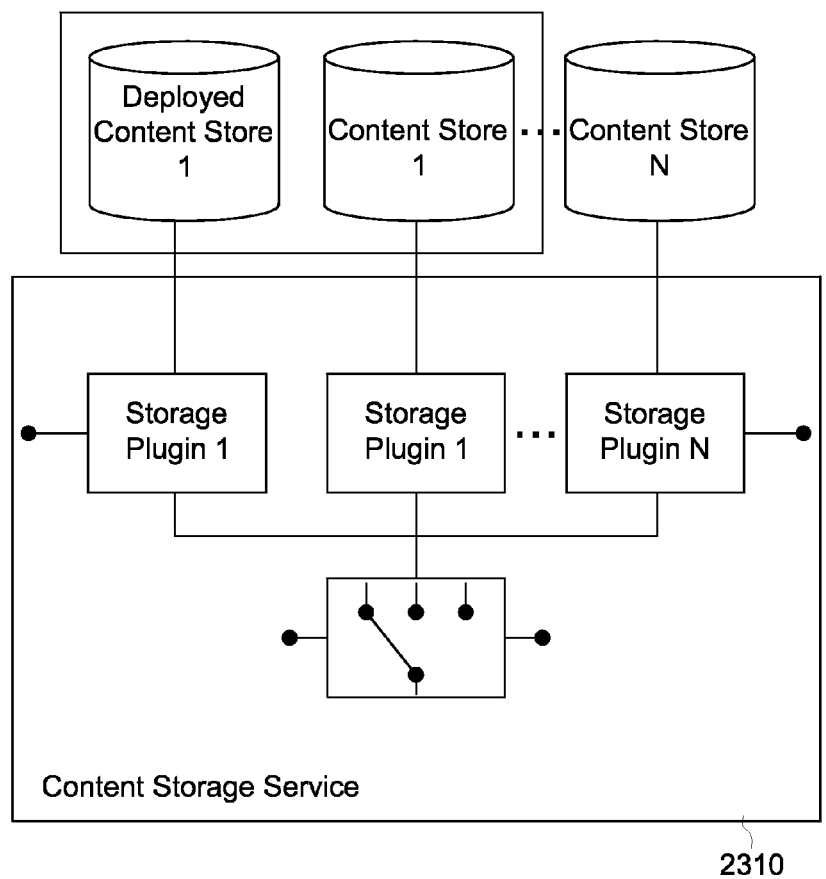
Figure 23C:
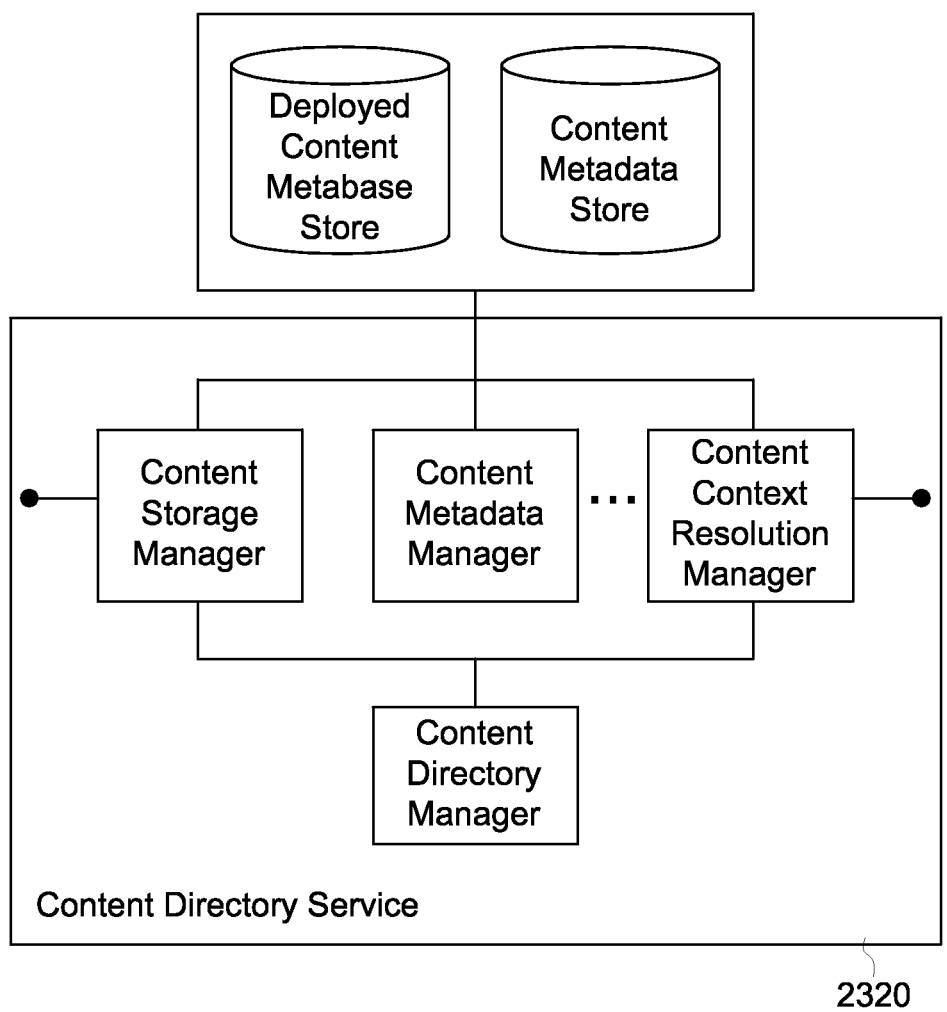
Figure 23D:
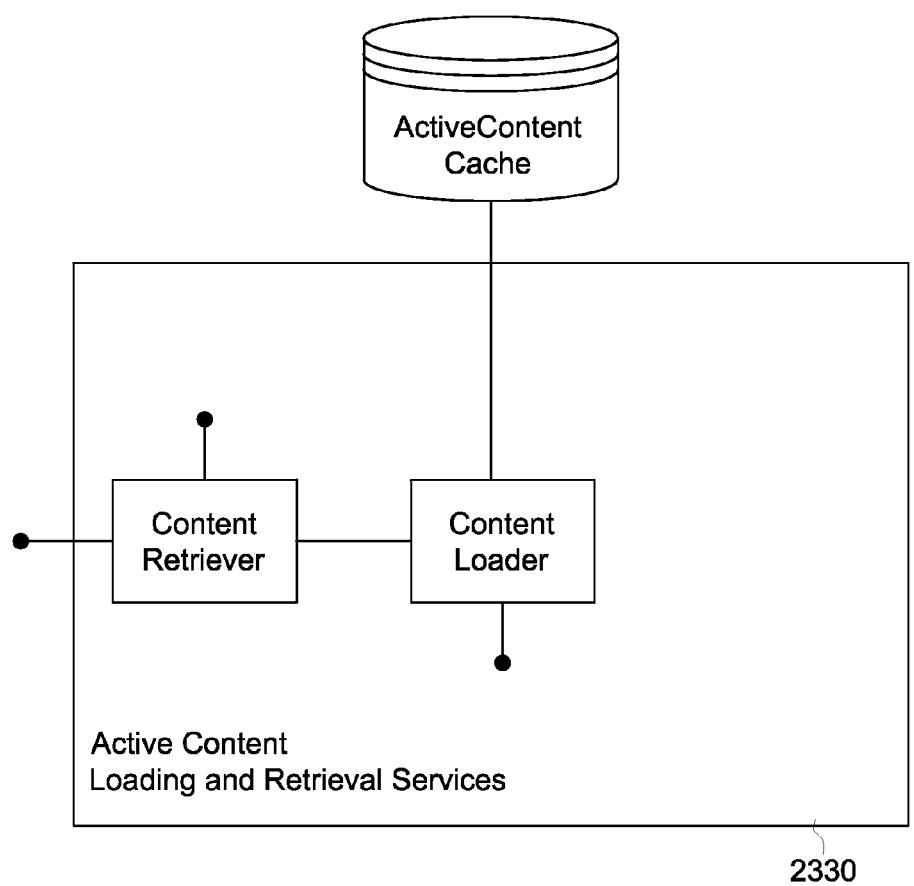
Figure 23E:
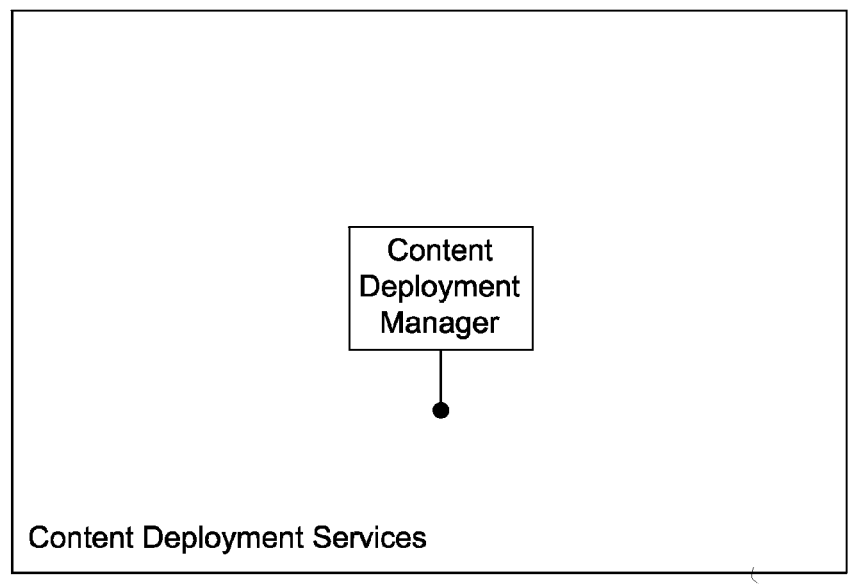
Figure 23F:
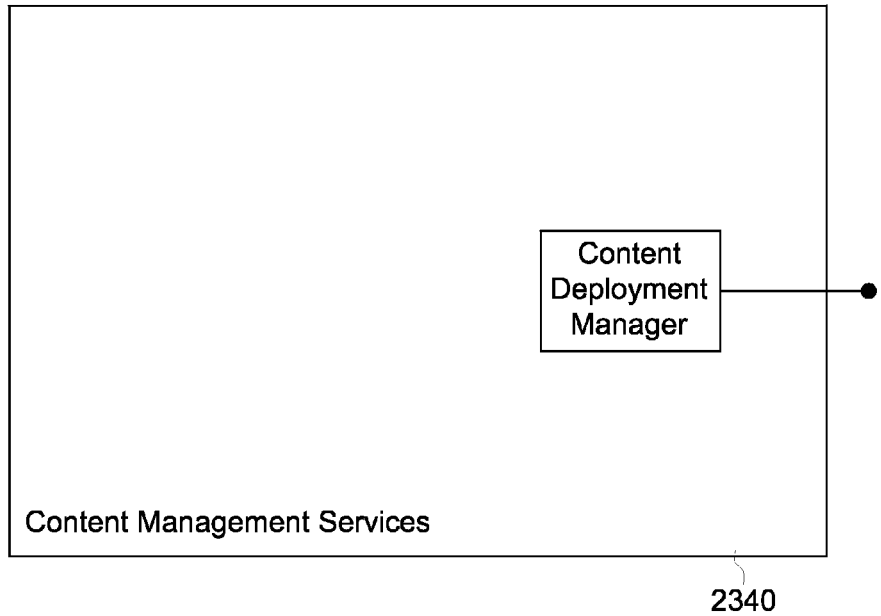
Figure 23G:
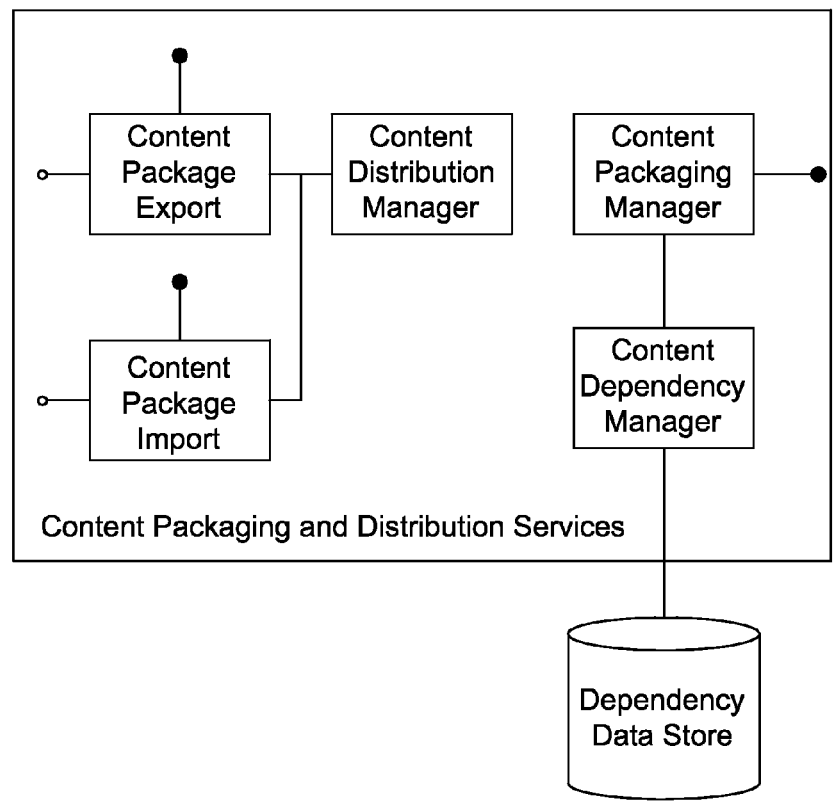
Figure 23H:
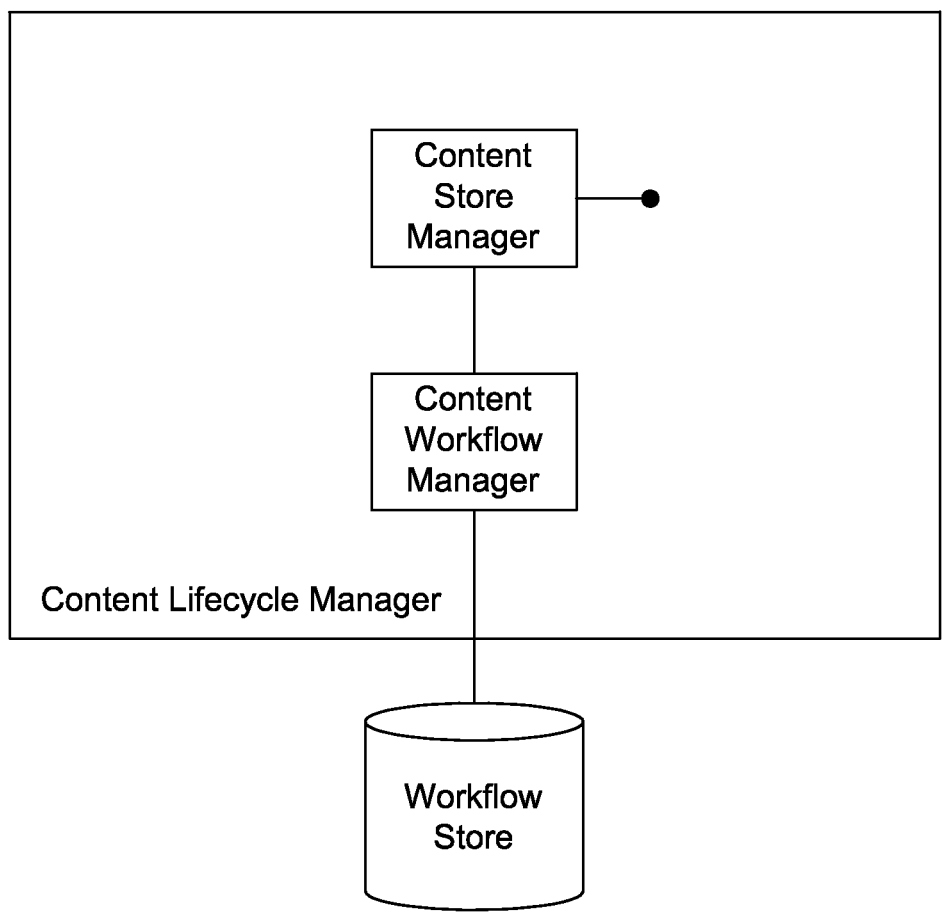
Figure 23I:
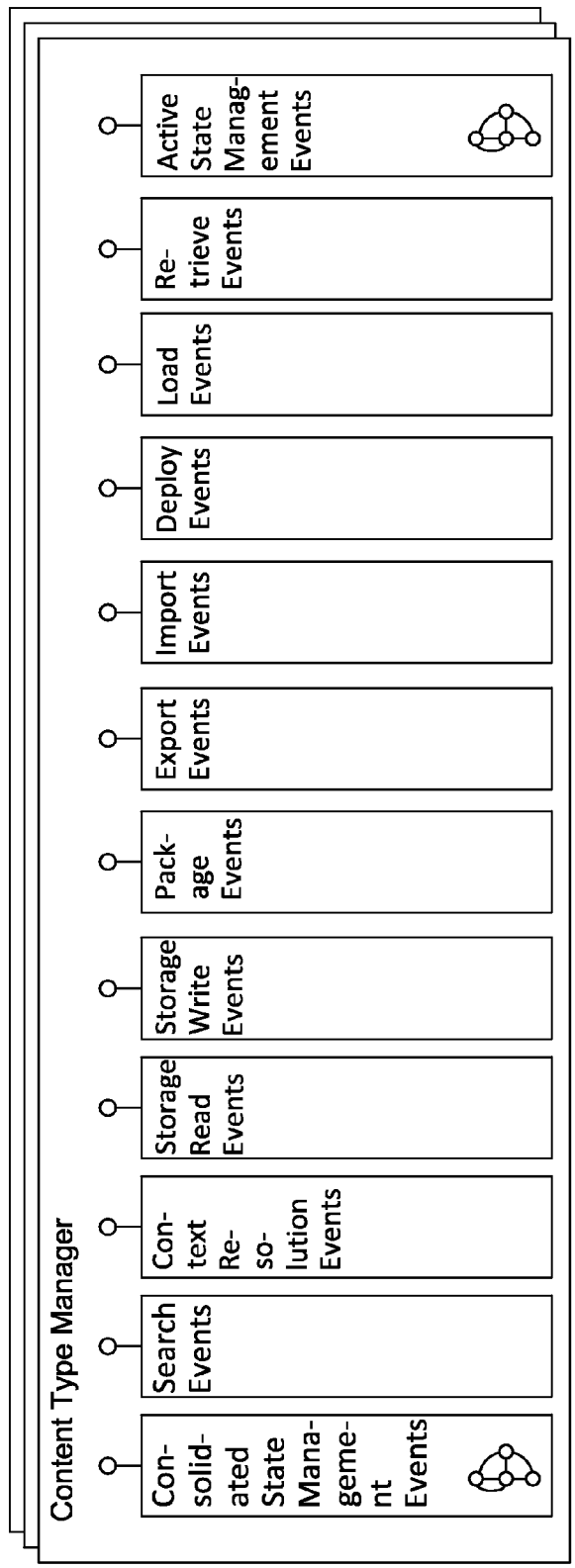

As illustrated in the example of FIG. 19, context resolution may occur at packaging time. First, as illustrated in the example of FIG. 20, conflicting context variants are rejected. As shown in the example of FIG. 21, conflicting context variants may be further eliminated based on an input context at packaging time.

FIG. 22 illustrates an example content management services system 2200. Content management services 2200 includes interrelationships of content storage, directory, lifecycle management, and packaging services. Packaging includes distribution and dependent management services, for example. The example content management services system 2200 manages content lifecycle.

The example system 2200 includes an interface 2210, which connects to a content manager 2220. The content manager 2220 connects with content storage services 2230, content directory services 2240, content packaging services 2250, and content lifecycle services 2260.

Content storage services 2230 includes an interface 2231 providing access to structured and unstructured content storage 2232-2233 and interacts with a data services foundation for document storage services 2270 for structured and/or unstructured document services 2270-2271.

Content directory services 2240 provides, via an interface 2241, content searching 2242 along with a content directory manager 2243. The manager 2243 accesses content metadata management 2244 and content version management 2245, for example. Content directory services 2240 include a directory store 2246 and a metadata store 2247, for example.

Content packaging services 2250 include an interface 2251 providing access to a content packaging manager 2252. The manager 2252 interacts with content distribution services 2253, content dependency management services 2254, and content packaging services 2255. Content distribution services 2253 connect to a content package export 2256 and content package export 2257. Content dependency management services 2254 and content packaging services 2255 communicate with a dependency map and package store 2258. Content packaging services 2255 also communicates with a content-type package plug-in 2259, which communicates with a terminology foundation 2280, in the example of FIG. 22. As shown in FIG. 22, the interface 2251 communicates with a serviceability foundation 2282 and a content services foundation 2284.

Content lifecycle services 2260 includes an interface 2261 for a content lifecycle manager 2262 which connects to storage 2263. The content lifecycle manager 2262 interacts with a workflow and activity management foundation 2290.

FIG. 23 illustrates another example content management services system 2300. In the example of FIG. 23, the system 2300 includes a content storage service 2310, a content directory service 2320, an active content loading and retrieval service 2330, a content deployment service 2340, a content management service 2350, a content packaging and distribution service 2360, a content lifecycle manager 2370, and a content type manager 2380. Components of the example system 2300 operate as described above with respect to managing, storing, loading, deploying, etc., content in a content-driven system and/or process.

In healthcare information technology, clinical information recorded in one information system and transferred electronically to another information system should retain enough of its intended and precise meaning to be safe and useful. In particular, the receiving health professional should be able to make proper decisions for diagnosis, treatment and care based on electronic exchanged information. Semantic interoperability is a property of a combined system containing two (or more) information systems such that specific aspects of the meaning of information passed from one to the other are invariant over the data exchange that carries the information. Semantic interoperability relates to unambiguous understanding of stored, used and communicated data. This means that patients, health care professionals, and others, including automated systems, may consistently and accurately interpret and act upon data in health care information systems without the intended meaning of that data being confused or changed.

To achieve semantic interoperability, standardization of clinical concept representation, including the content, the structure and the transmission processes for health data is provided. Using semantic interoperability, electronic health records (EHR) and other health IT may communicate and aggregate data from multiple sources and operate on the aggregated data as a cohesive whole. Exchanging information using standardized clinical concept representations takes its place as one of the specific kinds of semantic interoperability, with well defined benefits and limitations.

An ability to exchange information between clinical information systems without loss of clinical meaning helps enable safe and effective implementation of automated decision support across both received and local data. Similarly, to reuse clinical data on aggregate levels, the meaning of source data should be kept. To enable decision support, clarity should be provided as to what information is to be transferred, and what can be lost. Semantic interoperability implies that selected and received data may be combined seamlessly with local data and processed homogeneously. An effect of this is that clinical data from local and external systems may be combined and processed identically and collectively without loss of meaning.

To achieve semantic interoperability, clinical concepts may be defined in such a way that data related to those concepts may be properly interpreted. Detailed clinical models are a way to define clinical concepts in an implementation independent way, allowing in principle the translation from one technological implementation of a detailed clinical model into another implementation (e.g., assuming that all components of the detailed clinical models are part of both implementations).

A detailed clinical model is a description of small items of clinical information that includes the clinical knowledge on the concept. Detailed clinical models provide the data elements specification and attributes, including the possible values and types of the attributes, and, where possible, a model and technical implementation specifications, to convey the clinical reality in a fashion that is understandable to both clinical domain experts and modelers. Detailed clinical models include the potential for their use in health care information and communication technology, for example in EHR, telehealth applications, messages, medical devices, computer algorithms, and deductive reasoning, decision support, among others.

Standardized detailed clinical models underpin the coherence of electronic health records, where data is to be accepted from multiple sources and stored in a consistent deterministic fashion, where queries are to be constructed based on clinical knowledge and tied to clinician workflow, where services are to be automated based on known values of patient parameters linked to agreed protocols, where data display and data entry should be referenced to clinical guidelines, and where clinicians moving from system to system may minimize safety and quality issues through consistent information representation.

Standardized detailed clinical models enable decision support, facilitate effective and reliable analysis and aggregation for research, and help with the exchange of clinical information. In a given implementation context, detailed clinical models should be combinable into larger interlinked structures, sometimes with changing levels of detail as might occur for specifying a hospital discharge summary. Thus, for maximal reusability, detailed clinical models may include a capability to be comprehensive and/or to provide for different levels of detail through specialization.

A detailed clinical model is a relatively small, standalone information model designed to express a clinical concept in a standardized and reusable manner. It documents clinical information as a discrete set of precise clinical knowledge for that concept.

Structurally, a detailed clinical model provides the data elements and attributes of a clinical concept, including the possible values and types of attributes, and relationships needed to convey the clinical reality in a fashion that is understandable to both clinical domain experts and modelers, for example.

In certain examples, a Constraint Definition Language (CDL) defines a compiled, context free language allowing the definition of Detailed Clinical Models. Models are authored as text files, compiled, and stored as objects in a content database of a clinical knowledge and/or information system using the model. Programs read the object to retrieve information about the model (e.g., attributes, base models, etc.).

In certain examples, the CDL allows clinical data objects to be defined individually, with high fidelity (as opposed to traditional systems that require data objects to be fitted, often with fidelity loss, into a fixed set of database tables). Since models are stored as content, models can be created and modified at each implementation of the system with requiring the release of a new version of the software system. This, in turn, allows very rapid change to the clinical data objects required to support a clinical system.

In certain examples, the CDL allows models to be defined as content rather than involving database changes. Since the language is compiled, models may be validated for correctness and consistency by the compiler to help insure changes to models are allowable and safe. This allows for very fast evolution of a clinical system after release and distribution of the system, for example. This increases responsiveness of the system to user needs and lowers the costs of modifications to the system, for example.

Alternatively or in addition, one or more alternate languages (e.g., textual like CDL and/or graphical like unified modeling language (UML)) may be defined to represent clinical data objects.

In certain examples, the CDL implements an abstract constraint model defined as part of a clinical element model. The CDL uses a context-free grammar, for example, to describe constraint models.

The Clinical Element Model presents a model for describing and representing detailed clinical information wherein each item of clinical information is defined using a detailed model of the information. To accomplish this, the Clinical Element Model defines an information model representing instances of clinical information and a logical model representing an implementation of this information model. The logical model, in turn, represents clinical data using a two-layer data modeling approach in which the structure or representation of a data object (e.g., an instance of data) is separated from the definition of the information contained within the data object (e.g., a model defining the instance of data).

The logical model defining the representation of the actual data objects is referred to as an Abstract Instance Model. The logical model for defining the information contained within the data object is referred to as an Abstract Constraint Model.

A Clinical Element Information Model defines concepts, relationships, constraints, and rules that specify the semantics of an item of clinical information. The Clinical Element Information Model includes a vocabulary and data models, for example.

In the context of the Clinical Element Model, a vocabulary or terminology (e.g., a controlled medical vocabulary (CMV)) refers to a set of concepts for accurately describing the human body and associated components, conditions, processes, and process in a science-based manner. Clinical vocabularies may also extend into non-clinical areas. For example, a vocabulary may include concepts for billable items, billable procedures, etc., in a financial domain. Concepts are associated with each data model describing clinical data and with each element of the data model to define the meaning, or semantics, of the data. Use of a vocabulary allows for the unambiguous definition of clinical data. To facilitate common definitions of data, a number of standard vocabularies are defined (e.g., SNOMED-CT, LOINC, CPT, IDC-9, IDC-10, RXNORM, FDB, etc.).

Within an example clinical knowledge platform, vocabularies are used in a variety of ways. Vocabulary concepts may be used as actual clinical data (for example, a laboratory code, a patient's gender, the units within an observed physical quantity, etc.). Vocabulary concepts may be associated with an item of data to define the meaning, or semantics, of the data (for example, the vocabulary concept for blood pressure may be associated with the observed blood pressure physical quantity to define the meaning of the quantity). Relationships between vocabulary concepts may be used to capture and define clinical knowledge (for example, the knowledge that a particular antibiotic drug contains penicillin derived via a subsumption inference using the relationships).

An example information model used to represent a vocabulary includes Concepts, Designations, Properties, Relationships, Domains, and Mappings.

A concept is a word in a vocabulary and may be thought of as an abstract unit of clinical knowledge. A concept has no visible representation; that is, a concept is an abstract representation of the clinical idea. As such, a concept is represented simply as a persistent unique identifier and is often referred to as a "code". "Coded data" is thus data that has been associated with a specific concept that defines semantics of the data and/or data that has been converted to a specific concept code. In certain examples, only the concept code itself is stored as part of an item of clinical information.

In certain examples, describing a data item may involve multiple concepts. For example, defining a position on someone's body may require concepts for LEFT, UPPER, and ARM. When the data item is stored, the concepts may be stored individually and combined into a single sentence during subsequent retrieval and presentation (called post-coordination) or they may be combined into a sentence prior to storage and stored as a single concept (e.g., a single concept of LEFT-UPPER-ARM, called pre-coordination). The coordination scheme used varies from system to system (and often within a system as a matter of convenience) and is generally apparent in the data model(s) storing the concepts.

A designation or term is a "label" that may be used to represent a concept (e.g., a synonym or alternate representation of the concept). A designation may be a word, a phrase, an abbreviation, an acronym, an extern identification number, a picture, etc. Designations may be assigned a name or type (referred to as context) that may be used to reference a particular desired designation (for example, language, long vs. short form, display type, preferred form, etc.). Context may describe a facet of the designations place in the world or its intended use and is used as a selector of a designation when retrieved for consumption, for example.

A property is a text attribute that describes some aspect of a concept but that may not be used as a synonym or alternate representation of the concept. A property may be used to store some item of information about the concept that is useful to programs consuming the concept (for example, an indicator that the drug represented by a concept is part of an institution's formulary).

A relationship is a typed (e.g., named) association between two concepts within a single namespace or code-set. For example, penicillin IS_A drug, aspirin TREATS headache, headache IS_TREATED_BY aspirin, etc. A concept may participate in any number of relationships. Relationships may be hierarchical and may be selected by context. A type of the relationship may also be represented as a concept in the vocabulary.

A domain is a predefined, annotated collection of related concepts. For example, the set of drugs in the penicillin family, the set of clinical roles (e.g., doctor, nurse, etc.), etc. A pick list may be seen as a domain (or a subset of a domain) that is presented to a user for selection of some concept in the domain. Domains may also be referred to as "value sets" or as "value domains". Concept constraints in the Constraint Definition Language are defined using the keyword "domain", for example.

A mapping is a typed (e.g., named) association between a concept within one namespace (or code-set) and a second concept in another namespace. Sets of mappings define translations from one vocabulary to (generally equivalent) concepts in another vocabulary. For example, concepts representing laboratory results in the Qualibria vocabulary are mapped to the equivalent concepts in the LOINC vocabulary (the standard definition of laboratory result concepts).

Figure 24:
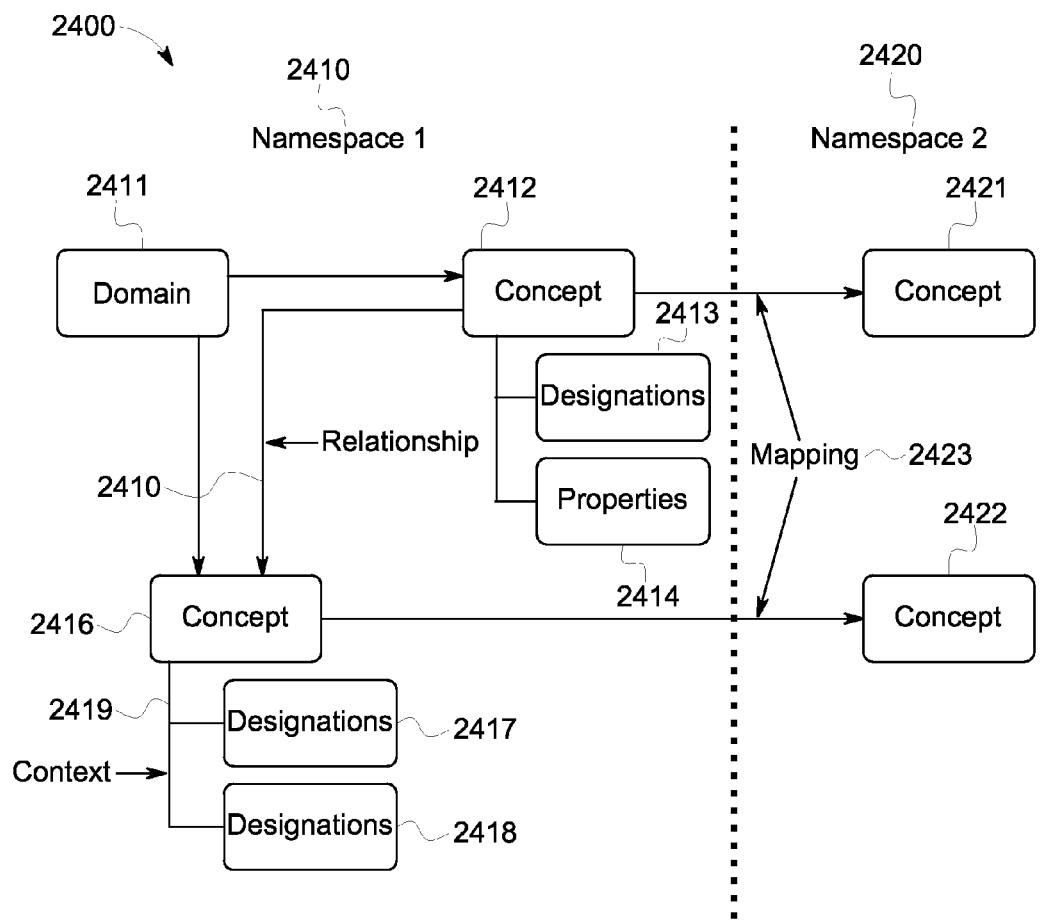
FIG. 24 illustrates an example vocabulary information model.

FIG. 24 illustrates an example vocabulary information model 2400. The example model 2400 includes a first namespace 2410 and a second namespace 2420. In the first namespace 2410, a domain 2411 is defined to include concepts 2412, 2416. Each concept 2412, 2416 is associated with one or more designations 2413, 2417 and properties 2414, 2418 as defined by a context 2419, for example. A relationship 2415 can be specified between the concepts 2412, 2416. In the second namespace 2420, concept 2412 can be mapped to concept 2421, and concept 2416 can be mapped to concept 2422 via mappings 2423.

A data model is an abstract model that describes how data is represented, organized, structured, and accessed. In the Clinical Element Model, data models formally define data elements and relationships among data elements within the clinical data domain that represent some clinical value of interest. The Clinical Element Model also specifies the basic data types used to represent individual data items in the data model.

Data models are constructed to insure semantic interoperability between computer systems (that is, the ability to transfer data between different systems with no loss of meaning) by defining clinical concepts in such a way that the data may be correctly interpreted independent of the technology of the systems that create or consume the data. This, in turn, allows the data to be unambiguously interpreted by computer programs such as decision support tools. Finally, data models may also allow poor quality or inconsistently provided data to be represented and stored in consistently interpretable ways.

The information model used to represent data models in the Clinical Element Model includes statements, associations, components, qualifiers, modifiers, attributions, and data elements, for example. Associations are a general category of information types that include panels, semantic links, collections, annotations, sequences, etc.

A statement represents an atomic, complete clinical sentence; statements may be considered the fundamental unit of clinical data. Statements may also represent descriptions of entities such as patients, encounters, providers, etc., in addition to direct clinical information. Statements are self-defining (that is, they have identity) and independently interpretable. A statement is associated with a vocabulary concept that defines the meaning of the statement.

Statements include of one or more components (which may include attributions, qualifiers, and modifiers, for example). They may be associated with other statements or associations by being referenced within an association. A component contained within a statement may have arbitrary cardinality, that is, zero, one, or many instances of the component may exist within the statement. A statement composed of more than one component may be referred to as a compound statement. In certain examples, an element of an association, statement, or component may be considered to behave as a set of elements with arbitrary cardinality.

For example, a statement may be "The systolic blood pressure of patient #175 at 10:15 pm is 120 mm Hg" or "Patient #892 was administered 100 mg of Aspirin at 3:25 am".

Figure 25:
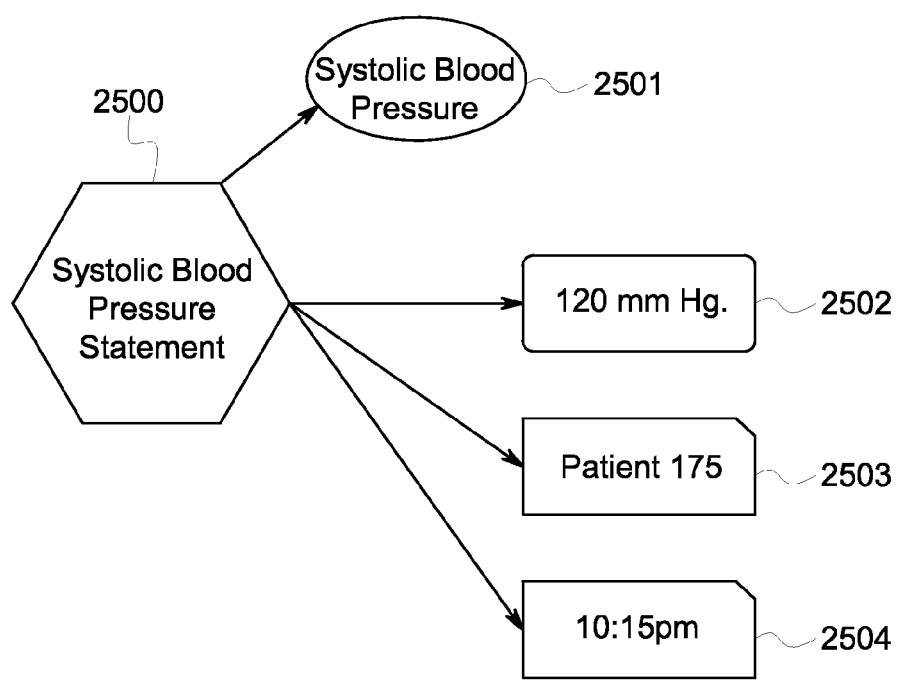
FIG. 25 shows a simplified graphical representation of a statement representing a systolic blood pressure observation.

FIG. 25 shows a simplified graphical representation of a statement 2500 representing a systolic blood pressure observation (using the first example from above). In this example, the term "Systolic Blood Pressure" represents a vocabulary concept of "systolic blood pressure" 2501, the physical quantity (120 mm Hg.) is represented as a data element 2502, and the patient identifier and time are represented as attributions 2503, 2504.

In certain examples, clinical entities such as patients, providers, encounters, contacts, activities, and locations are represented by specialized statements. A patient statement is a statement specialized to describe a patient (e.g., names, identifiers, demographic information, etc.). A provider statement is a statement specialized to describe a person, a group of persons, or an institution providing care for a patient (e.g., names, identifiers, demographic information, etc.). An encounter statement is a statement specialized to describe administrative and clinical encounters. An encounter statement is owned by a patient, for example. A contact statement is a statement specialized to describe a single interaction between a patient and a care giver (e.g., a provider). A contact statement is owned by a patient and is usually associated with one or more encounters, with one or more providers, and with a location. An activity statement is a statement specialized to describe a clinical activity (e.g., an atomic unit of clinical care). An activity statement is owned by a patient and generally associated with an encounter and a contact. A location statement is a statement specialized to describe a location at which clinical care is provided. Statements containing data owned by a patient are associated with a patient statement and usually associated with an activity statement, a contact statement, and encounter statement.

An association represents a set (e.g., a collection) of related statements and/or other associations. Like statements, associations are self-defining (that is, they have identity) and independently interpretable. An association is associated with a vocabulary concept that defines the meaning of the association.

Associations may be viewed as containing a set of references to independently created statements or associations. A statement or association contained within an association may have arbitrary cardinality, that is, zero, one, or many instances of the statement or association may exist within the association.

An association need not necessarily be created coincidentally with the referenced statements or associations (e.g., previously existing statements or associations may be referenced by a newly created association). Further, a statement or association may be referenced within more than one association (for example, within annotations and semantic links). The statements and associations referenced within an association may be retrieved and interpreted in the context of the association or may be retrieved and interpreted independently of the association. In the case of panel associations, conduction may be used to provide context contained within the panel to the statements and associations referenced in the panel.

Statements or associations referenced within an association may often be considered to serve some role within the association. For example, in a semantic link association, one referenced element may serve the role of originator of the link and another element the role of target of the link.

In addition to referenced statements or associations, associations may contain components, attributions, qualifiers, and modifiers. A component contained within an association may have arbitrary cardinality, that is, zero, one, or many instances of the component may exist within the association.

The term association is used to represent a general class of relationships between statements and associations that includes a number of behaviorally similar but semantically specialized associations which represent different types of relationships between the elements in the associations. Associations may be specialized as panels, collections, sequences, lists, semantic links, annotations, and patient relationships.

A panel is an association wherein the referenced statements and/or associations are assumed to be strongly semantically related; statements and associations are assumed to share context provided by the panel referencing them.

The panel and the referenced statements and/or associations may be coincidentally created or updated (although panels may also be incrementally constructed). In certain examples, because of the strong semantic relationship between elements that a panel represents, statements and associations referenced within a panel may not be modified independently of the panel that contains them.

For example, the results of a panel of laboratory tests conducted against a single physical sample could be represented by a panel association. The systolic and diastolic blood pressure observations taken together could be represented by a blood pressure panel association. In both examples, the referenced statements share the context provided by the physical samples or observations.

Figure 26:
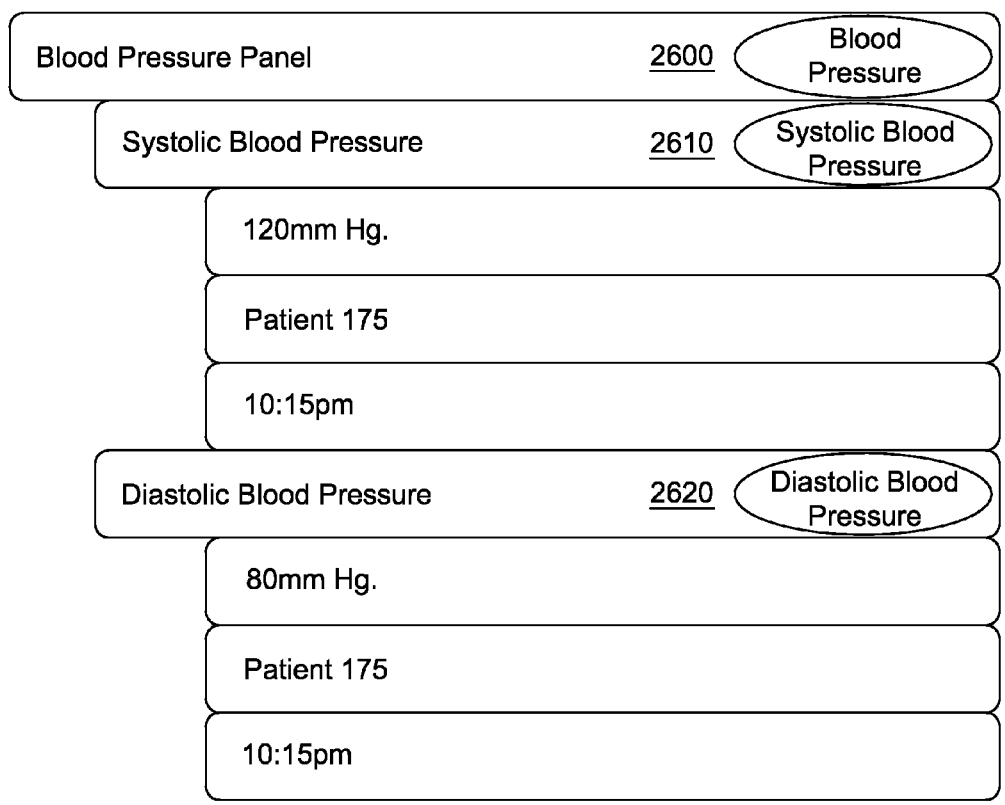
FIG. 26 depicts an example simplified panel describing a blood pressure panel referencing the statements describing the systolic and diastolic blood pressure taken as a single observation.

FIG. 26 depicts an example simplified panel describing a blood pressure panel 2600 referencing the statements describing the systolic 2610 and diastolic 2620 blood pressure taken as a single observation (this example is representative of the structure of all types of associations).

A collection is an association wherein the referenced statements and/or associations are assumed to not be strongly semantically related; that is, the collection may be arbitrarily defined and will share limited context (if any). Often the basis of the collection may simply be that the referenced statements and associations were created as part of the same event (for example, created as a result of the execution of a single form). The collection and the statements and/or associations referenced within the collection may or may not be coincidentally created. There is no assumption of shared context between the collection and the referenced statements and/or associations.

A sequence is an association wherein the referenced statements and/or associations are part of some ordered sequence of related statements and/or associations and wherein the state of the sequence as a whole is of interest. Referenced statements and/or associations are assumed to serve some role in the sequence, for example, initiating the sequence, terminating the sequence, continuing the sequence, etc. Roles are represented by vocabulary concepts. The sequence and the statements and/or associations referenced within the sequence may not generally be coincidentally created (though they may be partially coincidental); typically, references to statements and/or associations are added to sequence incrementally as they are created.

Figure 27:
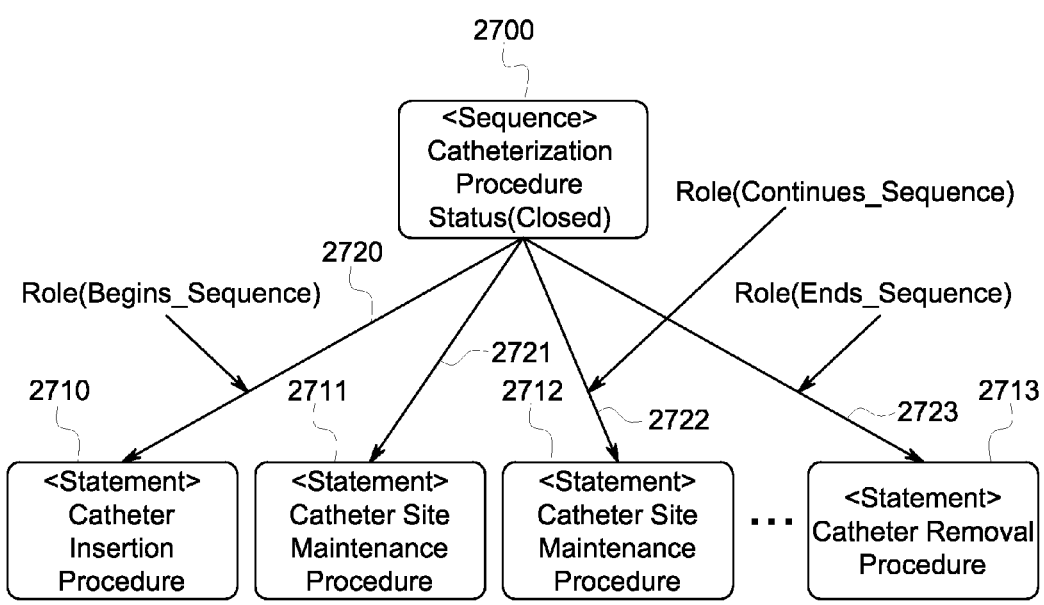
FIG. 27 shows a plurality of event statements incrementally added to a sequence.

While the elements within a sequence are assumed to be semantically related, there is no assumption of shared context between the sequence and the referenced statements and/or associations (unlike panels). Shared context, if any, must be provided by the logic creating the sequence; conduction, as used in panels, is not defined. For example, when a catheter is inserted in a patient, a sequence of statements is collected over the course of the catheterization. For examples, as shown in FIG. 27, a statement describing the insertion of the catheter 2710, statements describing site maintenance 2711, 2712, and a statement describing removal of the catheter 2713 may incrementally be added to a sequence 2700. The sequence defines one or more roles 2720-2723 indicating begin sequence 2720, continue sequence 2721, 2722, and end sequence 2723.

The state of the sequence (inserted, removed, etc.) may change as statements are incrementally added; an application may query the state of the sequence to display whether the catheter is currently inserted or has been removed. Inferences regarding the state of the sequence are possible; for example, addition of a statement describing site maintenance could imply that a catheter has been inserted even in the absence of a statement describing insertion of the catheter.

A list is an association that contains a set of individually created and attributed associations (called reference associations) that each reference some other independent statement or association (e.g., the contained associations act as indirections to the statements or associations of interest).

The list and the reference associations referenced within the list are not generally be coincidentally created (though they may be partially coincidental); typically, references to reference associations are added to the list incrementally as they are created. Unlike other types of associations, reference associations may often be removed from a list as the list is maintained over time. A reference association is undefined outside of the context of a specific list.

There is no assumption of shared context between the list and the contained reference associations. For example, a list of patients (e.g. patient statements) may be shared by multiple users where each user can independently add patients to the list (or remove them). Each patient added to the list is represented in the list by a reference association that in turn references the indicated patient (see, e.g., FIG. 28). The reference association is fully attributed to the user that added the patient to the list and may contain data elements allowing additional information to be recorded regarding the list entry if desired.

Figure 28:
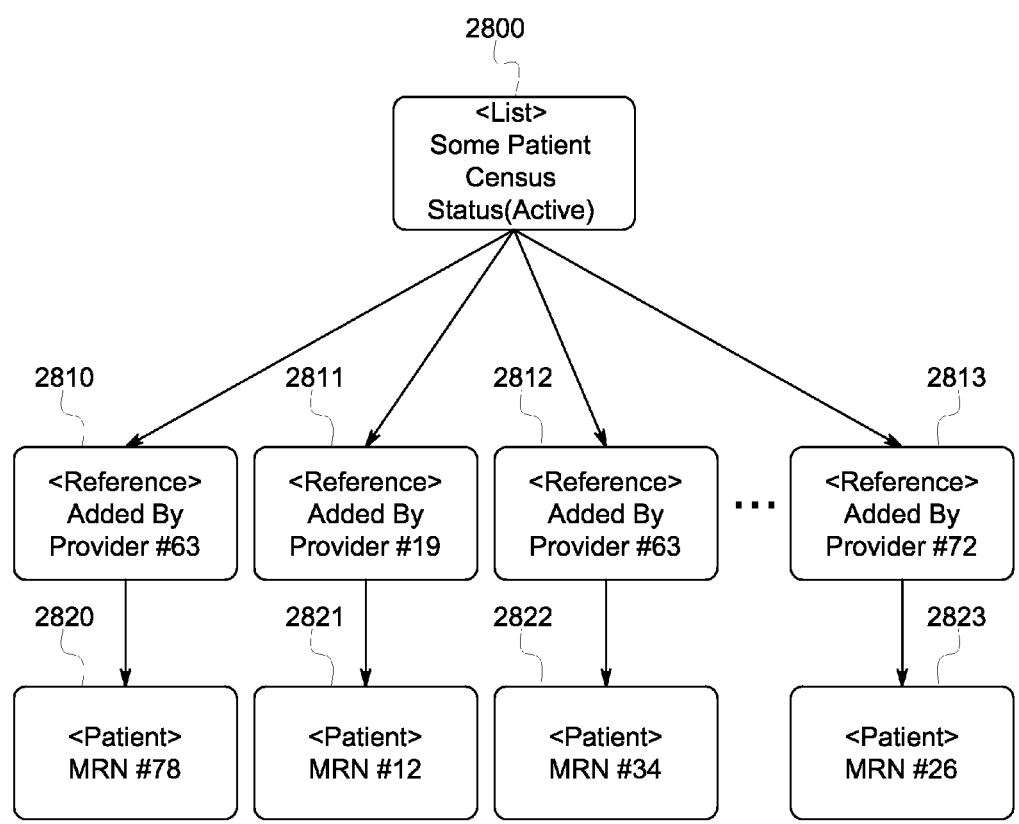
FIG. 28 shows an example patient census list.

As shown in the example patient census list 2800 of FIG. 28, a plurality of references 2810-2813 can be added to the list 2800 by a plurality of identified providers. Each reference 2810-2813 is associated with a patient 2820-2823 identified by a reference number, for example.

A semantic link is an association that establishes a strongly typed semantic relationship between two or more statements or associations. The type of relationship is represented by a vocabulary concept allowing any arbitrary relationship to be established. Statements and/or associations referenced in a semantic link are assumed to serve some role in the semantic link, for example, the source of the relationship, the target of the relationship, etc. Roles are represented by vocabulary concepts. The semantic link and the referenced statements or associations are not generally be coincidentally created; rather, semantic links are often established independently and after the creation of the related statements or associations (though not always).

Figure 29:
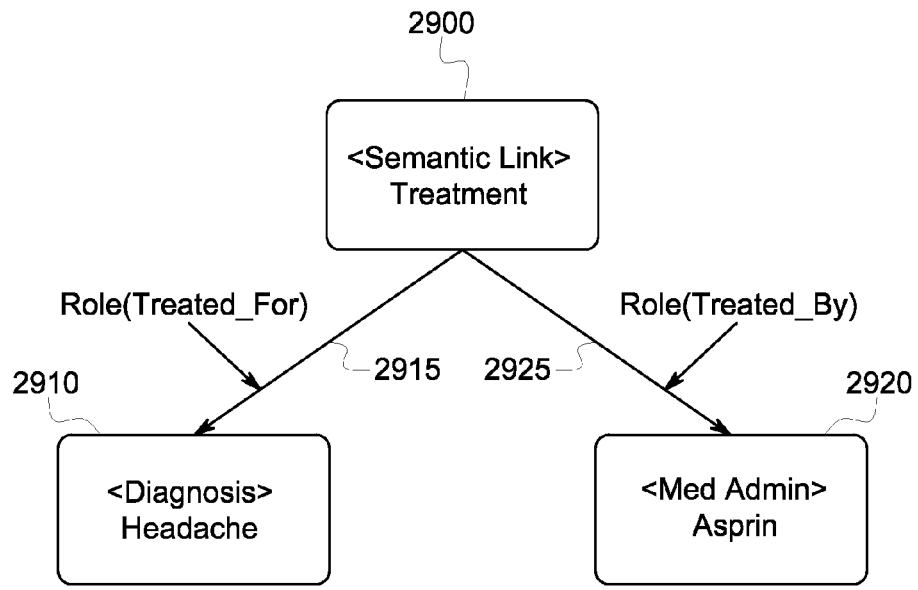
FIG. 29 depicts an example semantic link for treatment including a diagnosis and a medication administered.

There is no assumption of shared context between the semantic link and the referenced statements and/or associations. For example, a semantic link might be established between a medication administration statement and a diagnosis statement to establish the medication was administered to treat the diagnosed condition (see, e.g., FIG. 29). FIG. 29 depicts an example semantic link 2900 for treatment including a diagnosis 2910 (e.g., headache) and a medication administered 2910 (e.g., Asprin). The diagnosis 2910 and medication 2920 are linked to the semantic link 2900 by role 2915, 2925 (e.g., treated for 2915 headache 2910 and treated by 2925 administering Asprin 2920).

An annotation is an association that adds independent information to the referenced statements and/or associations. Annotations are strongly typed, as represented by a vocabulary concept, and created independently of the referenced statements and associations. Components, of which the annotation is composed, carry the information that annotates the referenced statements and associations; attributions contained in the annotation describe the event creating the annotation. There is no assumption of shared context between the annotation and the referenced statements and/or associations.

Figure 30:
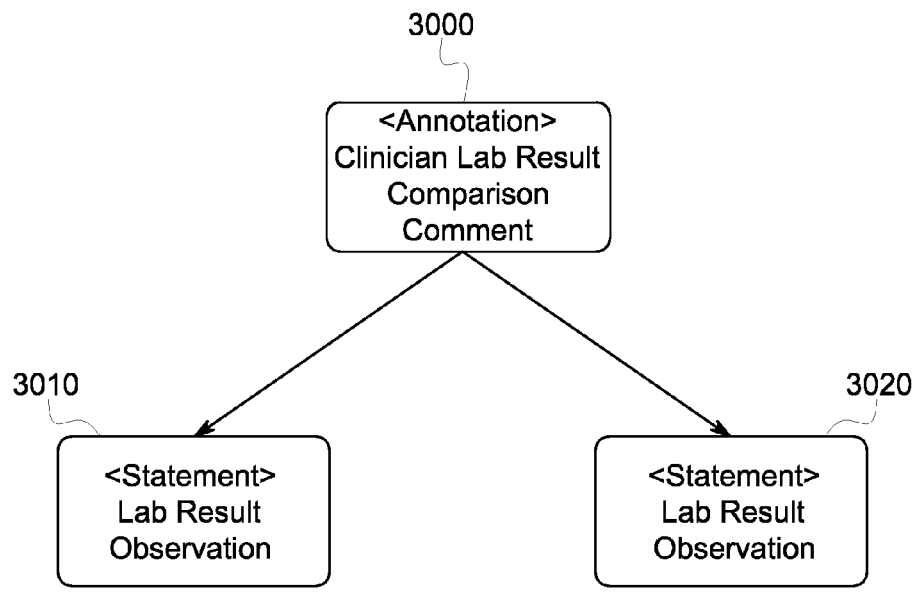
FIG. 30 illustrates an example annotation associated with a plurality of statements.

A clinician comment annotating an observation such as laboratory result (or results) serves as a simple example of an annotation (see, e.g., FIG. 30). As an additional example, annotations may be used by an application to tag an arbitrary set of statements or associations for subsequent retrieval and analysis. FIG. 30 illustrates an example annotation 3000 (e.g., a clinical lab result comparison comment) associated with a plurality of statements 3010, 3020 (e.g., lab result observations).

A patient relationship is an association that establishes a strongly typed relationship between one or more patients and one or more providers. The type of relationship is represented by a vocabulary concept allowing any arbitrary relationship to be established between patients and providers.

A patient relationship may be assigned a vocabulary concept representing the strength of the relationship (e.g., self-assigned, ADT system assigned, etc.). Additionally, a patient relationship may include time constraints that govern the state of the relationship, for example, an association with an encounter that constraints the patient relationship to be active only within the lifetime of the encounter. As with all associations and statements, components may be added to the patient relationship to provide additional context for the relationship.

Patients and providers referenced in a patient relationship are assumed to serve some role in the patient relationship; for example, in a clinical care team patient relationship, a provider may be assigned an attending physician role, a respiratory therapist role, etc. Roles are represented by vocabulary concepts.

The patient relationship and the referenced patients and providers are not generally be coincidentally created; rather, patient relationship are often established independently of and after the creation of the related patients or providers (though not always). There is no assumption of shared context between the patient relationship and the referenced patients and providers.

A component is a piece of information contained within a statement, an association, or another component; statements, associations, and components may be seen as (at least partial) compositions of components, that is, owning and containing zero, one, or more child components. Additionally, components act as the container for zero, one, or more data elements that represent actual data values. A component or data element contained within a component may have arbitrary cardinality, that is, zero, one, or many instances of the component or data element may exist within the component.

Components are not self-defining (that is, they do not have identity) and are interpreted in the context of the statement or association that owns them. A component is associated with a vocabulary concept that defines the meaning of the component.

Qualifiers, modifiers, and attributions may be seen as semantic specializations of components and conform to this description of components. For example, in the statement "The systolic blood pressure of patient #175 at 10:15 pm is 120 mm Hg", the patient identifier, the time, the blood pressure physical quantity value would all be represented as components owned and contained by the systolic blood pressure statement.

Figure 31:
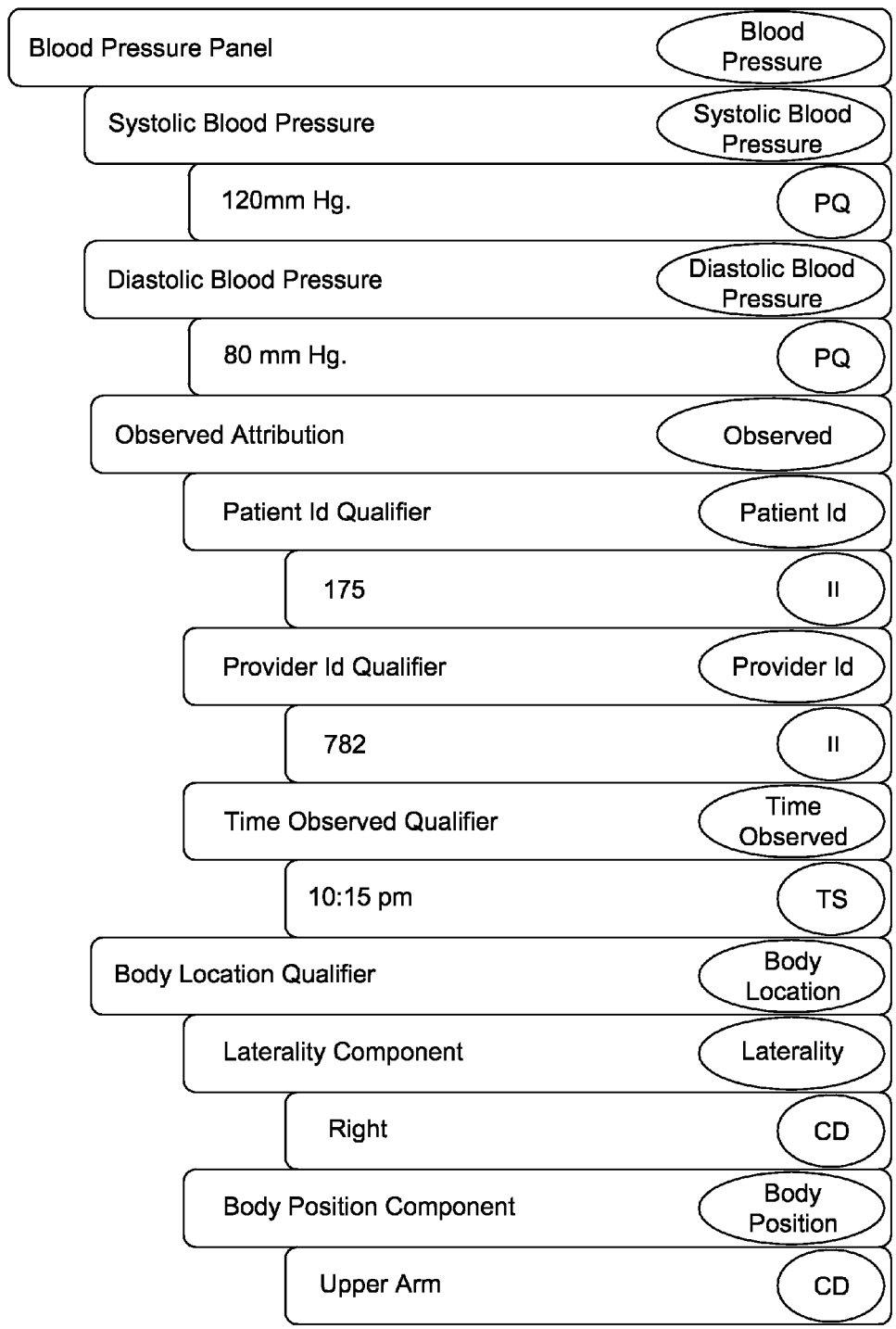
FIG. 31 presents the blood pressure panel association with components and data elements qualified.

FIG. 31 presents the blood pressure panel association from the previous examples with all components and data elements fully qualified.

Qualifiers, modifiers, and attributions are semantic specializations of a component. Qualifiers, modifiers, and attributions behave as described above for components, for example.

A qualifier is a semantic specialization of a component that provides additional, supplementary information to the information contained within another component, statement, or association. For example, the body position at which a blood pressure measurement was taken may be thought of as qualifying the blood pressure statement.

A modifier is a semantic specialization of a component that alters the meaning of the information contained with another component, statement, or association. For example, a negation modifier would indicate that the information contained a component was not present, was not true, etc. A subject modifier indicates that the information contained in the component applied to a patient other than the patient associated with (e.g., owning) the containing statement or association.

An attribution is a semantic specialization of a component that provides information describing the event of creating the information contained within another component, statement, or association. For example, the user creating the information, the data and time the information was created, and the location at which the information was created may be seen as attributions.

Data elements are attributes of components that contain actual instances of data; as such, components may be seen as compositions of data elements. Components may contain zero, one, or many data elements; any data element contained within a component may have arbitrary cardinality, that is, zero, one, or many instances of the individual data element may exist within the component. Each data element contains a single item of data of a specific data type, for example, concept, integer, real number, string, physical quantity, ratio, etc. Data types are derivatives of, but not identical to, the HL7 V3 RIM datatypes, for example.

In certain examples, the logical model implementing the Clinical Element Model represents clinical data using a two-layer data modeling approach in which the structure or representation of a data object (that is, a model defining the implementation of an instance of data) is separated from the definition of the information contained within the data object (that is, a model defining the content and semantics of an instance of data). The logical model defining the implementation of an instance of data (that is, the actual data object) is referred to as the Abstract Instance Model.

The Abstract Instance Model, often referred to as the reference model (or, when implemented, the reference implementation), defines a stable object model against which software can be built and data physically stored. The reference model is, in a sense, generic and data model agnostic. All instances of data are represented using the same concrete data structure; programs reference only this single, generic data structure rather than data objects specific to each different data model. Instances of data are also stored generically, for example, by using an associative database model as opposed to a more traditional relational database structure. The reference model may evolve and change independently of any model describing clinical data; for example, a new model representing a clinical data object may be added to the system and instances of that data model may be stored without changes to the reference model and optimizations may be performed against the reference implementation without changes to a data model.

In an example implementation of the Clinical Element Model, an instance of data is defined using a logical model that may be used as a reference by applications consuming instances of the Abstract Instance Model. Changes to the logical instance model thus also involve changes to any application consuming those instances.

Data instances behave as objects in an object-oriented programming model; the data instance encapsulates the information contained within the instance. Typically, programs consuming data instances will not directly access elements (e.g., attributes or properties) within the instance; rather elements are accessed via logical interfaces defined using the Abstract Constraint Model defining the information contained within the instance. Further, a program operates on the complete instance object; elements are not queried or accessed outside of the context of the containing instance.

Information within the logical instance is organized as a hierarchy of elements as required by the Clinical Element Information Model. At least conceptually, individual elements within an instance are identified by a path that identifies the exact branch of the hierarchy that contains the element.

In certain examples, the logical instance model includes three fundamental classes: instances, components, and data elements; instances are further specialized into statements and associations.

An instance is the basis for all data objects represented by the Abstract Instance Model. Instance is an abstract class that provides the core identity of any data object by defining the instance identifier, the data model (or type) describing the instance, the vocabulary concept (or key) defining the semantics of the instance, and the base attributions describing creation of the object (e.g., creating user, time of creation, etc.).

Instances (e.g., statements and associations) may be considered to be compositions of zero, one, or many components. Components do not have identity and may not be created or interpreted outside of the context of the instance that owns the component. Components contain a reference to the instance that owns them, a reference to the component that owns them (if any), the model (or type) describing the component, and the vocabulary concept defining the semantics of the component. Components, as previously indicated, may be compositions of components which leads to the hierarchal data structure of an instance. Components may be further semantically specialized into qualifiers, modifiers, attributions, and anonymous data components. The term components as used here refers to semantic specializations of components defined by the information model, that is components, modifiers, qualifiers, data components, and attributions.

Components may be composed of zero, one, or many data elements. Each data element, in turn, contains a single instance of one of the primary datatypes which uniformly specialize the datatype ANY, for example.

In the logical instance model, statements (as described in the information model) are segregated into two categories, general statements and patient statements.

General statements are those statements without an intrinsic ownership relationship with a patient. Patient statements are those statements with an intrinsic ownership relationship with a patient. The PatientStatement class, which specializes the GeneralStatement class, essentially establishes ownership of a data instance by a patient and allows the data instance to be associated with an activity and a contact. General statements are further specialized to define patient statements, encounter statements, contact statements, activity statements, provider statements, location statements, and generic data statements. Generic data statements represent data instances that are not owned by a patient.

Encounters, contacts, and activities are considered as general statements but establish individual ownership relationships with patients. Encounters are considered in the Qualibria implementation of the Abstract Instance Model to represent arbitrary collections of activities; activities may be collected into multiple encounters based on business and clinical needs. Therefore, direct relationships between encounters and patient owned data instances are not established within the logical instance model.

Patient statements are further specialized to represent statements containing patient owned data. In certain examples, a single Statement class to represent patient owned data may be defined. In certain examples, additional classes representing additional, more specialized data classes may be added.

Similar to statements, the logical instance model segregates associations (as described in the information model) into two categories, general associations and patient associations. General associations are those associations without an intrinsic ownership relationship with a patient. Patient associations are those statements with an intrinsic ownership relationship with a patient. The PatientAssociation class, which specializes the GeneralAssociation class, essentially establishes ownership of a data instance by a patient and allows the data instance to be associated with an activity and a contact.

Fundamental to any association is a set of references to other instances (which may be statements and/or associations). The references may contain copies of attributes belonging to the referenced instances to facilitate querying of associations.

The Logical Instance Model defines several specializations of association that are of value to the reference implementation but that are not defined in the information model (e.g., location relationships, security constraints, etc.). The Logical Instance Model allows for the definition of specialized associations and statements that are used primarily within the reference implementation.

General associations may be further specialized to define general lists, instance references (for use in lists), and location relationships (a utility association for defining location hierarchies within the reference implementation), for example.

Patient associations may be further specialized into Panels, Collections, Sequences, Semantic Links, Annotations, and Patient Relationships, for example.

The example Clinical Element Model defines clinical data as a large, unstructured set of data objects described by largely independent data models. From a practical perspective, however, different types of data exhibit different behaviors despite being described using the same logical instance model. For example, data objects may have different life-cycles (e.g., longitudinal vs. episodic data) that involve different partitioning and archiving strategies, different integrity requirements (e.g., database foreign keys between objects to support referential integrity), different indexing and search requirements (e.g., indexes to support searching for data objects based on data model or vocabulary ontologies), etc.

To account for the behavioral differences between types of data objects in an implementation of the Clinical Element Model, the reference model is further subdivided into a set of reference classes, that is, partitions (e.g., behaviorally based) of possible data objects that may then be managed in the reference implementation individually.

The basis for reference classes was largely established within the logical instance model described earlier, that is, the example implementation of the Abstract Instance Model. The specialization of instances into statements and associations, the specialization of statements into patients, providers, encounters, contacts, activities, patient data statements, and locations, the specialization of associations into panels, collections, sequences, lists, semantic links, annotations, and patient relationships and the specialization of components into qualifiers, modifiers, and attributions represents the initial partitioning of data into reference classes. Each of these classes of data is distinct in at least one of the behavioral dimensions mentioned earlier.

Figure 32A:
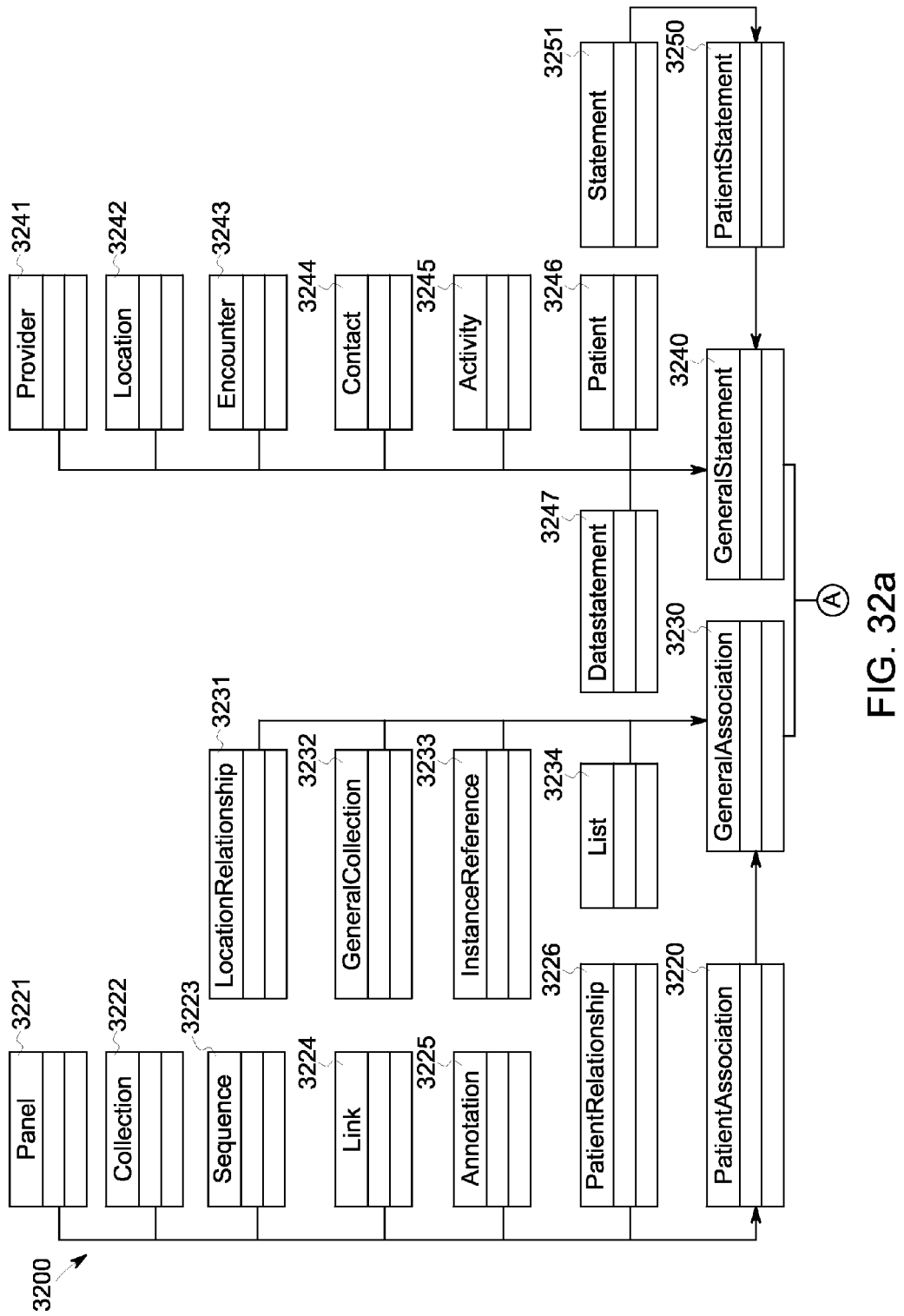
FIG. 32 shows a diagram of an inheritance hierarchy of reference classes in an example reference implementation.
Figure 32B:
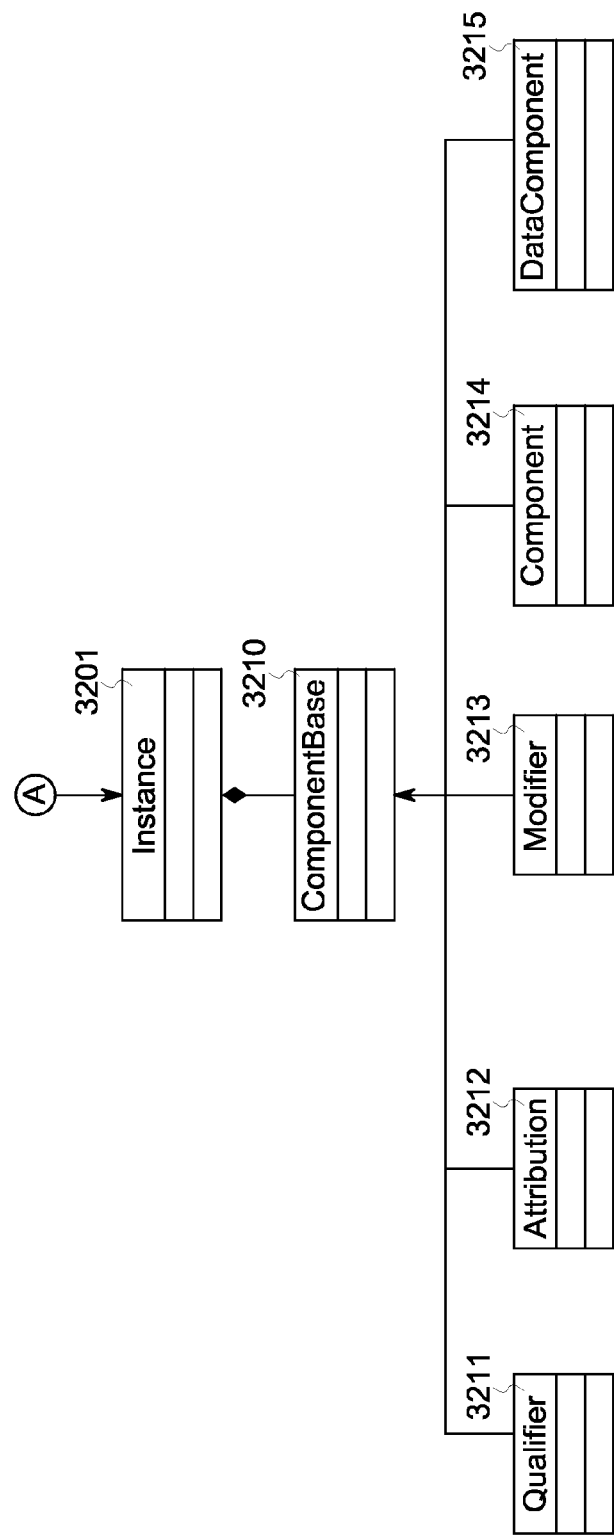

Reference classes, again as seen in the logical instance model, fall into an inheritance hierarchy; reference classes are defined through a process of progressive specialization. FIG. 32 shows a diagram 3200 (using Unified Modeling Language (UML) notation) of an inheritance hierarchy of reference classes in an example reference implementation. As depicted in the example of FIG. 32, a plurality of classes are combined in an inheritance hierarchy to form an instance 3201 via a component base 3210, a patient association 3220, a general association 3230, a general statement 3240, and a patient statement 3250. For example, the component based 3210 inherits from a qualifier 3211, an attribution 3212, a modifier 3213, a component 3214, a data component 3215, etc. The patient association 3220 is provided by a panel 3221, a collection 3222, a sequence 3223, a link 3224, an annotation 3225, and a patient relationship 3226. The general association 3230 is formed from a hierarchy of a location relationship 3231, a general collection 3232, an instance reference 3233, and a list 3234. The general statement 3240 is formed of a provider 3241, a location 3242, an encounter 3243, a contact 3244, an activity 3245, a patient 3246, and a data statement 3247. The patient statement 3250 inherits from a statement 3251, for example.

An attribute of a data object that is directly visible and referenced by the reference implementation is defined in a reference class. For example, instance identifiers are directly visible to the reference implementation in order to manage data instances, so instance identifiers are defined in the instance reference class to allow direct access to that attribute by the reference implementation.

A number of the attributes visible to the reference implementation (though not all) are directly owned and managed by the reference implementation (for example, the instance identifier, the data model type identifier, etc.) and may not be modified by an application consuming the data instance (the applications see these attributes as read-only constants).

Other attributes are visible, modifiable, and owned by consuming applications but are desirable to define in a reference class to allow the reference implementation to directly use those attributes in the management of the data instances, for example, for integrity enforcement through use of referential integrity constraints in the database, for performance optimization such as indexes over the attribute, etc.

In certain examples, it is desirable to allow attributes in a data model to be "promoted" to a reference class for optimization purposes or "demoted" from the reference class when no longer required by the reference implementation without requiring changes to applications consuming the data instances and data models describing those instances. To allow this kind of application independence, all attributes defined in a reference class are also represented by a data model that may be consumed by the application. The application sees only the instance defined by the data model, not concrete reference class objects. The reference implementation translates attributes defined in a reference class to the same form used to represent attributes defined in a data model, thus allowing applications to consume these attributes without any direct coupling with the reference implementation.

A data model may be defined within a specific reference class in order for instances of that data model to be instantiated (that is, a reference class represents the physical implementation of a data instance without which an instance may not physically exist). A data model inherits the attributes and behaviors of the reference class within which it is defined.

Since a data model may also be a specialization of some other data model, the designation of a reference class in a data model represents a limited form of multiple inheritance wherein a data model inherits attributes from both the model defining the reference class and from the model being specialized.

In certain examples, data instances defined via the Abstract Instance Model behave as objects (in the object-oriented programming sense) where the attributes within the objects are structured hierarchically. Additionally, since elements within the object are defined externally in a separate data model, those elements are represented within the object generically (for example, the object contains a qualifier object containing a key attribute representing that the qualifier describes a body position; it does not contain an attribute named "body position").

The Abstract Instance Model does not specify or require any specific instance storage (e.g., persistence) strategy. Any persistence strategy that allows data objects to be stored, retrieved, and queried is permitted by the model. For example, an object, XML, or relational database may be used to store instances as long as the appropriate translations or transformations are performed.

An example reference implementation stores instances within a relational database. When writing instances, objects are mapped to a relational structure and mapped back to objects when read (e.g., an object-relational-mapping (ORM) mechanism is implemented). Reference classes are stored in distinct sets of relational tables (e.g., schemas) to allow independent management of the data class. Components within data instances, since they are represented generically, are stored using an associative data model. Optimizations, such as materialized paths to components, are performed to allow efficient querying of the hierarchal data structures within instances.

In an example reference implementation, the database is treated as an immutable, forward-only log. That is, stored data instances are never updated or modified; rather, when changes to a data instance occur, a new version of the data instance is created while leaving previous versions intact. Previous versions remain accessible to applications requiring historical information.

The logical model implementing the Clinical Element Model represents clinical data using a two-layer data modeling approach in which the structure or representation of a data object (that is, a model defining the implementation of an instance of data) is separated from the definition of the information contained within the data object (that is, a model defining the content and semantics of an instance of data). The logical model defining the information contained within an instance of data is referred to as the Abstract Constraint Model.

As earlier described, an instance of the Abstract Instance Model is a generic data structure that may contain the data described by any arbitrary data model. The Abstract Constraint Model defines a mechanism (e.g., a constraint model) to constrain an instance to contain only the information applicable to a single clinical data concept.

Within the Clinical Element Model instances of the Abstract Constraint Model are commonly referred to variously as Clinical Element Models, Clinical Element Types, CE Types, data models, constraint models, and sometimes simply as models or types. Within the context of the Constraint Definition Language, the source form of a data model is referred to as a Clinical Element Model (or as a CEM, constraint model or simply a model); the compiled form of a data model is referred as a Clinical Element Type (or as a CE Type or simply a type). Models are used during the authoring process; types are used by running programs constructing and consuming data instances. Both models and types are often referred to generically as instances of the Abstract Constraint Model.

A constraint model (e.g., an instance of the abstract constraint model) is a representation of a detailed clinical model based on the concept of a constraint, that is, a statement that defines a data element by restricting or constraining the values that can be legally stored in the element; it may also be viewed as a statement that excludes all data elements but those desired.

Constraint statements operate on the principle of progressive restriction; that is a constraint statement may limit the data within the element to a particular set of possible data items and a subsequent constraint statement (often in another model) will further restrict the data described by the first constraint statement to a proper subset of the data. This principle allows the definition of more general constraint models that may be used as elements within other constraint models; each containing constraint model may further restrict the data values described by the included constraint model to allow it to better describe that specific instance of clinical data.

In the Clinical Element Model, constraint statements may restrict elements of a data instance only to the types of values described earlier in the Clinical Element Information Model, since only instances so constructed may be represented in the Abstract Instance Model (the physical representation of the instance).

A constraint model may be constructed by either specializing some other constraint model through inheritance and/or by including other constraint models to define specific elements of the constraint model (that is, a constraint model may be composed of other constraint models), for example. A constraint model includes a model declaration followed by a model body which contains an unordered set of constraint statements, each constraint statement defining an element, or attribute, of an instance by limiting the information that the element may contain to a small set of possible data items.

A constraint statement may be very specific, limiting the element to contain only a specific data item, or it may be broader, limiting the element to contain a set of data items (generally drawn from a single domain of data). Each constraint statement is composed of a series of constraint expressions, each expression limiting some facet of the element. In the Constraint Definition Language, constraint statements may also contain processing instructions, that is, instructions to the model compiler or reference implementation to apply some process to the data element. For example, set a default value, convert a value a normalized form, etc. Some constraint expressions may be required in a constraint statement (for example, the reference class constraint expression), others may be optional.

For example, a constraint statement might contain constraint expressions that limit an element to contain instances of a specific reference class (say, a qualifier), limit the data contained in the element to that described by a specific model (say, a body position model), limit the number (or cardinality) of data items that may be contained in the element (say, zero or one), limit the domain from which data values in the element are derived (for example, a vocabulary domain), and the like.

Inheritance refers to the specialization of one instance of the Abstract Constraint Model (e.g., a base model) to create a second instance of the Abstract Constraint Model (e.g., a derived model) where the second instance is derived from the first instance by specifying constraint expressions in the derived model that specialize constraint expressions in the base model.

Inheritance may be used as a way to share common constraint statements among several semantically related models. For example, common attributions in all clinical observations may be placed in an Observation model and that model may then be used as the basis for Temperature observation models, Pulse Rate observation models, Blood Pressure observation models, etc. Programs using these models can treat all the models similarly with the guarantee that all of the elements defined in Observation are available in all models.

Using inheritance, hierarchies (or ontologies) of models may be constructed and treated generically. For example, Laboratory Result models may be specialized into Chemistry Laboratory Models and Microbiology Laboratory Models, etc. Using these hierarchies, queries such as "retrieve all Chemistry Laboratory Model data instances" may be constructed, information common to all Chemistry Laboratory Models may be displayed generically, and the like.

In general, inheritance is assumed to accord with the basic ontological principle of subsumption, which says that instances of a type B are also instances of type A, where type B is related to type A by the semantic relationship 'IS-A'.

Figure 33:
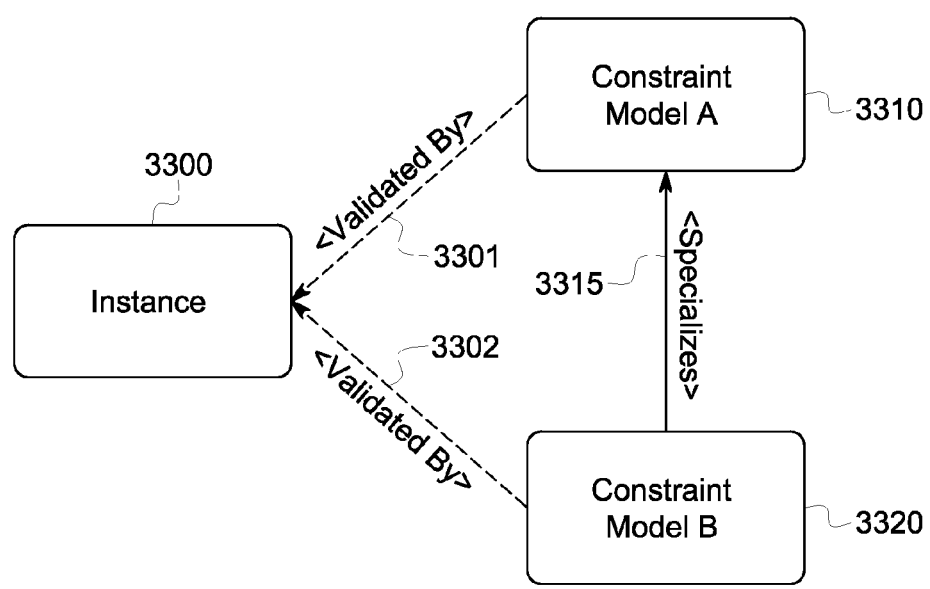
FIG. 33 illustrates an example abstract constraint model definition.

Starting from this general definition of inheritance, inheritance may be more specifically defined in the Abstract Constraint Model as follows. FIG. 33 illustrates an example Abstract Constraint Model definition. For an instance 3300, a constraint model A 3310 and/or a constraint model B 3320 can be used to validate 3301, 3302 the instance 3300. In the example, constraint model B 3320 specializes 3315 the constraint model A 3310. If constraint model B 3320 specializes constraint model A 3310, then any instance 3300 that is correct when validated using constraint model B 3320 will also be correct when validated using constraint model A 3310.

For this definition to be true, model B must be derived from model A via a process of restriction, that is, each constraint expression in model B must define a proper subset of any corresponding constraint expression in model A. This observation allows the statement of the first corollary derived from the Abstract Constraint Model's definition of inheritance. A model B may be said to be a specialization of a Model A under subsumption (e.g., the IS-A relationship holds between B and A) if and only if all constraint expressions in Model B are restrictions (e.g., define a proper subset) of the corresponding constraint expressions in Model A.

For example, if a constraint expression in model A specifies that an element may contain any value from the set {a, b, c} and model B also specifies the same constraint expression (as a specialization of the expression in A), the constraint expression in B may legitimately restrict that value to be any one of the sets {a, b, c}, {a, b}, {a, c}, {b, c}, {a}, {b}, or {c}.

Cardinality constraint expressions (e.g., expressions that define the number of instances of the specified data object that may be contained in the set defined by the element) further illustrate inheritance in the Abstract Constraint Model.

First, assume that model A specifies a cardinality constraint expression for an element of cardinality(0 . . . 1), that is the element may contain either zero or one instance (e.g., it is optional). Model B could specialize this constraint expression by restricting the element to any one of the expressions cardinality(0 . . . 1), cardinality(0), or cardinality(1). Each of these expressions satisfies our definition of specialization via restriction.

However, model B could not specify any cardinality constraint expression greater than 1 since an instance of B containing more than 1 instance of that element would no longer be correct when validated against model A (which can contain at most 1); this illustrates an example of the inverse of restriction, extension.

Similarly if model A specified an element with a cardinality(1) constraint expression, model B could not override that element with a cardinality(0) constraint expression since the instance would no longer be correct when validated against model A (again, this expression is not a proper restriction, it too is an example of extension).

Next assume that an element is not defined in model A. This is equivalent to specifying an element in model A with a cardinality constraint expression of cardinality(0); that is, no instance of the element is allowed. There is no possible restriction of cardinality(0) except for cardinality(0). Hence, model B may not specialize model A by adding elements to model A. The addition of an element undefined in a base model by a derived model represents an extension of the base model; it is analogous to expanding the domain of a data element defined in the base model in the derived model.

This leads to the statement of the second corollary derived from our definition of inheritance in the Abstract Instance Model. No model B may be said to be a specialization of a model A under subsumption if model B contains constraint expressions that extend corresponding constraint expressions in model A (e.g., where the domain described by expressions in model A is a subset of that described by model B). That is, the IS-A relationship between a derived model and a base model does not hold when the derived model is an extension of the base model.

When a model is modified to create a new version of the model that replaces the previous version in the running system, existing instances that are valid against the first version of the model should continue to be valid against the new version of the model (for example, instances defined via the first version may exist in the database and need to be read using the new version).

Modification of constraint models represents a special case of the semantics of inheritance in the Abstract Constraint Model. In order to insure backward compatibility of models with instances, the earlier version of the model should represent a restriction of the later version. If the older version is a restriction of the new version, instances that are valid with the old version should be valid with the new version.

This leads to a third corollary derived from the definition of inheritance. An instance that is correct when validated against a model A is correct when validated against a model A', where A' is derived as a modification of the constraint expressions in model A, if and only if all constraint expressions in model A are restrictions of the corresponding constraint expressions in model A'.

In general, this rule is used to help insure that creating a new version of a model does not render the system unable to read instances created using the older version and to insure that application programs compiled using the earlier version of the model as a reference (for example, using an object façade (representing the model) over the instance) do not fail when presented with an instance created with the new version of the model.

Inheritance is used in programming languages to factor common behavior and attributes into a base model where that model can be reused as the basis of many derived models. For example, an Observation model might define all of the basic attributions of a clinical observation (e.g. observed time, observed by, etc.). A Temperature model would then extend Observation by adding an element to contain the observed temperature physical quantity. However, this use of inheritance represents an extension of the base model (it extends the cardinality of the temperature element from 0 to 1), which violates the definition of inheritance in the Abstract Constraint Model and paradoxically leads to the conclusion that a Temperature is not an Observation. This implication of restriction based inheritance obviates one of the most common practical uses of inheritance. Because of this, the Constraint Definition Language implements two forms of inheritance: restriction and a limited form of extension.

Inheritance by restriction conforms exactly to the definition of inheritance in the Abstract Constraint Model. It is specified using the restricts keyword on a model declaration (a model declaration contains the keyword model followed by the name of the model). Restriction is most useful when a derived model is defining a proper subset of a domain defined by a base model.

Inheritance by extension may not conform to the definition inheritance in the Abstract Constraint Model because the IS-A relationship does not hold under extension. However, the Constraint Definition Language defines a form of extension that captures many of the more common desired uses of inheritance without violating the rules on restriction in a practical sense. Inheritance via extension is specified using the extends keyword on a model declaration.

Since this technique does not conform to the example definition of inheritance, the Constraint Definition Language applies a number of restrictions to extension to allow it to be safely and unambiguously used. First, models used as the basis for deriving models by extension may not be instantiated in the runtime system. Such base models are defined using the partial keyword as a modifier. Second, only models with the partial modifier may be extended since any model without the partial modifier is instantiable and is disallowed in the first rule. Third, any model derived via restriction may not be extended. Fourth, if any constraint expressions in the partial base model being extended are specialized in the derived model, the specializations must be proper restrictions. This implies that the only form of extension supported in derived classes is the addition of elements that do not exist in the base model.

A constraint statement defines a single data element within an instance. Most commonly, the type of the element is defined in another constraint model that is specified through a type constraint expression within the statement. The type constraint expression in the statement constrains the data element defined by that constraint statement to contain only data elements defined by the type (e.g., model) specified in the constraint statement or by a type that specializes (through inheritance) the indicated type. This represents a form of composition in which a model is composed from one or more models referenced as attributes of the model.

The Clinical Element Model, however, also allows the included model to be specialized within the context of the composition by applying constraint expressions to elements within the included model that further restrict the values in those elements. New restrictions may be applied to any constraint expression within the included model or within any model included by that model, etc.

While this composition is not a direct form of inheritance, specializations to the models in the composition behave as if they were included in the model via multiple-inheritance (because of the ability of the model to specialize elements of the included model). For example, if a model for a temperature was defined with a constraint that the temperature could be represented in either Fahrenheit or Centigrade units was included in a constraint statement in another model, the including model could restrict the temperature representation to only Centigrade units. This capability expands the opportunity for reuse of models in different contexts where a more restricted form of the element is required but without the need to proliferate several slightly different versions of the same clinical model.

Polymorphism, in the Clinical Element Model, refers to an ability of one type to appear as and be used like another type to allow programs to be written so as to be unaware of the differences between the types. To allow this, some set of types are derived from a common base type using either extension or restriction; programs are written as if all of the derived types are actually the base type and do not differentiate between any of the derived types (of course, this implies that attributes that are unique to a derived type are not available to the program when accessed polymorphically).

For example, if a serum sodium laboratory result type and a serum potassium laboratory result type were both derived from a chemistry laboratory result type, a program may treat both of the derived types generically as if they were the chemistry laboratory result type. This is a common and useful pattern for many programs that consume Clinical Element Types.

However, since all elements in a derived type must be restrictions of the corresponding elements in the base type, derived types do not behave completely polymorphically. Since a base type is less restrictive than a derived type, treating the derived type as if it were the base type may allow values to be written to an element that would not be correct when validated against the derived class (though elements being read from instances of the derived type would be valid when treated as if they were instances of the base type).

While there are mechanisms that would allow types to be treated completely polymorphically, the example implementation of the Clinical Element Model allows polymorphic access to an instance only when values are being read from instances. Elements may only be written to an instance when the type defining the instance is treated directly as itself (e.g., not treated as the base type). This may be viewed as a limited form of polymorphism for Clinical Element Types.

Multiple inheritance refers to the ability for a type to derive from more than one base type (that is, to inherit attributes from more than one type). The Constraint Definition Language supports a limited form of multiple inheritance in that any type may derive from both a type representing a reference class and a single other type.

When processing instruction expressions such as default and normal are specified both in an element of a derived model and in the corresponding element in the base model, the rules used for constraint expressions requiring the expression in the derived model to be a restriction of the expression in the base model do not apply. Rather the expression in the derived model simply overrides (e.g., replaces) the corresponding expression in the base model; the values specified as arguments to processing instructions in the derived and base models should be considered completely unrelated.

Thus, certain examples describe systems and methods utilizing a Constraint Definition Language (CDL) to define Detailed Clinical Models and constraints used to describe a specific clinical data item.

The Constraint Definition Language (CDL) defines a compiled, context free language allowing the definition of Detailed Clinical Models. Models are authored as text files, compiled, and stored as objects in the content database of the system using the model. Programs read the object to retrieve information about the model (e.g., attributes, base models, etc.).

A possible logical model to represent such Detailed Clinical Model uses a two-layer data modeling approach in which the structure or representation of a clinical data object (that is, an instance of data) is separated from the definition of the information contained within the clinical data object (that is, a model defining the instance of data). This logical model defines the information in a Detailed Clinical Model as a set of constraints progressively limiting (or restricting) the legal data values in a Detailed Clinical Model until a specific clinical data item is defined.

While an example manner of implementing systems and methods have been illustrated in the figures, one or more of the elements, processes and/or devices illustrated in the figures may be combined, divided, re-arranged, omitted, eliminated and/or implemented in any other way. Further, one or more components and/or systems may be implemented by hardware, software, firmware and/or any combination of hardware, software and/or firmware. Thus, for example, any of the example components and/or systems may be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the example components and/or systems are hereby expressly defined to include a tangible medium such as a memory, DVD, Blu-ray, CD, etc., storing the software and/or firmware. Further still, any of the example systems may include one or more elements, processes and/or devices in addition to, or instead of, those illustrated in the figures, and/or may include more than one of any or all of the illustrated elements, processes and devices.

The flow diagrams depicted in the figures are representative of machine readable instructions that can be executed to implement example processes and/or systems described herein. The example processes may be performed using a processor, a controller and/or any other suitable processing device. For example, the example processes may be implemented in coded instructions stored on a tangible medium such as a flash memory, a read-only memory (ROM) and/or random-access memory (RAM) associated with a processor (e.g., the example processor 3412 discussed below in connection with FIG. 34). Alternatively, some or all of the example processes may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes may be implemented manually or as any combination(s) of any of the foregoing techniques, for example, any combination of firmware, software, discrete logic and/or hardware. Further, although the example processes are described with reference to the figures, other methods of implementing the processes of may be employed. For example, the order of execution of the blocks may be changed, and/or some of the blocks described may be changed, eliminated, sub-divided, or combined. Additionally, any or all of the example processes of may be performed sequentially and/or in parallel by, for example, separate processing threads, processors, devices, discrete logic, circuits, etc.

Figure 34:
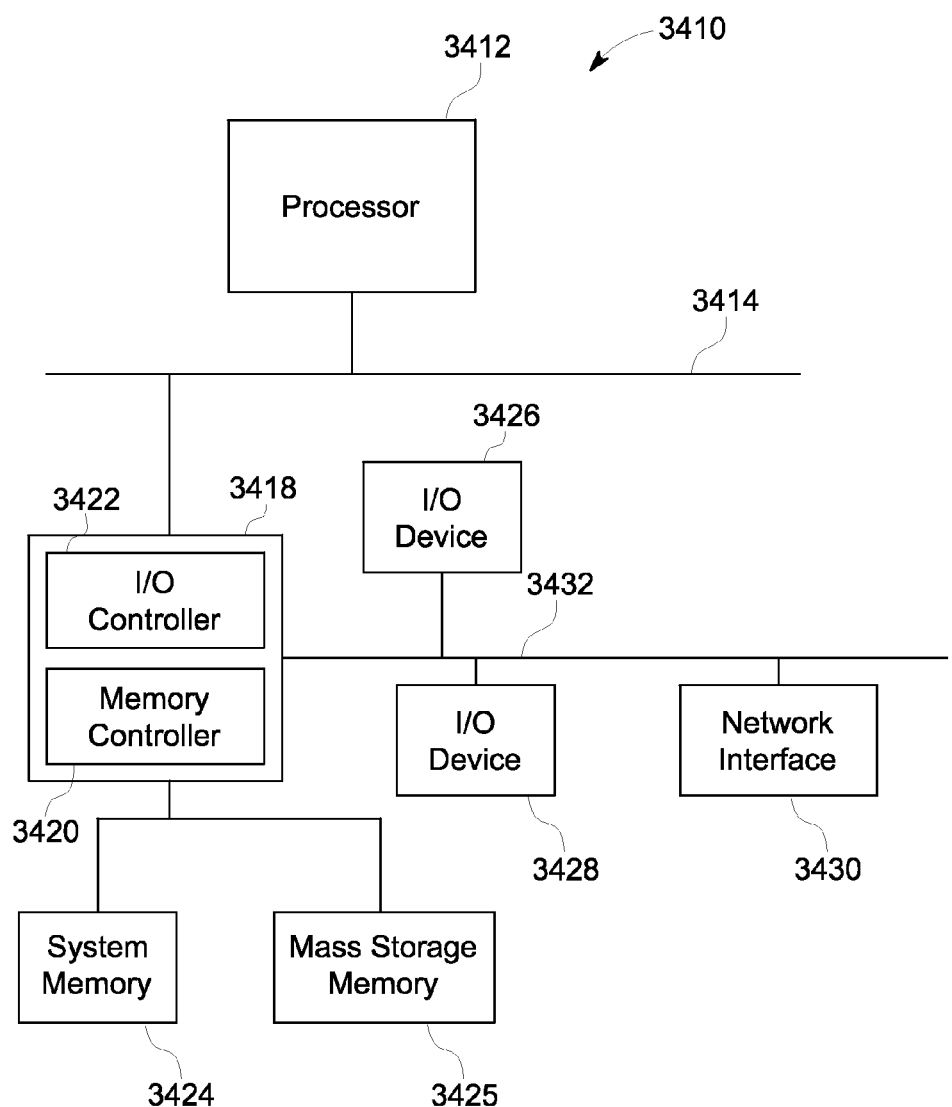
FIG. 34 is a block diagram of an example processor system that may be used to implement the systems, apparatus and methods described herein.

FIG. 34 is a block diagram of an example processor system 3410 that may be used to implement the apparatus and methods described herein. As shown in FIG. 34, the processor system 3410 includes a processor 3412 that is coupled to an interconnection bus 3414. The processor 3412 may be any suitable processor, processing unit or microprocessor. Although not shown in FIG. 34, the system 3410 may be a multi-processor system and, thus, may include one or more additional processors that are identical or similar to the processor 3412 and that are communicatively coupled to the interconnection bus 3414.

The processor 3412 of FIG. 34 is coupled to a chipset 3418, which includes a memory controller 3420 and an input/output (I/O) controller 3422. As is well known, a chipset typically provides I/O and memory management functions as well as a plurality of general purpose and/or special purpose registers, timers, etc. that are accessible or used by one or more processors coupled to the chipset 3418. The memory controller 3420 performs functions that enable the processor 3412 (or processors if there are multiple processors) to access a system memory 3424 and a mass storage memory 3425.

The system memory 3424 may include any desired type of volatile and/or non-volatile memory such as, for example, static random access memory (SRAM), dynamic random access memory (DRAM), flash memory, read-only memory (ROM), etc. The mass storage memory 3425 may include any desired type of mass storage device including hard disk drives, optical drives, tape storage devices, etc.

The I/O controller 3422 performs functions that enable the processor 3412 to communicate with peripheral input/output (I/O) devices 3426 and 3428 and a network interface 3430 via an I/O bus 3432. The I/O devices 3426 and 3428 may be any desired type of I/O device such as, for example, a keyboard, a video display or monitor, a mouse, etc. The network interface 3430 may be, for example, an Ethernet device, an asynchronous transfer mode (ATM) device, an 802.11 device, a DSL modem, a cable modem, a cellular modem, etc. that enables the processor system 3410 to communicate with another processor system.

While the memory controller 3420 and the I/O controller 3422 are depicted in FIG. 34 as separate blocks within the chipset 3418, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

The invention claimed is:

1. A system for user customization of clinical data objects using a clinical modeling language, the system comprising:
a processor and a memory to implement:
a constraint definition language processor to define a detailed clinical model to express a clinical concept as a standardized and reusable set of clinical knowledge, the constraint definition language processor using a compiled, context-free constraint definition language to define the detailed clinical model as a compiled object, wherein compiling the detailed clinical model into a compiled object validates the detailed clinical model for correctness and consistency, the constraint definition language processor providing the compiled object as content for at least one of a clinical content database and a clinical information system, wherein content represents one or more parameters to instruct a clinical application,
wherein the detailed clinical model defines an information model representing one or more instances of clinical information and a logical model representing an implementation of this information model, wherein the logical model represents clinical data using a two-layer data modeling approach in which a structure of a clinical data object is separated from a definition of information contained within the clinical data object, the logical model (i) defining information in the detailed clinical model as a set of constraints progressively limiting allowable data values in the detailed clinical model until a specific clinical data item is defined and (ii) defining relationships among information in the detailed clinical model,
wherein the constraint definition language processor authorizes the detailed clinical model including the information model and the logical model and wherein the constraint definition language processor validates the detailed clinical model for correctness and consistency and compiles the detailed clinical model into the compiled object to instruct the clinical application regarding execution and consumption of data,
the detailed clinical model extensible to allow a new detailed clinical model to be defined by a content author and an attribute to be added to an existing detailed clinical model to change behavior of the clinical application without requiring corresponding changes to the clinical application or underlying database structures.

2. The system of claim 1, wherein the constraint definition language processor includes a compiler, wherein the detail clinical model object is to be validated for correctness and consistency by the compiler to help ensure changes to models are allowable and safe.

3. The system of claim 1, wherein the detailed clinical model defines concepts, relationships, constraints, and rules that specify semantics of an item of clinical information.

4. The system of claim 3, wherein an item of clinical information involves a plurality of relationships, constraints, and rules specified by one or more detailed clinical models.

5. The system of claim 3, wherein the detailed clinical model provides one or more of an attribute, an annotation, a sequence, and a semantic link.

6. The system of claim 1, in which the detailed clinical model represents a vocabulary concept, a physical measurement, a patient identifier and a time.

7. The system of claim 1, wherein the detailed clinical model defines a panel referencing one or more statements including one or more values taken as a single observation having associations between the one or more statements.

8. The system of claim 1, wherein the compiled object is formed using one or more detailed clinical models including an inheritance hierarchy of reference classes.

9. A tangible computer-readable storage device including a set of instructions for execution using a processor, the instructions, when executed, providing a system comprising:
a constraint definition language processor to define a detailed clinical model to express a clinical concept as a standardized and reusable set of clinical knowledge, the constraint definition language processor using a compiled, context-free constraint definition language to define the detailed clinical model as a compiled object, the constraint definition language processor providing the compiled object as content for at least one of a clinical content database and a clinical information system, wherein content represents one or more parameters to instruct a clinical application,
wherein the detailed clinical model defines an information model representing one or more instances of clinical information and a logical model representing an implementation of this information model, wherein the logical model represents clinical data using a two-layer data modeling approach in which a structure of a clinical data object is separated from a definition of information contained within the clinical data object, the logical model (i) defining information in the detailed clinical model as a set of constraints progressively limiting allowable data values in the detailed clinical model until a specific clinical data item is defined and (ii) defining relationships among information in the detailed clinical model,
wherein the constraint definition language processor authorizes the detailed clinical model including the information model and the logical model and wherein the constraint definition language processor validates the detailed clinical model for correctness and consistency and compiles the detailed clinical model into the compiled object to instruct the clinical application regarding execution and consumption of data,
the detailed clinical model extensible to allow a new detailed clinical model to be defined by a content author and an attribute to be added to an existing detailed clinical model to change behavior of the clinical application without requiring corresponding changes to the clinical application or underlying database structures.

10. The computer-readable storage device of claim 9, wherein the constraint definition language processor includes a compiler, wherein the detail clinical model object is to be validated for correctness and consistency by the compiler to help ensure changes to models are allowable and safe.

11. The computer-readable storage device of claim 9, wherein the detailed clinical model defines concepts, relationships, constraints, and rules that specify semantics of an item of clinical information.

12. The computer-readable storage device of claim 11, wherein an item of clinical information involves a plurality of relationships, constraints, and rules specified by one or more detailed clinical models.

13. The computer-readable storage device of claim 11, wherein the detailed clinical model provides one or more of an attribute, an annotation, a sequence, and a semantic link.

14. The computer-readable storage device of claim 9, in which the detailed clinical model represents a vocabulary concept, a physical measurement, a patient identifier and a time.

15. The computer-readable storage device of claim 9, wherein the detailed clinical model defines a panel referencing one or more statements including one or more values taken as a single observation having associations between the one or more statements.

16. The computer-readable storage device of claim 9, wherein the compiled object is formed using one or more detailed clinical models including an inheritance hierarchy of reference classes.

17. A method for user customization of clinical data objects using a clinical modeling language, the method comprising:
receiving an input including a clinical concept;
associating the clinical concept with one or more detailed clinical models, the detailed clinical models expressing the clinical concept as a standardized and reusable set of clinical knowledge;
compiling the modeled clinical concept using a compiled, context-free constraint definition language to define the one or more detailed clinical models of the clinical concept as a compiled object; and
providing the compiled object as content for at least one of a clinical content database and a clinical information system, wherein content represents one or more parameters to instruct a clinical application,
wherein the detailed clinical model defines an information model representing one or more instances of clinical information and a logical model representing an implementation of this information model, wherein the logical model represents clinical data using a two-layer data modeling approach in which a structure of a clinical data object is separated from a definition of information contained within the clinical data object, the logical model (i) defining information in the detailed clinical model as a set of constraints progressively limiting allowable data values in the detailed clinical model until a specific clinical data item is defined and (ii) defining relationships among information in the detailed clinical model
wherein the detailed clinical model including the information model and the logical model is authorized and validated for correctness and consistency and compiled into the compiled object to instruct the clinical application regarding execution and consumption of data,
the detailed clinical model extensible to allow a new detailed clinical model to be defined by a content author and an attribute to be added to an existing detailed clinical model without requiring corresponding changes to the clinical application or underlying database structures.

18. The method of claim 17, wherein the set of constraints progressively limiting allowable data values in the detailed clinical model until a specific clinical data item is defined comprise a set of context variants of a content item.

19. The system of claim 1, wherein the set of constraints progressively limiting allowable data values in the detailed clinical model until a specific clinical data item is defined comprise a set of context variants of a content item.

20. The computer-readable storage device of claim 9, wherein the set of constraints progressively limiting allowable data values in the detailed clinical model until a specific clinical data item is defined comprise a set of context variants of a content item.

* * * * *